US012570665B2

(12) United States Patent
Chiang et al.

(10) Patent No.: US 12,570,665 B2
(45) Date of Patent: Mar. 10, 2026

(54) COMPOSITIONS COMPRISING FULLERENYL MESOCHLORIN NANO-PHOTOSENSITIZERS WITH COVALENTLY BOUND ANTIBIOTICS AND THEIR USES IN COMBINATION THERAPY

(71) Applicants: The University of Massachusetts, Boston, MA (US); The General Hospital Corporation, Boston, MA (US)

(72) Inventors: Long Y. Chiang, Acton, MA (US); Tianhong Dai, Malden, MA (US); Min Wang, Dublin, OH (US)

(73) Assignee: University of Massachusetts, Boston, MA (US)

( * ) Notice: Subject to any disclaimer, the term of this patent is extended or adjusted under 35 U.S.C. 154(b) by 1038 days.

(21) Appl. No.: 17/617,518

(22) PCT Filed: Jun. 9, 2020

(86) PCT No.: PCT/US2020/036787

§ 371 (c)(1),
(2) Date: Dec. 8, 2021

(87) PCT Pub. No.: WO2020/251933

PCT Pub. Date: Dec. 17, 2020

(65) Prior Publication Data

US 2022/0259219 A1 Aug. 18, 2022

Related U.S. Application Data

(60) Provisional application No. 62/859,331, filed on Jun. 10, 2019.

(51) Int. Cl.
*C07D 487/22* (2006.01)
*A61K 41/00* (2020.01)
*C01B 32/152* (2017.01)

(52) U.S. Cl.
CPC ........ *C07D 487/22* (2013.01); *A61K 41/0071* (2013.01); *C01B 32/152* (2017.08)

(58) Field of Classification Search
CPC .. C07D 487/22; A61K 41/0071; C01B 32/152
See application file for complete search history.

(56) References Cited

U.S. PATENT DOCUMENTS

| | | | | |
|---|---|---|---|---|
| 5,109,016 | A | 4/1992 | Dixon et al. | |
| 5,177,248 | A | 1/1993 | Chiang et al. | |
| 5,294,732 | A | 3/1994 | Chiang et al. | |
| 5,416,188 | A | 5/1995 | Chiang et al. | |
| 5,466,681 | A | 11/1995 | Krivan et al. | |
| 5,635,581 | A | 6/1997 | Chiang et al. | |
| 5,648,523 | A | 7/1997 | Chiang | |
| 5,952,329 | A | 9/1999 | Cincotta et al. | |
| 5,994,410 | A | 11/1999 | Chiang et al. | |
| 6,002,035 | A | 12/1999 | Chiang et al. | |
| 6,020,523 | A | 2/2000 | Chiang | |
| 6,046,361 | A | 4/2000 | Chiang | |
| 6,455,709 | B1 | 9/2002 | Chiang et al. | |
| 6,462,070 | B1 | 10/2002 | Hasan et al. | |
| 6,576,655 | B2 | 6/2003 | Chiang et al. | |
| 6,790,963 | B2 | 9/2004 | Chiang et al. | |
| 6,827,926 | B2 | 12/2004 | Robinson et al. | |
| 6,906,050 | B2 | 6/2005 | Robinson | |
| 6,949,660 | B2 | 9/2005 | Chiang et al. | |
| 6,977,075 | B2 | 12/2005 | Hasan et al. | |
| 7,132,572 | B2 | 11/2006 | Chiang et al. | |
| 7,264,629 | B2 | 9/2007 | Simkin et al. | |
| 8,207,211 | B2 | 6/2012 | Wharton et al. | |
| 8,425,879 | B2 | 4/2013 | Brevet et al. | |
| 9,303,165 | B2 | 4/2016 | Lindsey et al. | |
| 9,308,185 | B2 | 4/2016 | Aicher et al. | |
| 9,365,722 | B2 | 6/2016 | Lindsey et al. | |
| 9,737,565 | B2 | 8/2017 | Mandel | |
| 2003/0176326 | A1 | 9/2003 | Nifantiev | |
| 2004/0186087 | A1 | 9/2004 | Grafe et al. | |
| 2004/0241173 | A1 * | 12/2004 | Wilson et al. | A61K 39/395 424/178.1 |
| 2005/0281777 | A1 | 12/2005 | Albrecht et al. | |
| 2007/0099154 | A1 | 5/2007 | Johnson | |
| 2007/0167619 | A1 * | 7/2007 | Love et al. | C07D 487/22 540/145 |
| 2009/0012008 | A1 | 1/2009 | Laptev et al. | |
| 2009/0131499 | A1 | 5/2009 | Castro et al. | |

(Continued)

FOREIGN PATENT DOCUMENTS

| | | | |
|---|---|---|---|
| CN | 103601727 | A | 2/2014 |
| CN | 103724356 | A | 4/2014 |

(Continued)

OTHER PUBLICATIONS

Environ. Sci. Technol. 2015, 49, 7456-7463 (Ballatore et al.) (Year: 2015).*
Tetrahedron 2006, 62, 1928-1936 (Schuster et al.) (Year: 2006).*
Nanomed. Nanotechnol. Biol. Med. 2013, 9, 570-579 (Sperandio et al.) (Year: 2013).*
Cancer Lett. 2009, 282, 63-76 (Mroz et al.) (Year: 2009).*
Huang, L., et al.; "Progressive cationic functionalization of chlorin derivatives for antimicrobial photodynamic inactivation and related vancomycin conjugate"; Photochemical & Photobioligacal Sciences, vol. 17; 2018; pp. 638-651.
Huang, Y.-Y. et al.; "Functionalized fullerenes in photodynamic therapy"; Journal of Biomedical Nanotechnology, vol. 10; 2014; pp. 1918-1936.

(Continued)

*Primary Examiner* — Amy C Bonaparte
*Assistant Examiner* — Derek Rhoades
(74) *Attorney, Agent, or Firm* — Stites & Harbison, PLLC

(57) ABSTRACT

Described herein are $C_{60/70}$PS-CB-Abx and nano-$C_{60/70}$PS compounds, their pharmaceutical compositions, and methods pf photodynamic therapy using the compounds and compositions.

6 Claims, 7 Drawing Sheets

(56) References Cited

U.S. PATENT DOCUMENTS

| | | | |
|---|---|---|---|
| 2009/0232755 A1 | 9/2009 | Baumann | |
| 2014/0163218 A1 | 6/2014 | Dei et al. | |
| 2018/0282344 A1 | 10/2018 | Costa et al. | |
| 2018/0305405 A1 | 10/2018 | Scherz et al. | |

FOREIGN PATENT DOCUMENTS

| | | | |
|---|---|---|---|
| EP | 2986617 | A1 | 2/2016 |
| EP | 3082788 | B1 | 11/2018 |
| WO | 199533463 | A2 | 12/1995 |
| WO | 2007064842 | A2 | 6/2007 |
| WO | 2009059270 | A1 | 5/2009 |
| WO | 2010129337 | A2 | 11/2010 |
| WO | 2013015774 | A1 | 1/2013 |
| WO | 2014171971 | A1 | 10/2014 |
| WO | 2017077299 | A1 | 5/2017 |

OTHER PUBLICATIONS

Huang, Y.Y., et al.; "Sodium nitrite potentiates antimicrobial photodynamic inactivation: Possible involvement of peroxynitrate"; Photochemical & Photobioligacal Sciences, vol. 18; 2019; pp. 505-515.

International Search Report and Written Opinion for International Application PCT/US2020/036787; International Filing Date: Jun. 9, 2020; Date of Mailing: Oct. 19, 2020; 16 pages.

Lu, Z., et al.; "Photodynamic therapy with a cationic functionalized fullerene rescues mice from fatal wound infections"; Nanomedicine, vol. 5; 2010; pp. 1525-1533.

Shi et al.; "A Tumoral Acidic pH-responsive Drug Delivery System Based on a Novel Photosensitizer (fullerent) for in Vitro and in Vivo Chemo-photodynamic Therapy"; Actda Biomaterialia; 10; pp. 1280-1291; (2014).

Wozniak, A., Grinholc, M.; "Combined Antimicrobial Activity of Photodynamic Inactivation and Antimicrobials—State of the Art"; Frontiers in Microbiology, vol. 9, Article 930; 2018; 19 pages.

Xing, B., et al.; "Multifunctional divalent vancomycin: the fluorescent imaging and photodynamic antimicrobial properties for drug resistant bacteria" Chemical Communications, vol. 47; 2011; pp. 1601-1603.

Yin, R. et al.; "Photodynamic therapy with decacationic [60] fullerene monoadducts: effect of a light absorbing e-donor antenna and micellar formulation"; Nanomedicine, vol. 10, Issue No. 4; 2014; pp. 795-808.

Yin, R., et al.; "Antimicrobial photodynamic inactivation with decacationic functionalized fullerenes: oxygen independent photokilling in presence of azide and new mechanistic insights"; Free Radical Biological & Medicine, vol. 79; 2014; pp. 14-27.

Zhang, Y., et al., "Potentiation of antimicrobial photodynamic inactivation mediated by a cationic fullerene by added iodide: in vitro and in vivo studies"; Nanomedicine, vol. 10; 2015; pp. 603-614.

* cited by examiner $Chl_{Pd}$-$N_{10}^{+}$
($LC38^{+}$)

VCMe-*m*$Chl_{Pd}$-$N_{10}^{+}$
(LC40e)

COMPOSITIONS COMPRISING FULLERENYL MESOCHLORIN NANO-PHOTOSENSITIZERS WITH COVALENTLY BOUND ANTIBIOTICS AND THEIR USES IN COMBINATION THERAPY

CROSS REFERENCE TO RELATED APPLICATIONS

This application is a National Stage application of PCT/US2020/036787, filed Jun. 9, 2020, which claims the benefit of priority to U.S. Provisional Application 62/859,331, filed Jun. 10, 2019, both of which are incorporated by reference in their entirety herein.

FIELD OF THE DISCLOSURE

The present disclosure is related to novel functionalized fullerene photosensitizers comprising covalently bound antibiotics and their use in antimicrobial photodynamic therapy.

BACKGROUND

The threat of antibiotic resistance in healthcare and community settings has reached new prominence in the popular press that the issue should be added to the list of global emergencies. It is now indisputable that antibiotic resistance is life-threatening in the same sense as cancer, both in the number of cases and the likely outcome. In addition to a direct result of antibiotic-resistant infections, many more die from other conditions that were complicated by an antibiotic-resistant infection. Therefore, there is a pressing need for the development of alternative treatment regimens for antibiotic-resistant infections.

One non-antibiotic approach that may overcome the problems of antibiotic resistance is antimicrobial photodynamic therapy (aPDT). aPDT is based on the use of a photosensitizer in combination with light irradiation to generate cytotoxic reactive oxygen species [ROS; e.g. singlet oxygen ($^1O_2$), superoxide radicals ($O_2^{-}\cdot$), or hydroxyl radicals ($HO\cdot$)]. These ROS are produced by photochemical reactions between non-toxic photosensitizers (PSs), harmless visible light, and oxygen leading to non-specific attack at the molecular components in bacterial cells aPDT has not been shown to produce resistance in bacteria even after many successive cycles of partial inactivation followed by regrowth. Local administration of photosensitizer into the infected area together with a relatively short PS-light interval allows bacterial destruction without undue damage to the surrounding host tissue. aPDT may be a broad-spectrum bactericide especially suitable for infections in which causative bacteria are localized to a specific anatomical location such as skin, urinary tract, etc.

The use of functionalized fullerenes for the purpose of aPDI and aPDT applications was demonstrated (see Lu, Z., Dai, T., Huang, L., Kurup, D. B., Tegos, G. P., Jahnke, A., Wharton, T., Hamblin, M. R. Photodynamic therapy with a cationic functionalized fullerene rescues mice from fatal wound infections. *Nanomed.* 2010, 5, 1525-33; Huang, Y.-Y., Sharma, S. K., Yin, R., Agrawal, T., Chiang, L. Y., Hamblin, M. R. Functionalized fullerenes in photodynamic therapy. *J. Biomed. Nanotechnol.* 2014, 10, 1918-1936; Yin, R., Wang, M., Huang, Y.-Y., Chiang, L. Y., Hamblin, M. R. Photodynamic therapy with decacationic [60]fullerene monoadducts: effect of a light absorbing $e^{-}$-donor antenna and micellar formulation. *Nanomedicine NBM,* 2014, 10(4), 795-808; Yin, R., Wang, M., Huang, Y.-Y., Landi, G., Vecchio, D., Chiang, L. Y., Hamblin, M. R. Antimicrobial photodynamic inactivation with decacationic functionalized fullerenes: oxygen independent photokilling in presence of azide and new mechanistic insights. *Free Radic Biol Med.* 2014, 79, 14-27; Zhang, Y., Dai, T., Wang, M., Vecchio, D., Chiang, L. Y., Hamblin, M. R. Potentiation of antimicrobial photodynamic therapy mediated by fullerenes bearing a decacationic and a decatertiary-amine chain with external multi-iodides: in vitro and in vivo results. *Nanomed.* (Lond.) 2015, 10, 603-614; Huang, Y. Y., Rajda, P. J., Szewczyk, G., Bhayana, B., Chiang, L. Y., Sarna, T., Hamblin, M. R. Sodium nitrite potentiates antimicrobial photodynamic inactivation: Possible involvement of peroxynitrate. *Photochem. Photobiol. Sci.* 2019, 18, 505-51.) Whereas the related polycationic chlorin and vancomycin conjugate in a sterically hindered short linkage was also demonstrated (see Huang, L., Wang, M., Huang, Y.-Y., El-Hussein, A., Chiang, L. Y., Hamblin, M. R. Progressive cationic functionalization of chlorin derivatives for antimicrobial photodynamic inactivation and related vancomycin conjugate. *Photochem. Photobiol. Sci.* 2018, 17, 638-651).

The bactericidal effects using a physical combination (non-covalent bonding analogous) of an aPDT photosensitizer and routinely applied antibiotics in in vitro (using biofilm and planktonic cultures) and in vivo experiments were reviewed (see the review article. Wozniak, A., Grinholc, M. *Frontiers in Microbiology,* 2018, 9, art. 930). This review article also included the synergy effects between aPDT and antibiotics in these antimicrobial approaches. One related covalent conjugation example was involving a $C_{60}$ molecule that linked with DOX, as an anticancer drug, for a combinatory cancer treatment (see Shi, J., et al. *Acta Biomaterialia* 2013, 10, 1280-1291). The other example was given by divalent vancomycin-porphyrin conjugate for photodynamic inactivation of vancomycin resistant enterococci (VRE) bacterial strains (see Xing, B., et al. *Chem Comm.* 2011, 47, 1601-1603).

What is needed are novel functionalized fullerenes such as $C_{60/70}$/PS-CB-Abx, where PS means "photosensitizer", CB means "covalently bonded", and Abx means "antibiotic molecule", for use in antimicrobial photodynamic therapy applications.

BRIEF SUMMARY

In one aspect, a $C_{60/70}$/PS-CB-Abx compound has the following formula (I):

(I)

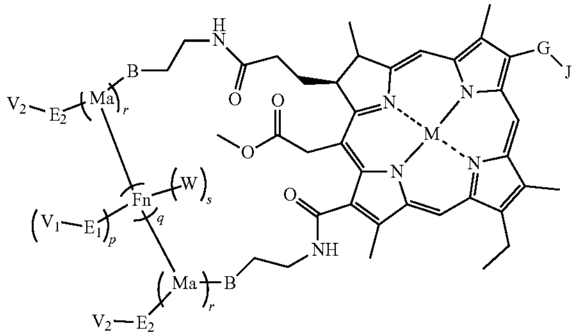

wherein

Fn is a fullerene core;

M is a metal ion;

B is amino-$C_{2-200}$ alkyl ether, amino-$C_{2-200}$ alkyl, hydroxy-$C_{2-200}$ alkyl ether, or hydroxy-$C_{2-200}$ alkyl;

Ma is —NH—CO-cyclopropanyl-CO— or —O—CO-cyclopropanyl-CO—;

G is —CH(O—$V_2$)—$CH_2$ or —CH(O—CO—Z—$V_2$)—$CH_2$;

J is $E_3$-Abx; wherein Abx is an amino or amide group-containing antibiotic molecule;

$E_1$, $E_2$, and $E_3$ are each independently $Y_1$,$Y_2$-amino, ($Y_1$,$Y_2$-alkyl)-amino, $Y_1$,$Y_2$-ethylenediamino, (dihydroxymethyl)alkylamino, ($X_1$,$X_3$-aryl)amino, $X_1$,$X_3$-aryloxy, $Y_2$-alkoxy, $Y_1$,$Y_2$-alkoxy, ($Y_1$,$Y_2$-amino) alkoxy, ($Y_1$,$Y_2$,$Y_3$-aryl)oxy, (dihydroxyalkyl)-aryloxy, ($Y_1$,$Y_2$,$Y_3$-alkyl)amino, ($Y_1$,$Y_2$,$Y_3$-aryl)amino, dihydroxyalkylamino, $Y_1$,$Y_2$,$Y_3$-alkoxy, (trihydroxyalkyl) alkoxy, (trihydroxyalkyl)alkylamino, (dicarboxyalkyl) amino, $Y_2$-thio, ($Y_1$,$Y_2$,$Y_3$-alkyl)thio, ($X_1$,$X_3$-aryl) thio, ($Y_1$,$Y_2$-alkyl)thio, (dihydroxyalkyl)thio, $Y_1$,$Y_2$-dioxoalkyl, tri-($Y_1$,$Y_2$,$Y_3$-methylaminocarboxyethyl) methylamino, ((glycosidyl)oxoheteroaryl)amino, ((glycosidyl)oxoaryl)amino, ($X_1$,$X_2$,$X_3$-heteroaryl) amino, ($X_1$-diarylketone)amino, (T,$X_1$-oxoaryl)amino, (T,$X_1$-dioxoaryl)amino, ($Y_1$-alkyl,$Y_2$-alkyldioxoheteroaryl)amino, ($Y_1$-alkyl,$Y_2$-alkyldioxoaryl)amino, (di ($Y_1$,$Y_2$-methyl)dioxoheteroaryl)amino, (di($Y_1$,$Y_2$-methyl)dioxoaryl)amino, ((glycosidyl)heteroaryl) amino, ((glycosidyl)aryl)amino, ((carboxylacetylalkyl) oxo-heteroaryl)amino, ((carboxylacetylalkyl)oxoaryl) amino, ((isopropylaminohydroxy-alkoxy)aryl)amino, $X_1$,$X_2$,$X_3$-alkylaryl)amino, ($X_1$,$X_2$,$X_3$-heteroaryl)oxy, (isopropylaminohydroxyalkyl)aryloxy, ($X_1$,$X_2$,$X_3$-oxoheteroaryl)oxy, ($X_1$,$X_2$,$X_3$-oxoaryl)oxy, ($X_1$,$Y_1$-oxoheteroaryl)oxy, ($X_1$-diarylketone)oxy, (T,$X_1$-oxoaryl)oxy, ($X_1$,$X_2$-dioxoaryl)oxy, ($Y_1$,$Y_2$,di-aminodihydroxy)alkyl, ($X_1$,$X_2$-heteroaryl)thio, ((tricarboxylalkyl)ethylene-diamino)alkoxy, ($X_1$,$X_2$-oxoaryl)thio, ($X_1$,$X_2$-dioxoaryl)thio, (glycosidylheteroaryl)thio, (glycosidylaryl)thio, $Y_1$-alkyl(thiocarbonyl)thio, $Y_1$,$Y_2$,-alkyl(thiocarbonyl)thio, $Y_1$,$Y_2$,$Y_3$-alkyl(thiocarbonyl)thio, ($Y_1$,$Y_2$-aminothiocarbonyl) thio, (pyranosyl)thio, cysteinyl, tyrosinyl, (phenylalaninyl)amino, (dicarboxyalkyl)thio, (amino-aryl)$_{1-100}$amino, (pyranosyl)$_{1-100}$amino, ($Y_1$-amino-aryl)$_{1-100}$amino, (amino(sulfoaryl))$_{1-100}$amino, peptidyl, thymidinyl, uridinyl, guanosinyl, adenosinyl, cholesteryl, or biotinylalkoxy; wherein T is halo;

each of $X_1$, $X_2$, and $X_3$ is each independently —$Y_2$, —O—$Y_2$, —S—$Y_2$, —NH—$Y_2$, —CO—O—$Y_2$, —O—CO—$Y_2$, —CO—NH—$Y_2$, —CO—N$Y_1Y_2$, —NH—CO—$Y_2$, —$SO_2$—$Y_2$, —$SO_2$—O—$Y_2$, —CH$Y_1Y_2$, or —N$Y_1Y_2$;

each of $Y_1$, $Y_2$, and $Y_3$ is each independently —H, -Q-Z—H or —Z—H; in which each Q, independently, is —$R^a$—O—[Si($CH_3$)$_2$—O—]$_{1-100}$-, —$C_{1-2000}$ alkyl-, —$C_{6-40}$ aryl-, —$C_{7-2000}$ alkylaryl-, —$C_{7-2000}$ arylalkyl-, —($C_{1-30}$ alkyl ether)$_{1-100}$-, —($C_{6-40}$ aryl ether)$_{1-100}$-, —($C_{7-2000}$ alkylaryl ether)$_{1-100}$-, —($C_{7-2000}$ arylalkyl ether)$_{1-100}$-, —($C_{1-30}$ alkyl thioether)$_{1-100}$-, —($C_{6-40}$ aryl thioether)$_{1-100}$-, —($C_{7-2000}$ alkylaryl thioether)$_{1-100}$-, —($C_{7-2000}$ arylalkyl thioether)$_{1-100}$-, —($C_{2-50}$ alkyl ester)$_{1-100}$-, —($C_{7-2000}$ aryl ester)$_{1-100}$-, —($C_{7-2000}$ alkylaryl ester)$_{1-100}$-, —($C_{8-2000}$ arylalkyl ester)$_{1-100}$-, —$R^a$—CO—O—($C_{1-30}$ alkyl ether)$_{1-100}$-, —$R^a$—CO—O—($C_{6-40}$ aryl ether)$_{1-100}$-, —$R^a$—CO—O—($C_{7-2000}$ alkylaryl ether)$_{1-100}$-, —$R^a$—CO—O—($C_{7-2000}$ arylalkyl ether)$_{1-100}$-, —($C_{4-50}$ alkyl urethane)$_{1-100}$-, —($C_{14-60}$ aryl urethane)$_{1-100}$-, —($C_{10-2000}$ alkylaryl urethane)$_{1-100}$-, —($C_{10-2000}$ arylalkyl urethane)$_{1-100}$-, —($C_{5-50}$ alkyl urea)$_{1-100}$-, —($C_{14-60}$ aryl urea)$_{1-100}$-, —($C_{10-2000}$ alkylaryl urea)$_{1-100}$-, —($C_{10-2000}$ arylalkyl urea)$_{1-100}$-, —($C_{2-50}$ alkyl amide)$_{1-100}$-, —($C_{7-60}$ aryl amide)$_{1-100}$-, —($C_{8-2000}$ alkylaryl amide)$_{1-100}$-, —($C_{8-2000}$ arylalkyl amide)$_{1-100}$-, —($C_{3-30}$ alkyl anhydride)$_{1-100}$-, —($C_{8-50}$ aryl anhydride)$_{1-100}$-, —($C_{9-2000}$ alkylaryl anhydride)$_{1-100}$-, —($C_{9-2000}$ arylalkyl anhydride)$_{1-100}$-, —($C_{2-30}$ alkylcarbonate)$_{1-100}$-, —($C_{7-50}$ aryl carbonate)$_{1-100}$-, —($C_{8-2000}$ alkylaryl carbonate)$_{1-100}$-, —($C_{8-2000}$ arylalkyl carbonate)$_{1-100}$-, —$R^a$—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$-, —$R^a$—O—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$-, —$R^a$—O—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$-CO—NH—($R^b$ or Ar—$R^b$—Ar)—NH—CO—O—, —$R^a$—O—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$-$R^c$—O—CO—NH—($R^b$ or Ar—$R^b$—Ar)—NH—CO—O—, —$R^a$—NH—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$-, —$R^a$—NH—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$-, —$R^a$—NH—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$-CO—NH—($R^b$ or Ar—$R^b$—Ar)—NH—CO—O—, —$R^a$—NH—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$-, —$R^a$—O—CO—NH—($R^b$ or Ar—$R^b$—Ar)—NH—CO—O—, —$R^a$—O—CO—NH—($R^b$ or Ar—$R^b$—Ar)—NH—CO—NH—($C_{2-50}$ alkyl amide, $C_{7-60}$ aryl amide, $C_{8-2000}$ alkylaryl amide, or $C_{8-2000}$ arylalkyl amide)$_{1-100}$-, —$R^a$—NH—CO—NH—($R^b$ or Ar—$R^b$—Ar)—NH—CO—NH—($C_{2-50}$ alkyl amide, $C_{7-60}$ aryl amide, $C_{8-2000}$ alkylaryl amide, or $C_{8-2000}$ arylalkyl amide)$_{1-100}$-, —$CH_2$—CH(OH)—$CH_2$—($OCH_2CH_2$)$_{1-100}$—$OCH_2$CH(OH)—$CH_2$, —$CH_2$—CH(OH)—$CH_2$—$N^+HR^a$—($CH_2CH_2N^+R^aR^b$)$_{1-100}$—$CH_2CH_2N^+HR^a$—$CH_2$CH(OH)$CH_2$—, or —$CH_2CH_2$—$N^+R^aR^b$—($CH_2CH_2N^+R^aR^b$)$_{1-100}$—$R^c$—; and each Z, independently, is —$R^a$—, —$R^a$—Ar—, —Ar—$R^a$—, or —Ar; and $V_1$ and $V_2$ independently are —OH, —SH, —$NH_2$, —NHOH, —$SO_3H$, —$OSO_3H$, —$CO_2H$, —$CONH_2$, —$CONHNH_2$, —CH($NH_2$)—$CO_2H$, —NH—$CH_2$—$CO_2H$, —P(OH)$_3$, —PO(OH)$_2$, —O—PO(OH)$_2$, —O—PO(OH)—O—PO(OH)$_2$, —O—PO($O^-$)—O—$CH_2CH_2NH_3^+$, —O—PO($O^-$)—O—$CH_2CH_2$—$N^+$($CH_3$)$_3$, -glycoside, -oligosaccharide, —CO-glycoside, —CO-oligosaccharide, —$OCH_3$, —$OCH_2$(CHOH)$_4$—$CH_2OH$, —$OCH_2$(CHOH)$_2$—$CH_2OH$, —CO—$OCH_2$(CHOH)$_4$—$CH_2OH$, —$C_6H_3$(OH)$_2$, —N($CH_2CO_2H$)$_2$, —CO—N($CH_2CO_2H$)$_2$, —CO—NH—C($CH_2CH_2CO_2H$)$_3$, —CO—NH—C($CH_2CH_2OH$)$_3$, $—[CH_2—CH(CO_2R^a)]_{1-100}—H$, $—O—(CH_2CH_2O)_{1-100}—H$, $—NH_3^+$, $—N^+H_2R^a$, $—N^+HR^aR^b$, or $—N^+R^aR^bR^c$;

wherein each of $R^a$, $R^b$, and $R^c$ are each independently $C_{1-20}$ linear or branched alkyl;

Ar is aryl;

W is hydroxyl or amino;

p and s each independently is 0-20; and r and q each independently is 0 or 1.

In another aspect, included herein are pharmaceutical compositions comprising the foregoing $C_{60/70}$PS-CB-Abx compounds.

In yet another aspect, a method of photodynamic therapy comprises applying the foregoing pharmaceutical composition to a site on the skin of a subject and exposing the site of application on the skin to visible light for excitation of the $C_{60/70}$PS-CB-Abx compound.

In yet another aspect, a method of photodynamic therapy comprises administering the foregoing composition to a site of disease in a subject and exposing the site of administration to visible light for excitation of the $C_{60/70}$PS-CB-Abx compound.

In another aspect, a nano-$C_{60/70}$PS compound has the following formula (II):

(II)

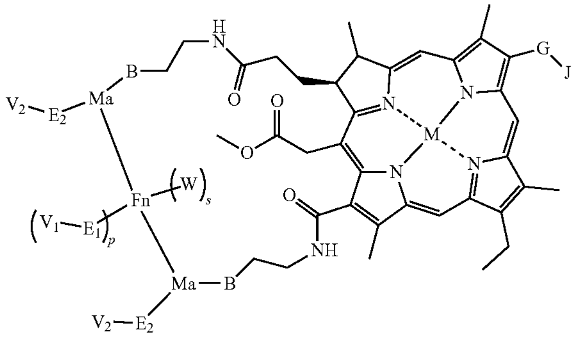

wherein

Fn is a fullerene core;

M is a metal ion;

B is amino-$C_{2-200}$ alkyl ether, amino-$C_{2-200}$ alkyl, hydroxy-$C_{2-200}$ alkyl ether, or hydroxy-$C_{2-200}$ alkyl;

Ma is —NH—CO-cyclopropanyl-CO— or —O—CO-cyclopropanyl-CO—;

K is —CH═CH—, $—CH(O—V_2)—CH_2—$ or $—CH(O—CO—Z—V_2)—CH_2—$;

L is —H or $-E_3-V_2$;

$E_1$, $E_2$, and $E_3$ are each independently $Y_1$,$Y_2$-amino, ($Y_1$,$Y_2$-alkyl)-amino, $Y_1$,$Y_2$-ethylenediamino, (dihydroxymethyl)alkylamino, ($X_1$,$X_3$-aryl)amino, $X_1$,$X_3$-aryloxy, $Y_2$-alkoxy, $Y_1$,$Y_2$-alkoxy, ($Y_1$,$Y_2$-amino)alkoxy, ($Y_1$,$Y_2$,$Y_3$-aryl)oxy, (dihydroxyalkyl)-aryloxy, ($Y_1$,$Y_2$,$Y_3$-alkyl)amino, ($Y_1$,$Y_2$,$Y_3$-aryl)amino, dihydroxyalkylamino, $Y_1$,$Y_2$,$Y_3$-alkoxy, (trihydroxyalkyl)alkoxy, (trihydroxyalkyl)alkylamino, (dicarboxyalkyl)amino, $Y_2$-thio, ($Y_1$,$Y_2$,$Y_3$-alkyl)thio, ($X_1$,$X_3$-aryl)thio, ($Y_1$,$Y_2$-alkyl)thio, (dihydroxyalkyl)thio, $Y_1$,$Y_2$-dioxoalkyl, tri-($Y_1$,$Y_2$,$Y_3$-methylaminocarboxyethyl)methylamino, ((glycosidyl)oxoheteroaryl)amino, ((glycosidyl)oxoaryl)amino, ($X_1$,$X_2$,$X_3$-heteroaryl)amino, ($X_1$-diarylketone)amino, (T,$X_1$-oxoaryl)amino, (T,$X_1$-dioxoaryl)amino, ($Y_1$-alkyl,$Y_2$-alkyldioxoheteroaryl)amino, ($Y_1$-alkyl,$Y_2$-alkyldioxoaryl)amino, (di($Y_1$,$Y_2$-methyl)dioxoheteroaryl)amino, (di($Y_1$,$Y_2$-methyl)dioxoaryl)amino, ((glycosidyl)heteroaryl)amino, ((glycosidyl)aryl)amino, ((carboxylacetylalkyl)oxo-heteroaryl)amino, ((carboxylacetylalkyl)oxoaryl)amino, ((isopropylaminohydroxy-alkoxy)aryl)amino, ($X_1$,$X_2$,$X_3$-alkylaryl)amino, ($X_1$,$X_2$,$X_3$-heteroaryl)oxy, (isopropylaminohydroxyalkyl)aryloxy, ($X_1$,$X_2$,$X_3$-oxoheteroaryl)oxy, ($X_1$,$X_2$,$X_3$-oxoaryl)oxy, ($X_1$,$Y_1$-oxoheteroaryl)oxy, ($X_1$-diarylketone)oxy, (T,$X_1$-oxoaryl)oxy, ($X_1$,$X_2$-dioxoaryl)oxy, ($Y_1$,$Y_2$,di-aminodihydroxy)alkyl, ($X_1$,$X_2$-heteroaryl)thio, ((tricarboxylalkyl)ethylene-diamino)alkoxy, ($X_1$,$X_2$-oxoaryl)thio, ($X_1$,$X_2$-dioxoaryl)thio, (glycosidylheteroaryl)thio, (glycosidylaryl)thio, $Y_1$-alkyl(thiocarbonyl)thio, $Y_1$,$Y_2$,-alkyl(thiocarbonyl)thio, $Y_1$,$Y_2$,$Y_3$-alkyl(thiocarbonyl)thio, ($Y_1$,$Y_2$-aminothiocarbonyl)thio, (pyranosyl)thio, cysteinyl, tyrosinyl, (phenylalaninyl)amino, (dicarboxyalkyl)thio, (aminoaryl)$_{1-100}$amino, (pyranosyl)$_{1-100}$amino, ($Y_1$-aminoaryl)$_{1-100}$amino, (amino(sulfoaryl))$_{1-100}$amino, peptidyl, thymidinyl, uridinyl, guanosinyl, adenosinyl, cholesteryl, or biotinylalkoxy; wherein T is halo;

each of $X_1$, $X_2$, and $X_3$ is each independently $—Y_2$, $—O—Y_2$, $—S—Y_2$, $—NH—Y_2$, $—CO—O—Y_2$, $—O—CO—Y_2$, $—CO—NH—Y_2$, $—CO—NY_1Y_2$, $—NH—CO—Y_2$, $—SO_2—Y_2$, $—SO_2—O—Y_2$, $—CHY_1Y_2$, or $—NY_1Y_2$;

each of $Y_1$, $Y_2$, and $Y_3$ is each independently —H, -Q-Z—H or —Z—H; in which each Q, independently, is $—R^a—O—[Si(CH_3)_2—O—]_{1-100}$-, $—C_{1-2000}$ alkyl-, $—C_{6-40}$ aryl-, $—C_{7-2000}$ alkylaryl-, $—C_{7-2000}$ arylalkyl-, $—(C_{1-30}$ alkyl ether$)_{1-100}$-, $—(C_{6-40}$ aryl ether$)_{1-100}$-, $—(C_{7-2000}$ alkylaryl ether$)_{1-100}$-, $—(C_{7-2000}$ arylalkyl ether$)_{1-100}$-, $—(C_{1-30}$ alkyl thioether$)_{1-100}$-, $—(C_{6-40}$ aryl thioether$)_{1-100}$-, $—(C_{7-2000}$ alkylaryl thioether$)_{1-100}$-, $—(C_{7-2000}$ arylalkyl thioether$)_{1-100}$-, $—(C_{2-50}$ alkyl ester$)_{1-100}$-, $—(C_{7-2000}$ aryl ester$)_{1-100}$-, $—(C_{8-2000}$ alkylaryl ester$)_{1-100}$-, $—(C_{8-2000}$ arylalkyl ester$)_{1-100}$-, $—R^a—CO—O—(C_{1-30}$ alkyl ether$)_{1-100}$-, $—R^a—CO—O—(C_{6-40}$ aryl ether$)_{1-100}$-, $—R^a—CO—O—(C_{7-2000}$ alkylaryl ether$)_{1-100}$-, $—R^a—CO—O—(C_{7-2000}$ arylalkyl ether$)_{1-100}$-, $—(C_{4-50}$ alkyl urethane$)_{1-100}$-, $—(C_{14-60}$ aryl urethane$)_{1-100}$-, $—(C_{10-2000}$ alkylaryl urethane$)_{1-100}$-, $—(C_{10-2000}$ arylalkyl urethane$)_{1-100}$-, $—(C_{5-50}$ alkyl urea$)_{1-100}$-, $—(C_{14-60}$ aryl urea$)_{1-100}$-, $—(C_{10-2000}$ alkylaryl urea$)_{1-100}$-, $—(C_{10-2000}$ arylalkyl urea$)_{1-100}$-, $—(C_{2-50}$ alkyl amide$)_{1-100}$-, $—(C_{7-60}$ aryl amide$)_{1-100}$-, $—(C_{8-2000}$ alkylaryl amide$)_{1-100}$-, $—(C_{8-2000}$ arylalkyl amide$)_{1-100}$-, $—(C_{3-30}$ alkyl anhydride$)_{1-100}$-, $—(C_{8-50}$ aryl anhydride$)_{1-100}$-, $—(C_{9-2000}$ alkylaryl anhydride$)_{1-100}$-, $—(C_{9-2000}$ arylalkyl anhydride$)_{1-100}$-, $—(C_{2-30}$ alkylcarbonate$)_{1-100}$-, $—(C_{7-50}$ aryl carbonate$)_{1-100}$-, $—(C_{8-2000}$ alkylaryl carbonate$)_{1-100}$-, $—(C_{8-2000}$ arylalkyl carbonate$)_{1-100}$-, $—R^a—CO—NH—(R^b$ or $Ar—R^b—Ar)—NH—CO—O—(C_{1-30}$ alkyl ether, $C_{6-40}$ aryl ether, $C_{7-2000}$ alkylaryl ether, or $C_{7-2000}$ arylalkyl ether$)_{1-100}$-, $—R^a—O—CO—NH—(R^b$ or $Ar—R^b—Ar)—NH—CO—O—(C_{2-50}$ alkyl ester, $C_{7-60}$ aryl ester, $C_{8-2000}$ alkylaryl ester, or $C_{8-2000}$ arylalkyl ester$)_{1-100}$-, $—R^a—O—CO—NH—(R^b$ or $Ar—R^b—Ar)—NH—CO—O—(C_{1-30}$ alkyl ether, $C_{6-40}$ aryl ether, $C_{7-2000}$ alkylaryl ether, or $C_{7-2000}$ arylalkyl ether$)_{1-100}$-CO—NH—$(R^b$ or $Ar—R^b—Ar)—NH—CO—O—$, $—R^a—O—CO—NH—(R^b$ or $Ar—R^b—Ar)—NH—CO—O—(C_{2-50}$ alkyl ester, $C_{7-60}$ aryl ester, $C_{8-2000}$ alkylaryl ester, or $C_{8-2000}$ arylalkyl ester)$_{1-100}$-$R^c$—O—CO—NH—($R^b$ or Ar—$R^b$—Ar)—NH—CO—O—, —$R^a$—NH—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$-, —$R^a$—NH—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$-, —$R^a$—NH—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$-CO—NH—($R^b$ or Ar—$R^b$—Ar)—NH—CO—O—, —$R^a$—NH—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$-, —$R^a$—O—CO—NH—($R^b$ or Ar—$R^b$—Ar)—NH—CO—O—, —$R^a$—O—CO—NH—($R^b$ or Ar—$R^b$—Ar)—NH—CO—NH—($C_{2-50}$ alkyl amide, $C_{7-60}$ aryl amide, $C_{8-2000}$ alkylaryl amide, or $C_{8-2000}$ arylalkyl amide)$_{1-100}$-, —$R^a$—NH—CO—NH—($R^b$ or Ar—$R^b$—Ar)—NH—CO—NH—($C_{2-50}$ alkyl amide, $C_{7-60}$ aryl amide, $C_{8-2000}$ alkylaryl amide, or $C_{8-2000}$ arylalkyl amide)$_{1-100}$-, —$CH_2$—CH(OH)—$CH_2$—$(OCH_2CH_2)_{1-100}$—$OCH_2CH(OH)$—$CH_2$, —$CH_2$—CH(OH)—$CH_2$—$N^+HR^a$—$(CH_2CH_2N^+R^aR^b)_{1-100}$—$CH_2CH_2N^+HR^a$—$CH_2CH(OH)CH_2$—, or —$CH_2CH_2$—$N^+R^aR^b$—$(CH_2CH_2N^+R^aR^b)_{1-100}$—$R^c$—; and each Z, independently, is —$R^a$—, —$R^a$—Ar—, —Ar—$R^a$—, or —Ar—; and $V_1$ and $V_2$ independently are —OH, —SH, —$NH_2$, —NHOH, —$SO_3H$, —$OSO_3H$, —$CO_2H$, —$CONH_2$, —$CONHNH_2$, —$CH(NH_2)$—$CO_2H$, —NH—$CH_2$—$CO_2H$, —$P(OH)_3$, —$PO(OH)_2$, —O—$PO(OH)_2$, —O—PO(OH)—O—$PO(OH)_2$, —O—$PO(O^-)$—O—$CH_2CH_2NH_3^+$, —O—$PO(O^-)$—O—$CH_2CH_2$—$N^+(CH_3)_3$, -glycoside, -oligosaccharide, —CO-glycoside, —CO-oligosaccharide, —$OCH_3$, —$OCH_2(CHOH)_4$—$CH_2OH$, —$OCH_2(CHOH)_2$—$CH_2OH$, —CO—$OCH_2(CHOH)_4$—$CH_2OH$, —$C_6H_3(OH)_2$, —$N(CH_2CO_2H)_2$, —CO—$N(CH_2CO_2H)_2$, —CO—NH—$C(CH_2CH_2CO_2H)_3$, —CO—NH—$C(CH_2CH_2OH)_3$, —$[CH_2$—$CH(CO_2R^a)]_{1-100}$—H, —O—$(CH_2CH_2O)_{1-100}$—H, —$NH_3^+$, —$N^+H_2R^a$, —$N^+HR^aR^b$, or —$N^+R^aR^bR^c$;

wherein each of $R^a$, $R^b$, and $R^c$ are each independently $C_{1-20}$ linear or branched alkyl;

Ar is aryl;

W is hydroxyl or amino;

p and s each independently is 0-20; and

In another aspect, also included is a nano-$C_{60/70}$PS compound of the following formula (III):

wherein

Fn is a fullerene core;

U is —CO— or —[C═C(CN)$_2$]—;

$A_1$ and $A_2$ are each independently —$P_1$—$P_2$;

$P_1$ is —$C_{2-200}$ alkyl-(CO)—, —$C_{2-200}$ alkyl ether-(CO)—, —$C_{2-200}$ alkylaryl-(CO)—, or —$C_{2-200}$ alkylaryl ether-(CO)—; and $P_2$ is —NH—$C_{2-50}$ alkyl-$(OCH_2CH_2)_{1-100}$—$R^{cf}$, —O—$C_{2-50}$ alkyl-$(OCH_2CH_2)_{1-100}$—$R^{cf}$, —NH—$C_{2-50}$ alkyl-$N^+R^{ad}R^{be}$—$(CH_2CH_2N^+R^{ad}R^{be})_{1-100}$—$R^{cf}$, or —O—$C_{2-50}$ alky-$N^+R^{ad}R^{be}$—$(CH_2CH_2N^+R^{ad}R^{be})_{1-100}$—$R^{cf}$; wherein each of $R^{ad}$, $R^{be}$, and $R^{cf}$ are each independently —H or —$C_{1-20}$ linear or branched alkyl;

$E_1$ is $Y_1$,$Y_2$-amino, ($Y_1$,$Y_2$-alkyl)-amino, $Y_1$,$Y_2$-ethylenediamino, (dihydroxymethyl)alkylamino, ($X_1$,$X_3$-aryl)amino, $X_1$,$X_3$-aryloxy, $Y_2$-alkoxy, $Y_1$,$Y_2$-alkoxy, ($Y_1$,$Y_2$-amino)alkoxy, ($Y_1$,$Y_2$,$Y_3$-aryl)oxy, (dihydroxyalkyl)-aryloxy, ($Y_1$,$Y_2$,$Y_3$-alkyl)amino, ($Y_1$,$Y_2$,$Y_3$-aryl)amino, dihydroxyalkylamino, $Y_1$,$Y_2$,$Y_3$-alkoxy, (trihydroxyalkyl)alkoxy, (trihydroxyalkyl)alkylamino, (dicarboxyalkyl)amino, $Y_2$-thio, ($Y_1$,$Y_2$,$Y_3$-alkyl)thio, ($X_1$,$X_3$-aryl)thio, ($Y_1$,$Y_2$-alkyl)thio, (dihydroxyalkyl)thio, $Y_1$,$Y_2$-dioxoalkyl, tri-($Y_1$,$Y_2$,$Y_3$-methylaminocarboxyethyl)methylamino, ((glycosidyl)oxoheteroaryl)amino, ((glycosidyl)oxoaryl)amino, ($X_1$,$X_2$,$X_3$-heteroaryl)amino, ($X_1$-diarylketone)amino, (T,$X_1$-oxoaryl)amino, (T,$X_1$-dioxoaryl)amino, ($Y_1$-alkyl,$Y_2$-alkyldioxoheteroaryl)amino, ($Y_1$-alkyl, $Y_2$-alkyldioxoaryl)amino, (di($Y_1$,$Y_2$-methyl)dioxoheteroaryl)amino, (di($Y_1$,$Y_2$-methyl)dioxoaryl)amino, ((glycosidyl)heteroaryl)amino, ((glycosidyl)aryl)amino, ((carboxylacetylalkyl)oxo-heteroaryl)amino, ((carboxylacetylalkyl)oxoaryl)amino, ((isopropylaminohydroxy-alkoxy)aryl)amino, ($X_1$,$X_2$,$X_3$-alkylaryl)amino, ($X_1$,$X_2$,$X_3$-heteroaryl)oxy, (isopropylaminohydroxyalkyl)aryloxy, ($X_1$,$X_2$,$X_3$-oxoheteroaryl)oxy, ($X_1$,$X_2$,$X_3$-oxoaryl)oxy, ($X_1$,$Y_1$-oxoheteroaryl)oxy, ($X_1$-diarylketone)oxy, (T,$X_1$-oxoaryl)oxy, ($X_1$,$X_2$-dioxoaryl)oxy, ($Y_1$,$Y_2$,di-aminodihydroxy)alkyl, ($X_1$,$X_2$-heteroaryl)thio, ((tricarboxylalkyl)ethylene-diamino)alkoxy, ($X_1$,$X_2$-oxoaryl)thio, ($X_1$,$X_2$-dioxoaryl)thio, (glycosidylheteroaryl)thio, (glycosidylaryl)thio, $Y_1$-alkyl(thiocarbonyl)thio, $Y_1$,$Y_2$,-alkyl(thiocarbonyl)thio, $Y_1$,$Y_2$,$Y_3$-alkyl(thiocarbonyl)thio, ($Y_1$,$Y_2$-aminothiocarbonyl)thio, (pyranosyl)thio, cysteinyl, tyrosinyl, (phenylalaninyl)amino, (dicarboxyalkyl)thio, (aminoaryl)$_{1-100}$amino, (pyranosyl)$_{1-100}$amino, ($Y_1$-amino- (III)

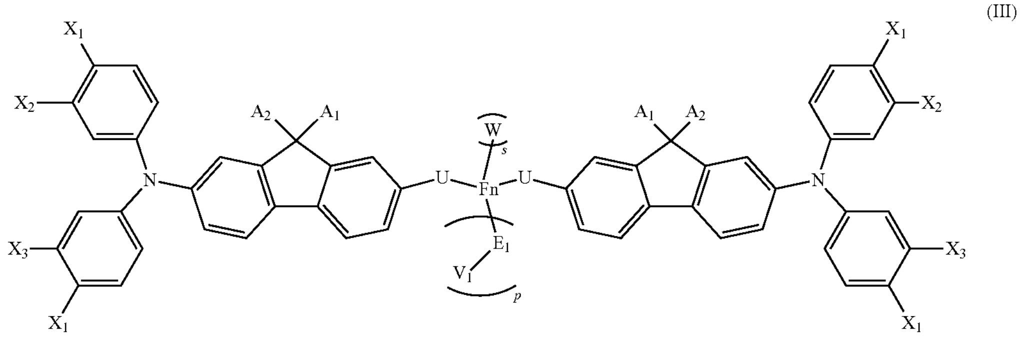

aryl)$_{1-100}$amino, (amino(sulfoaryl))$_{1-100}$amino, peptidyl, thymidinyl, uridinyl, guanosinyl, adenosinyl, cholesteryl, or biotinylalkoxy; wherein T is halo;

each of $X_1$, $X_2$, and $X_3$ is each independently —$Y_2$, —O—$Y_2$, —S—$Y_2$, —NH—$Y_2$, —CO—O—$Y_2$, —O—CO—$Y_2$, —CO—NH—$Y_2$, —CO—$NY_1Y_2$, —NH—CO—$Y_2$, —$SO_2$—$Y_2$, —$SO_2$—O—$Y_2$, —$CHY_1Y_2$, or —$NY_1Y_2$;

each of $Y_1$, $Y_2$, and $Y_3$ is each independently —H, -Q-Z—H or —Z—H; in which each Q, independently, is —$R^a$—O—[Si($CH_3$)$_2$—O—]$_{1-100}$-, —$C_{1-2000}$ alkyl-, —$C_{6-40}$ aryl-, —$C_{7-2000}$ alkylaryl-, —$C_{7-2000}$ arylalkyl-, —($C_{1-30}$ alkyl ether)$_{1-100}$-, —($C_{6-40}$ aryl ether)$_{1-100}$-, —($C_{7-2000}$ alkylaryl ether)$_{1-100}$-, —($C_{7-2000}$ arylalkyl ether)$_{1-100}$-, —($C_{1-30}$ alkyl thioether)$_{1-100}$-, —($C_{6-40}$ aryl thioether)$_{1-100}$-, —($C_{7-2000}$ alkylaryl thioether)$_{1-100}$-, —($C_{7-2000}$ arylalkyl thioether)$_{1-100}$-, —($C_{2-50}$ alkyl ester)$_{1-100}$-, —($C_{7-2000}$ aryl ester)$_{1-100}$-, —($C_{8-2000}$ alkylaryl ester)$_{1-100}$-, —($C_{8-2000}$ arylalkyl ester)$_{1-100}$-, —$R^a$—CO—O—($C_{1-30}$ alkyl ether)$_{1-100}$-, —$R^a$—CO—O—($C_{6-40}$ aryl ether)$_{1-100}$-, —$R^a$—CO—O—($C_{7-2000}$ alkylaryl ether)$_{1-100}$-, —$R^a$—CO—O—($C_{7-2000}$ arylalkyl ether)$_{1-100}$-, —($C_{4-50}$ alkyl urethane)$_{1-100}$-, —($C_{14-60}$ aryl urethane)$_{1-100}$-, —($C_{10-2000}$ alkylaryl urethane)$_{1-100}$-, —($C_{10-2000}$ arylalkyl urethane)$_{1-100}$-, —($C_{5-50}$ alkyl urea)$_{1-100}$-, —($C_{14-60}$ aryl urea)$_{1-100}$-, —($C_{10-2000}$ alkylaryl urea)$_{1-100}$-, —($C_{10-2000}$ arylalkyl urea)$_{1-100}$-, —($C_{2-50}$ alkyl amide)$_{1-100}$-, —($C_{7-60}$ aryl amide)$_{1-100}$-, —($C_{8-2000}$ alkylaryl amide)$_{1-100}$-, —($C_{8-2000}$ arylalkyl amide)$_{1-100}$-, —($C_{3-30}$ alkyl anhydride)$_{1-100}$-, —($C_{8-50}$ aryl anhydride)$_{1-100}$-, —($C_{9-2000}$ alkylaryl anhydride)$_{1-100}$-, —($C_{9-2000}$ arylalkyl anhydride)$_{1-100}$-, —($C_{2-30}$ alkylcarbonate)$_{1-100}$-, —($C_{7-50}$ aryl carbonate)$_{1-100}$-, —($C_{8-2000}$ alkylaryl carbonate)$_{1-100}$-, —($C_{8-2000}$ arylalkyl carbonate)$_{1-100}$-, —$R^a$—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$-, —$R^a$—O—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$-, —$R^a$—O—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$-CO—NH—($R^b$ or Ar—$R^b$—Ar)—NH—CO—O—, —$R^a$—O—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$-$R^c$—O—CO—NH—($R^b$ or Ar—$R^b$—Ar)—NH—CO—O—, —$R^a$—NH—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$-, —$R^a$—NH—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$-, —$R^a$—NH—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$-CO—NH—($R^b$ or Ar—$R^b$—Ar)—NH—CO—O—, —$R^a$—NH—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$-, —$R^a$—O—CO—NH—($R^b$ or Ar—$R^b$—Ar)—NH—CO—O—, —$R^a$—O—CO—NH—($R^b$ or Ar—$R^b$—Ar)—NH—CO—NH—($C_{2-50}$ alkyl amide, $C_{7-60}$ aryl amide, $C_{8-2000}$ alkylaryl amide, or $C_{8-2000}$ arylalkyl amide)$_{1-100}$-, —$R^a$—NH—CO—NH—($R^b$ or Ar—$R^b$—Ar)—NH—CO—NH—($C_{2-50}$ alkyl amide, $C_{7-60}$ aryl amide, $C_{8-2000}$ alkylaryl amide, or $C_{8-2000}$ arylalkyl amide)$_{1-100}$-, —$CH_2$—CH(OH)—$CH_2$—($OCH_2CH_2$)$_{1-100}$—$OCH_2$CH(OH)—$CH_2$, —$CH_2$—CH(OH)—$CH_2$—$N^+HR^a$—($CH_2CH_2N^+R^aR^b$)$_{1-100}$—$CH_2CH_2N^+HR^a$—$CH_2$CH(OH)$CH_2$—, or —$CH_2CH_2$—$N^+R^aR^b$—($CH_2CH_2N^+R^aR^b$)$_{1-100}$—$R^c$—; and each Z, independently, is —$R^a$—, —$R^a$—Ar—, —Ar—$R^a$—, or —Ar—; and $V_1$ and $V_2$ independently are —OH, —SH, —$NH_2$, —NHOH, —$SO_3H$, —$OSO_3H$, —$CO_2H$, —$CONH_2$, —$CONHNH_2$, —CH($NH_2$)—$CO_2H$, —NH—$CH_2$—$CO_2H$, —P$(OH)_3$, —PO$(OH)_2$, —O—PO$(OH)_2$, —O—PO(OH)—O—PO$(OH)_2$, —O—PO($O^-$)—O—$CH_2CH_2NH_3^+$, —O—PO($O^-$)—O—$CH_2CH_2$—$N^+(CH_3)_3$, -glycoside, -oligosaccharide, —CO-glycoside, —CO-oligosaccharide, —$OCH_3$, —$OCH_2(CHOH)_4$—$CH_2OH$, —$OCH_2(CHOH)_2$—$CH_2OH$, —CO—$OCH_2(CHOH)_4$—$CH_2OH$, —$C_6H_3(OH)_2$, —N$(CH_2CO_2H)_2$, —CO—N$(CH_2CO_2H)_2$, —CO—NH—C$(CH_2CH_2CO_2H)_3$, —CO—NH—C$(CH_2CH_2OH)_3$, —[$CH_2$—CH($CO_2R^a$)]$_{1-100}$—H, —O—($CH_2CH_2O$)$_{1-100}$—H, —$NH_3^+$, —$N^+H_2R^a$, —$N^+HR^aR^b$, or —$N^+R^aR^bR^c$;

wherein each of $R^a$, $R^b$, and $R^c$ are each independently $C_{1-20}$ linear or branched alkyl;

Ar is aryl;

W is hydroxyl or amino;

p and s each independently is 0-20; and wherein each of $R^a$, $R^b$, and $R^c$ are each independently —$C_{1-20}$ linear or branched alkyl;

wherein Ar is aryl;

W is hydroxyl or amino;

and s each independently is 0-20.

In another aspect, included herein are pharmaceutical compositions comprising the foregoing nano-$C_{60/70}$PS compounds.

In yet another aspect, a method of photodynamic therapy comprises applying the foregoing pharmaceutical composition to a site on the skin of a subject and exposing the site of application on the skin to visible light for excitation of the nano-$C_{60/70}$PS compound.

In yet another aspect, a method of photodynamic therapy comprises administering the foregoing composition to a site of disease in a subject and exposing the site of administration to visible light for excitation of the nano-$C_{60/70}$PS compound.

Figure 1A:
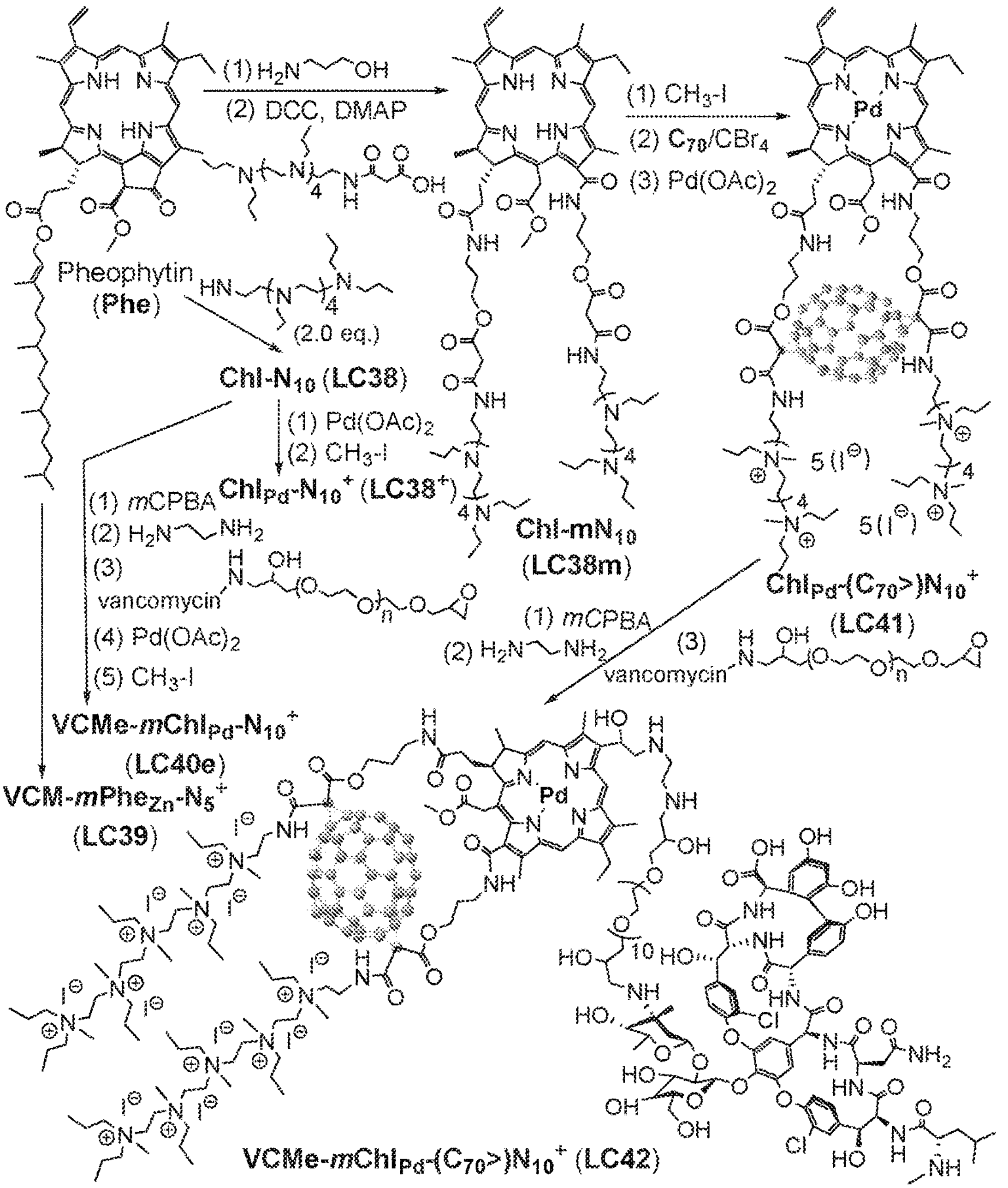
FIGS. 1A and 1B. Synthetic scheme and the structures of $Chl_{pd}$-$N_{10}^+$ (LC38$^+$), $Chl_{pd}$-($C_{70}$>)$N_{10}$+(LC41), and covalent vancomycin conjugates VCMe-m$Chl_{pd}$-$N_{10}^+$ (LC40e) and VCMe-m$Chl_{pd}$-($C_{70}$>)$N_{10}^+$ (LC42) as new either aPDT, nano-$C_{60/70}$-aPDT, or $C_{60/70}$-aPDT-CB-Abx drugs.

650-nm laser, (e) white LED, and (f) 400-nm LED light, as the background reference for comparison.

FIG. 3. (A) aPDT against vancomycin-resistant and sensitive strains of *E. fecium* (VSE). $Log_{10}$ survival fractions of *E. fecium* ($10^8$ cells/mL) incubated for 30 min with 50-nM concentration of VCM-mPhe$_{Zn}$-$N_5^+$ (LC39, see Huang, L., Wang, M., Chiang, L. Y., Hamblin, M. R., et al. *Photochem. Photobiol. Sci.* 2018, 17, 638-651) by irradiation with increasing exposes of a 415-nm LED light. (B) Concentration dependent aPDI of *A. baumannii* (AF0004) by VCMe-mChl$_{Pd}$-$N_{10}^+$ (LC40e, 12.5 μM) upon illumination at a red wavelength (660 nm, 40 mW/$cm^2$) with the fluence of 115 J/$cm^2$. (C) and (D) were in vitro aPDI activities of (a) vancomycin alone, (b) LC37, (c) LC38⁺, and (d) LC40e on planktonic methicillin-resistant *Staphylococcus aureus* (MRSA, strain IQ0064) cells under the aPDI agent concentration up to 20 μM. Irradiation was carried out with (C) the radiant exposure of 115 J/$cm^2$ at 660 nm (LED light, 40 mW/$cm^2$) and (D) the radiant exposure of 20 J/$cm^2$ at 405 nm (LED light, 24 mW/$cm^2$). All data were represented as login survival fractions as a function of both aPDI agent concentration and light wavelength/exposure, where the dashed red line in Panel Cd represents the detection limit of MRSA CFU. Human epithelial keratinocyte HaCaT cells were also included in the Figure, under the same experimental conditions, for the demonstration of low aPDI-derived photocytotoxicity to host human cells with the data in (e). (E) Concentration dependent aPDI of MRSA (strain IQ0064) by Chl$_{Pd}$-($C_{70}$>)$N_{10}^+$ (LC41) upon illumination at 115 J/$cm^2$ and 660-nm wavelength (40 mW/$cm^2$).

The above-described and other features will be appreciated and understood by those skilled in the art from the following detailed description, drawings, and appended claims.

DETAILED DESCRIPTION

Described herein are $C_{60/70}$PS-CB-Abx compounds comprising a fullerenyl mesochlorin photosensitizer with covalently bound antibiotics. The compounds and compositions described herein show combined therapeutic effects of photodynamic and antibiotic cytotoxicities. Also described is the nano-$C_{60/70}$PS analogous compounds comprising a fullerenyl chlorin photosensitizer without covalently bound antibiotics. Also disclosed are methods for preparing these nano-$C_{60/70}$PS compounds and $C_{60/70}$PS-CB-Abx conjugates. In addition, the compounds and compositions exhibit improved bacterial cell targeting ability and enhanced photodynamic pathogen killing by the increase of photoinduced radical and electron-based reactive oxygen species (ROS) production.

There is a critical need for the development of alternative therapeutics to tackle antibiotic resistance of pathogenic bacteria. Described herein is a combinatorial antimicrobial therapy using new water-soluble cyclopropyl-functionalized spherical nanocarbon-cage fullerenyl photosensitizers (nano-$C_{60/70}$PSs) mediated antimicrobial photodynamic therapy (aPDT) with clinically used antibiotics for localized infections and address the serious problem of emerging antibiotic-resistant bacteria. In contrast to common combination therapies by delivering antibiotics separately, this disclosure provides covalently conjugate antibiotics with nano-$C_{60/70}$PSs, leading to controlled concurrent delivery of nano-$C_{60/70}$PSs and covalently-bonded targetable antibiotics to infection sites.

More specifically, the compositions described herein comprise ultrafast photoactive, deca- to icosa-cationic nano-$C_{60/70}$PSs with light-harvesting antenna as nano-aPDT agents, based on Type-I and new Type-III (transferrable electron ($e^-$)-based) photochemical mechanism. These new water-soluble nano-$C_{60/70}$PSs exhibit high efficiency in production of ROS. The antibacterial capability is added by antibiotics with their ability to target bacteria on each nano-$C_{60/70}$PS, by covalent conjugation of structural moieties together into one nanostructure. Accordingly, combinatorial antimicrobial therapy can be performed by controlled concurrent delivery of nano-$C_{60/70}$PSs for nano-$C_{60/70}$-aPDT and covalently-bonded antibiotics for $C_{60/70}$-aPDT-CB-Abx aPDT to enhance the antimicrobial effect.

Infections with multidrug-resistant (MDR) microbes are considered an emerging threat to public health throughout the world, and are responsible for significant morbidity and mortality with these once common diseases. There is a problem with the relatively rapid acquisition of antibiotic resistance by bacteria and few antibiotics with new mechanisms of action in the pipeline. Therefore, the outcome significantly reduces the chance of effectively treating infections particularly when a microorganism, such as bacteria, fungi, viruses, and parasites, transforms by a genetic mutation making it resistant to the inhibiting effect of one or more antimicrobial agents that were formerly effectively functioning. This leads to inefficient treatment resulting in persistence of illness and spreading of infections. Indeed, some strains, such as methicillin-resistant *Staphylococcus aureus* (MRSA), are resistant not only to methicillin but also resistant to essentially all of commonly available agents. One of the most promising alternative approaches in this respect is the antimicrobial photodynamic inactivation (aPDI) and the associated photodynamic therapy (aPDT).

Both aPDI and aPDI employ a nontoxic dye termed a photosensitizer (PS) and harmless low-intensity visible light in a broad wavelength spectrum to match multi-absorption peaks of the PS. These individually harmless elements can interact in the presence of molecular oxygen, via triplet energy transfer, to produce reactive oxygen species (ROS), such as singlet oxygen ($^1O_2$, via Type-II photomechanism) and hydroxyl radical (HO·, via Type-I photomechanism). It is well accepted that aPDT can inactivate all known classes of microorganism, including Gram-positive, Gram-negative bacteria, fungi, and protozoa etc. regardless of the status of multidrug- or pandrug-resistancy. Without being held to theory, it is believed that the treatment method of aPDI and aPDT itself is unlikely to induce resistance, as damages made by ROS on DNA and the cell is caused by a non-specific killing mechanism as compared with that of antibiotics generally initiated by a specific enzyme inhibition. The speed of action is rapid for aPDI (many logs killed over minutes) as compared with antibiotics that typically require many days or weeks to be effective. The latter makes it easier to induce drug-resistance mutations. Thus, aPDI serves as a promising approach to combat multidrug-resistant strain microbe species.

The aPDI approach disclosed herein utilizes relatively nontoxic functionalized nanocarbons ($C_{60}$ or $C_{70}$)-chromophore antenna conjugates as nano-photosensitizers (nano-$C_{60/70}$PSs) coupled with an unhazardous visible light for photoexcitation of both $C_{60}$ or $C_{70}$ and chromophore antenna moieties to produce microbe-killing ROS.

Nanocarbon cages ($C_{60}$, $C_{70}$, $C_{84}$, etc.) in a typical example of derivatized $C_{60}$> are highly photostable and suitable for multiple PDT treatment applications just by a single dose. The high number of reactive fullerenyl olefins can also facilitate multiple attachments of various substrates to accommodate the need of drug delivery and targeting.

Examples of nano-fullerenyl photosensitizers (nano-$C_{60/70}$PS) were reported to include decacationic malonato[60] fullerene derivative with their ability to mediate aPDI using pathogenic microbial cells, including Gram-positive methicillin-resistant *Staphylococcus aureus* (MRSA) bacterium, Gram-negative *Escherichia coli* bacterium, and fungal yeast *Candida albicans*, under irradiation of UVA or white light. In these particular chemical structures, two pentacationic arm moieties were applied to increase the selective targeting ability of nano-$C_{60}$PS toward microbial cells over mammalian cells, while the nanocarbon cage core moiety works as an active photosensitizer. Nano-$C_{60/70}$PSs with ten iodide anions per molecule was found to be capable of co-producing singlet oxygen (Type-II) and highly reactive hydroxyl radicals (Type-I, derived from superoxide radicals) in its photosensitizing reactions upon illumination at either UVA or white light wavelengths. The latter was reasoned to occur by the ability of iodide anions to act as electron donors to perform photoinduced electron-transfer to the strongly electronegative $C_{60}$ cage in the same molecular environment. A high number of t per nano-$C_{60/70}$PS molecule is certainly beneficial and favorable to the generation of Type-I radicals over the competitive Type-II $^1O_2$. As it is generally recognized that HO· can produce more effective killing of pathogens than $^1O_2$, the compounds described herein were designed to largely increase the photoinduced radical production and decrease the Type-II photochemistry under confined photoenergy applied.

By the covalent-bond (CB) attachment of an antibiotic molecule (Abx) to a nano-$C_{60/70}$PS, it forms the corresponding conjugate of $C_{60/70}$PS-CB-Abx to enhance the antimicrobial aPDT effect. Accordingly, it becomes plausible to practice the combinatorial antimicrobial therapy using novel water-soluble cyclopropyl-functionalized spherical carbon-cage ($C_{60}$, $C_{70}$, or $C_{84}$, etc.) in $C_{60/70}$-derivated fullerenyl photosensitizers (nano-$C_{60/70}$PSs as nanodrugs) mediated aPDT with clinically used antibiotics for the treatment of localized bacterial infections. Combination therapies that allow synergistic interactions between different antimicrobials are also arguably the most effective approach to combat antibiotic resistance. In contrast to traditional combination therapies by simply applying the physical mixtures of different antimicrobial agents, the compositions disclosed in this invention are covalently conjugated antibiotics with nano-$C_{60/70}$PSs into one nanostructure. This nanoconjugated structure leads to controlled co-targeted delivery of nano-$C_{60/70}$PS and the covalently-bonded antibiotics (CB-Abx, one or two agents) to the infection sites for enhanced antimicrobial effect. Another advantage of the combinatorial therapy of aPDT and antibiotics over aPDT alone is that antibacterial effective remains active after light irradiation, due to the presence of antibiotics on the infection sites, which can prevent the reoccurrence of infections. It is worthwhile to note that repeated oral administration of $C_{60}$ in olive oil to rats was found to entail no chronic toxicity.

Accordingly, described herein is a $C_{60/70}$PS-CB-Abx fullerenyl mesochlorin photosensitizer with covalently bounded antibiotics. The compounds exhibit combined therapeutic effects of photodynamic and antibiotic cytotoxicities. Also described is the nano-$C_{60/70}$PS fullerenyl chlorin photosensitizer without covalently bonded antibiotic molecules. Also disclosed are methods for preparing these nano-$C_{60/70}$PS compounds and $C_{60/70/}$PS-CB-Abx conjugates.

In an aspect, a $C_{60/70}$PS-CB-Abx compound has the following formula (I):

(I)

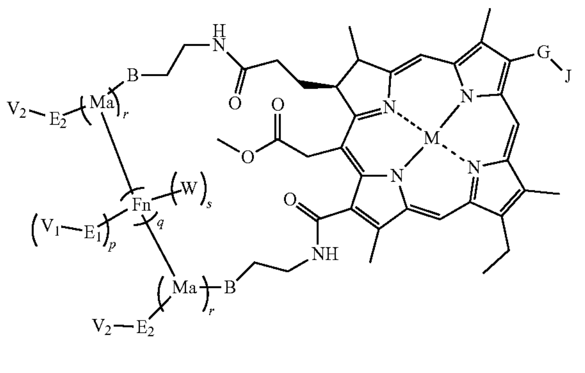

wherein

Fn is a fullerene core;

M is a metal ion;

B is amino-$C_{2\text{-}200}$ alkyl ether, amino-$C_{2\text{-}200}$ alkyl, hydroxy-$C_{2\text{-}200}$ alkyl ether, or hydroxy-$C_{2\text{-}200}$ alkyl;

Ma is —NH—CO-cyclopropanyl-CO— or —O—CO-cyclopropanyl-CO—;

G is —CH(O—$V_2$)—$CH_2$— or —CH(O—CO—Z—$V_2$)—$CH_2$;

J is -$E_3$-Abx; wherein Abx is an amino or amide group-containing antibiotic molecule;

$E_1$, $E_2$, and $E_3$ are each independently $Y_1$,$Y_2$-amino, ($Y_1$,$Y_2$-alkyl)-amino, $Y_1$,$Y_2$-ethylenediamino, (dihydroxymethyl)alkylamino, ($X_1$,$X_3$-aryl)amino, $X_1$,$X_3$-aryloxy, $Y_2$-alkoxy, $Y_1$,$Y_2$-alkoxy, ($Y_1$,$Y_2$-amino) alkoxy, ($Y_1$,$Y_2$,$Y_3$-aryl)oxy, (dihydroxyalkyl)-aryloxy, ($Y_1$,$Y_2$,$Y_3$-alkyl)amino, ($Y_1$,$Y_2$,$Y_3$-aryl)amino, dihydroxyalkylamino, $Y_1$,$Y_2$,$Y_3$-alkoxy, (trihydroxyalkyl) alkoxy, (trihydroxyalkyl)alkylamino, (dicarboxyalkyl) amino, $Y_2$-thio, ($Y_1$,$Y_2$,$Y_3$-alkyl)thio, ($X_1$,$X_3$-aryl) thio, ($Y_1$,$Y_2$-alkyl)thio, (dihydroxyalkyl)thio, $Y_1$,$Y_2$-dioxoalkyl, tri-($Y_1$,$Y_2$,$Y_3$-methylaminocarboxyethyl) methylamino, ((glycosidyl)oxoheteroaryl)amino, ((glycosidyl)oxoaryl)amino, ($X_1$,$X_2$,$X_3$-heteroaryl) amino, ($X_1$-diarylketone)amino, (T,$X_1$-oxoaryl)amino, (T,$X_1$-dioxoaryl)amino, ($Y_1$-alkyl,$Y_2$-alkyldioxoheteroaryl)amino, ($Y_1$-alkyl,$Y_2$-alkyldioxoaryl)amino, (di ($Y_1$,$Y_2$-methyl)dioxoheteroaryl)amino, (di($Y_1$,$Y_2$-methyl)dioxoaryl)amino, ((glycosidyl)heteroaryl) amino, ((glycosidyl)aryl)amino, ((carboxylacetylalkyl) oxo-heteroaryl)amino, ((carboxylacetylalkyl)oxoaryl) amino, ((isopropylaminohydroxy-alkoxy)aryl)amino, ($X_1$,$X_2$,$X_3$-alkylaryl)amino, ($X_1$,$X_2$,$X_3$-heteroaryl)oxy, (isopropylaminohydroxyalkyl)aryloxy, ($X_1$,$X_2$,$X_3$-oxoheteroaryl)oxy, ($X_1$,$X_2$,$X_3$-oxoaryl)oxy, ($X_1$,$Y_1$-oxoheteroaryl)oxy, ($X_1$-diarylketone)oxy, (T,$X_1$-oxoaryl)oxy, ($X_1$,$X_2$-dioxoaryl)oxy, ($Y_1$,$Y_2$,di-aminodihydroxy)alkyl, ($X_1$,$X_2$-heteroaryl)thio, ((tricarboxylalkyl)ethylene-diamino)alkoxy, ($X_1$,$X_2$-oxoaryl)thio, ($X_1$,$X_2$-dioxoaryl)thio, (glycosidylheteroaryl)thio, (glycosidylaryl)thio, $Y_1$-alkyl(thiocarbonyl)thio, $Y_1$,$Y_2$,-alkyl(thiocarbonyl)thio, $Y_1$,$Y_2$,$Y_3$-alkyl(thiocarbonyl)thio, ($Y_1$,$Y_2$-aminothiocarbonyl) thio, (pyranosyl)thio, cysteinyl, tyrosinyl, (phenylalaninyl)amino, (dicarboxyalkyl)thio, (aminoaryl)$_{1\text{-}100}$amino, (pyranosyl)$_{1\text{-}100}$amino, ($Y_1$-aminoaryl)$_{1\text{-}100}$amino, (amino(sulfoaryl))$_{1\text{-}100}$amino, peptidyl, thymidinyl, uridinyl, guanosinyl, adenosinyl, cholesteryl, or biotinylalkoxy; wherein T is halo;

each of $X_1$, $X_2$, and $X_3$ is each independently —$Y_2$, —O—$Y_2$, —S—$Y_2$, —NH—$Y_2$, —CO—O—$Y_2$, —O—CO—$Y_2$, —CO—NH—$Y_2$, —CO—$NY_1Y_2$, —NH—CO—$Y_2$, —$SO_2$—$Y_2$, —$SO_2$—O—$Y_2$, —$CHY_1Y_2$, or —$NY_1Y_2$;

each of $Y_1$, $Y_2$, and $Y_3$ is each independently —H, -Q-Z—H or —Z—H; in which each Q, independently, is —$R^a$—O—$[Si(CH_3)_2$—O—$]_{1-100}$-, —$C_{1-2000}$ alkyl-, —$C_{6-40}$ aryl-, —$C_{7-2000}$ alkylaryl-, —$C_{7-2000}$ arylalkyl-, —($C_{1-30}$ alkyl ether)$_{1-100}$-, —($C_{6-40}$ aryl ether)$_{1-100}$-, —($C_{7-2000}$ alkylaryl ether)$_{1-100}$-, —($C_{7-2000}$ arylalkyl ether)$_{1-100}$-, —($C_{1-30}$ alkyl thioether)$_{1-100}$-, —($C_{6-40}$ aryl thioether)$_{1-100}$-, —($C_{7-2000}$ alkylaryl thioether)$_{1-100}$-, —($C_{7-2000}$ arylalkyl thioether)$_{1-100}$-, —($C_{2-50}$ alkyl ester)$_{1-100}$-, —($C_{7-2000}$ aryl ester)$_{1-100}$-, —($C_{8-2000}$ alkylaryl ester)$_{1-100}$-, —($C_{8-2000}$ arylalkyl ester)$_{1-100}$-, —$R^a$—CO—O—($C_{1-30}$ alkyl ether)$_{1-100}$-, —$R^a$—CO—O—($C_{6-40}$ aryl ether)$_{1-100}$-, —$R^a$—CO—O—($C_{7-2000}$ alkylaryl ether)$_{1-100}$-, —$R^a$—CO—O—($C_{7-2000}$ arylalkyl ether)$_{1-100}$-, —($C_{4-50}$ alkyl urethane)$_{1-100}$-, —($C_{14-60}$ aryl urethane)$_{1-100}$-, —($C_{10-2000}$ alkylaryl urethane)$_{1-100}$-, —($C_{10-2000}$ arylalkyl urethane)$_{1-100}$-, —($C_{5-50}$ alkyl urea)$_{1-100}$-, —($C_{14-60}$ aryl urea)$_{1-100}$-, —($C_{10-2000}$ alkylaryl urea)$_{1-100}$-, —($C_{10-2000}$ arylalkyl urea)$_{1-100}$-, —($C_{2-50}$ alkyl amide)$_{1-100}$-, —($C_{7-60}$ aryl amide)$_{1-100}$-, —($C_{8-2000}$ alkylaryl amide)$_{1-100}$-, —($C_{8-2000}$ arylalkyl amide)$_{1-100}$-, —($C_{3-30}$ alkyl anhydride)$_{1-100}$-, —($C_{8-50}$ aryl anhydride)$_{1-100}$-, —($C_{9-2000}$ alkylaryl anhydride)$_{1-100}$-, —($C_{9-2000}$ arylalkyl anhydride)$_{1-100}$-, —($C_{2-30}$ alkylcarbonate)$_{1-100}$-, —($C_{7-50}$ aryl carbonate)$_{1-100}$-, —($C_{8-2000}$ alkylaryl carbonate)$_{1-100}$-, —($C_{8-2000}$ arylalkyl carbonate)$_{1-100}$-, —$R^a$—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$-, —$R^a$—O—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$-, —$R^a$—O—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$-CO—NH—($R^b$ or Ar—$R^b$—Ar)—NH—CO—O—, —$R^a$—O—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$-$R^c$—O—CO—NH—($R^b$ or Ar—$R^b$—Ar)—NH—CO—O—, —$R^a$—NH—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$-, —$R^a$—NH—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$-, —$R^a$—NH—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$-CO—NH—($R^b$ or Ar—$R^b$—Ar)—NH—CO—O—, —$R^a$—NH—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$-, —$R^c$—O—CO—NH—($R^b$ or Ar—$R^b$—Ar)—NH—CO—O—, —$R^a$—O—CO—NH—($R^b$ or Ar—$R^b$—Ar)—NH—CO—NH—($C_{2-50}$ alkyl amide, $C_{7-60}$ aryl amide, $C_{8-2000}$ alkylaryl amide, or $C_{8-2000}$ arylalkyl amide)$_{1-100}$-, —$R^a$—NH—CO—NH—($R^b$ or Ar—$R^b$—Ar)—NH—CO—NH—($C_{2-50}$ alkyl amide, $C_{7-60}$ aryl amide, $C_{8-2000}$ alkylaryl amide, or $C_{8-2000}$ arylalkyl amide)$_{1-100}$-, —$CH_2$—CH(OH)—$CH_2$—$(OCH_2CH_2)_{1-100}$—$OCH_2CH(OH)$—$CH_2$, —$CH_2$—CH(OH)—$CH_2$—$N^+HR^a$—$(CH_2CH_2N^+R^aR^b)_{1-100}$—$CH_2CH_2N^+HR^a$—$CH_2CH(OH)CH_2$—, or —$CH_2CH_2$—$N^+R^aR^b$—$(CH_2CH_2N^+R^aR^b)_{1-100}$—$R^c$—; and each Z, independently, is —$R^a$—, —$R^a$—Ar—, —Ar—$R^a$—, or —Ar—; and $V_1$ and $V_2$ independently are —OH, —SH, —$NH_2$, —NHOH, —$SO_3H$, —$OSO_3H$, —$CO_2H$, —$CONH_2$, —$CONHNH_2$, —$CH(NH_2)$—$CO_2H$, —NH—$CH_2$—$CO_2H$, —$P(OH)_3$, —$PO(OH)_2$, —O—$PO(OH)_2$, —O—PO(OH)—O—$PO(OH)_2$, —O—$PO(O^-)$—O—$CH_2CH_2NH_3^+$, —O—$PO(O^-)$—O—$CH_2CH_2$—$N^+(CH_3)_3$, -glycoside, -oligosaccharide, —CO-glycoside, —CO-oligosaccharide, —$OCH_3$, —$OCH_2(CHOH)_4$—$CH_2OH$, —$OCH_2(CHOH)_2$—$CH_2OH$, —CO—$OCH_2(CHOH)_4$—$CH_2OH$, —$C_6H_3(OH)_2$, —$N(CH_2CO_2H)_2$, —CO—$N(CH_2CO_2H)_2$, —CO—NH—$C(CH_2CH_2CO_2H)_3$, —CO—NH—$C(CH_2CH_2OH)_3$, —$[CH_2$—$CH(CO_2R^a)]_{1-100}$—H, —O—$(CH_2CH_2O)_{1-100}$—H, —$NH_3^+$, —$N^+H_2R^a$, —$N^+HR^aR^b$, or —$N^+R^aR^bR^c$;

wherein each of $R^a$, $R^b$, and $R^c$ are each independently $C_{1-20}$ linear or branched alkyl;

Ar is aryl;

W is hydroxyl or amino;

p and s each independently is 0-20; and r and q each independently is 0 or 1.

A nano-$C_{60/70}$PS compound has the following formula (II):

(II)

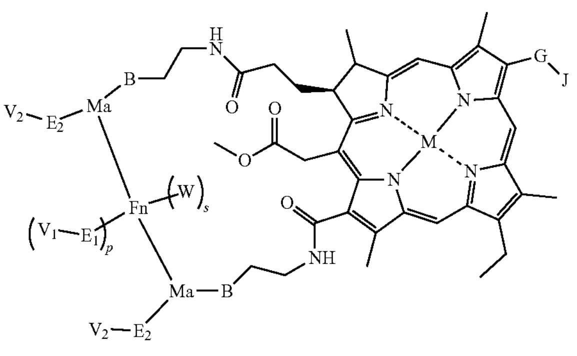

wherein

Fn is a fullerene core;

M is a metal ion;

B is amino-$C_{2-200}$ alkyl ether, amino-$C_{2-200}$ alkyl, hydroxy-$C_{2-200}$ alkyl ether, or hydroxy-$C_{2-200}$ alkyl;

Ma is —NH—CO-cyclopropanyl-CO— or —O—CO-cyclopropanyl-CO—;

K is —CH=CH—, —CH(O—$V_2$)—$CH_2$— or —CH(O—CO—Z—$V_2$)—$CH_2$—;

L is —H or -$E_3$-$V_2$;

$E_1$, $E_2$, and $E_3$ are each independently $Y_1$,$Y_2$-amino, ($Y_1$,$Y_2$-alkyl)-amino, $Y_1$,$Y_2$-ethylenediamino, (dihydroxymethyl)alkylamino, ($X_1$,$X_3$-aryl)amino, $X_1$,$X_3$-aryloxy, $Y_2$-alkoxy, $Y_1$,$Y_2$-alkoxy, ($Y_1$,$Y_2$-amino)alkoxy, ($Y_1$,$Y_2$,$Y_3$-aryl)oxy, (dihydroxyalkyl)-aryloxy, ($Y_1$,$Y_2$,$Y_3$-alkyl)amino, $Y_1$,$Y_2$,$Y_3$-aryl)amino, dihydroxyalkylamino, $Y_1$,$Y_2$,$Y_3$-alkoxy, (trihydroxyalkyl)alkoxy, (trihydroxyalkyl)alkylamino, (dicarboxyalkyl)amino, $Y_2$-thio, ($Y_1$,$Y_2$,$Y_3$-alkyl)thio, ($X_1$,$X_3$-aryl)thio, ($Y_1$,$Y_2$-alkyl)thio, (dihydroxyalkyl)thio, $Y_1$,$Y_2$- dioxoalkyl, tri-($Y_1$,$Y_2$,$Y_3$-methylaminocarboxyethyl)methylamino, ((glycosidyl)oxoheteroaryl)amino, ((glycosidyl)oxoaryl)amino, ($X_1$,$X_2$,$X_3$-heteroaryl)amino, ($X_1$-diarylketone)amino, (T,$X_1$-oxoaryl)amino, (T,$X_1$-dioxoaryl)amino, ($Y_1$-alkyl,$Y_2$-alkyldioxoheteroaryl)amino, ($Y_1$-alkyl,$Y_2$-alkyldioxoaryl)amino, (di($Y_1$,$Y_2$-methyl)dioxoheteroaryl)amino, (di($Y_1$,$Y_2$-methyl)dioxoaryl)amino, ((glycosidyl)heteroaryl)amino, ((glycosidyl)aryl)amino, ((carboxylacetylalkyl)oxo-heteroaryl)amino, ((carboxylacetylalkyl)oxoaryl)amino, ((isopropylaminohydroxy-alkoxy)aryl)amino, ($X_1$,$X_2$,$X_3$-alkylaryl)amino, ($X_1$,$X_2$,$X_3$-heteroaryl)oxy, (isopropylaminohydroxyalkyl)aryloxy, ($X_1$,$X_2$,$X_3$-oxoheteroaryl)oxy, ($X_1$,$X_2$,$X_3$-oxoaryl)oxy, ($X_1$,$Y_1$-oxoheteroaryl)oxy, ($X_1$-diarylketone)oxy, (T,$X_1$-oxoaryl)oxy, ($X_1$,$X_2$-dioxoaryl)oxy, ($Y_1$,$Y_2$,di-aminodihydroxy)alkyl, ($X_1$,$X_2$-heteroaryl)thio, ((tricarboxylalkyl)ethylene-diamino)alkoxy, ($X_1$,$X_2$-oxoaryl)thio, ($X_1$,$X_2$-dioxoaryl)thio, (glycosidylheteroaryl)thio, (glycosidylaryl)thio, $Y_1$-alkyl(thiocarbonyl)thio, $Y_1$,$Y_2$,-alkyl(thiocarbonyl)thio, $Y_1$,$Y_2$,$Y_3$-alkyl(thiocarbonyl)thio, ($Y_1$,$Y_2$-aminothiocarbonyl)thio, (pyranosyl)thio, cysteinyl, tyrosinyl, (phenylalaninyl)amino, (dicarboxyalkyl)thio, (aminoaryl)$_{1-100}$amino, (pyranosyl)$_{1-100}$amino, ($Y_1$-aminoaryl)$_{1-100}$amino, (amino(sulfoaryl))$_{1-100}$amino, peptidyl, thymidinyl, uridinyl, guanosinyl, adenosinyl, cholesteryl, or biotinylalkoxy; wherein T is halo;

each of $X_1$, $X_2$, and $X_3$ is each independently —$Y_2$, —O—$Y_2$, —S—$Y_2$, —NH—$Y_2$, —CO—O—$Y_2$, —O—CO—$Y_2$, —CO—NH—$Y_2$, —CO—$NY_1Y_2$, —NH—CO—$Y_2$, —$SO_2$—$Y_2$, —$SO_2$—O—$Y_2$, —$CHY_1Y_2$, or —$NY_1Y_2$;

each of $Y_1$, $Y_2$, and $Y_3$ is each independently —H, -Q-Z—H or —Z—H; in which each Q, independently, is —$R^a$—O—[Si($CH_3$)$_2$—O—]$_{1-100}$-, —$C_{1-2000}$ alkyl-, —$C_{6-40}$ aryl-, —$C_{7-2000}$ alkylaryl-, —$C_{7-2000}$ arylalkyl-, —($C_{1-30}$ alkyl ether)$_{1-100}$-, —($C_{6-40}$ aryl ether)$_{1-100}$-, —($C_{7-2000}$ alkylaryl ether)$_{1-100}$-, —($C_{7-2000}$ arylalkyl ether)$_{1-100}$-, —($C_{1-30}$ alkyl thioether)$_{1-100}$-, —($C_{6-40}$ aryl thioether)$_{1-100}$-, —($C_{7-2000}$ alkylaryl thioether)$_{1-100}$-, —($C_{7-2000}$ arylalkyl thioether)$_{1-100}$-, —($C_{2-50}$ alkyl ester)$_{1-100}$-, —($C_{7-2000}$ aryl ester)$_{1-100}$-, —($C_{8-2000}$ alkylaryl ester)$_{1-100}$-, —($C_{8-2000}$ arylalkyl ester)$_{1-100}$-, —$R^a$—CO—O—($C_{1-30}$ alkyl ether)$_{1-100}$-, —$R^a$—CO—O—($C_{6-40}$ aryl ether)$_{1-100}$-, —$R^a$—CO—O—($C_{7-2000}$ alkylaryl ether)$_{1-100}$-, —$R^a$—CO—O—($C_{7-2000}$ arylalkyl ether)$_{1-100}$-, —($C_{4-50}$ alkyl urethane)$_{1-100}$-, —($C_{14-60}$ aryl urethane)$_{1-100}$-, —($C_{10-2000}$ alkylaryl urethane)$_{1-100}$-, —($C_{10-2000}$ arylalkyl urethane)$_{1-100}$-, —($C_{5-50}$ alkyl urea)$_{1-100}$-, —($C_{14-60}$ aryl urea)$_{1-100}$-, —($C_{10-2000}$ alkylaryl urea)$_{1-100}$-, —($C_{10-2000}$ arylalkyl urea)$_{1-100}$-, —($C_{2-50}$ alkyl amide)$_{1-100}$-, —($C_{7-60}$ aryl amide)$_{1-100}$-, —($C_{8-2000}$ alkylaryl amide)$_{1-100}$-, —($C_{8-2000}$ arylalkyl amide)$_{1-100}$-, —($C_{3-30}$ alkyl anhydride)$_{1-100}$-, —($C_{8-50}$ aryl anhydride)$_{1-100}$-, —($C_{9-2000}$ alkylaryl anhydride)$_{1-100}$-, —($C_{9-2000}$ arylalkyl anhydride)$_{1-100}$-, —($C_{2-30}$ alkylcarbonate)$_{1-100}$-, —($C_{7-50}$ aryl carbonate)$_{1-100}$-, —($C_{8-2000}$ alkylaryl carbonate)$_{1-100}$-, —($C_{8-2000}$ arylalkyl carbonate)$_{1-100}$-, —$R^a$—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$-, —$R^a$—O—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$-, —$R^a$—O—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$-CO—NH—($R^b$ or Ar—$R^b$—Ar)—NH—CO—O—, —$R^a$—O—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$-$R^c$—O—CO—NH—($R^b$ or Ar—$R^b$—Ar)—NH—CO—O—, —$R^a$—NH—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$-, —$R^a$—NH—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$-, —$R^a$—NH—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$-CO—NH—($R^b$ or Ar—$R^b$—Ar)—NH—CO—O—, —$R^a$—NH—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$-, —$R^c$—O—CO—NH—($R^b$ or Ar—$R^b$—Ar)—NH—CO—O—, —$R^a$—O—CO—NH—($R^b$ or Ar—$R^b$—Ar)—NH—CO—NH—($C_{2-50}$ alkyl amide, $C_{7-60}$ aryl amide, $C_{8-2000}$ alkylaryl amide, or $C_{8-2000}$ arylalkyl amide)$_{1-100}$-, —$R^a$—NH—CO—NH—($R^b$ or Ar—$R^b$—Ar)—NH—CO—NH—($C_{2-50}$ alkyl amide, $C_{7-60}$ aryl amide, $C_{8-2000}$ alkylaryl amide, or $C_{8-2000}$ arylalkyl amide)$_{1-100}$-, —$CH_2$—CH(OH)—$CH_2$—($OCH_2CH_2$)$_{1-100}$—$OCH_2CH(OH)$—$CH_2$, —$CH_2$—CH(OH)—$CH_2$—$N^+HR^a$—($CH_2CH_2N^+R^aR^b$)$_{1-100}$—$CH_2CH_2N^+HR^a$—$CH_2CH(OH)CH_2$—, or —$CH_2CH_2$—$N^+R^aR^b$—($CH_2CH_2N^+R^aR^b$)$_{1-100}$—$R^c$—; and each Z, independently, is —$R^a$—, —$R^a$—Ar—, —Ar—$R^a$—, or —Ar—; and $V_1$ and $V_2$ independently are —OH, —SH, —$NH_2$, —NHOH, —$SO_3H$, —$OSO_3H$, —$CO_2H$, —$CONH_2$, —$CONHNH_2$, —CH($NH_2$)—$CO_2H$, —NH—$CH_2$—$CO_2H$, —$P(OH)_3$, —$PO(OH)_2$, —O—$PO(OH)_2$, —O—PO(OH)—O—$PO(OH)_2$, —O—$PO(O^-)$—O—$CH_2CH_2NH_3^+$, —O—$PO(O^-)$—O—$CH_2CH_2$—$N^+(CH_3)_3$, -glycoside, -oligosaccharide, —CO-glycoside, —CO-oligosaccharide, —$OCH_3$, —$OCH_2(CHOH)_4$—$CH_2OH$, —$OCH_2(CHOH)_2$—$CH_2OH$, —CO—$OCH_2(CHOH)_4$—$CH_2OH$, —$C_6H_3(OH)_2$, —$N(CH_2CO_2H)_2$, —CO—$N(CH_2CO_2H)_2$, —CO—NH—$C(CH_2CH_2CO_2H)_3$, —CO—NH—$C(CH_2CH_2OH)_3$, —[$CH_2$—CH($CO_2R^a$)]$_{1-100}$—H, —O—($CH_2CH_2O$)$_{1-100}$—H, —$NH_3^+$, —$N^+H_2R^a$, —$N^+HR^aR^b$, or —$N^+R^aR^bR^c$;

wherein each of $R^a$, $R^b$, and $R^c$ are each independently $C_{1-20}$ linear or branched alkyl;

Ar is aryl;

W is hydroxyl or amino;

p and s each independently is 0-20; and

In formulas I and II, B is amino-$C_{2-200}$ alkyl ether, amino-$C_{2-200}$ alkyl, hydroxy-$C_{2-200}$ alkyl ether, or hydroxy-$C_{2-200}$ alkyl wherein the amino group or the hydroxyl group is linked to a Ma carbonyl group as an amide or ester. Ma, between $E_2$ and B, is —NH—CO-cyclopropanyl-CO— or —O—CO-cyclopropanyl-CO— wherein the cyclopropanyl group is formed by an α-alkyl carbon of Ma bonded to two Fn (fullerenyl) carbons.

In formulas I and II, in certain aspects, Fn is $C_{60}$, $C_{70}$, $C_{76}$, $C_{78}$, $C_{82}$, $C_{84}$, $C_{92}$, (methano)$_n C_{60}$, (methano)$_n C_{70}$, (pyrrolidino)$_n C_{60}$, (pyrrolidino)$_n C_{70}$, La@$C_y$, Ho@$C_y$, Gd@$C_y$, Er@$C_y$, (methano)$_n$La@$C_y$, (methano)$_n$Ho@$C_y$, (methano)$_n$Gd@C$_y$, (methano)$_n$Er@C$_y$, (pyrrolidino)$_n$La@C$_y$, (pyrrolidino)$_n$Ho@C$_y$, (pyrrolidino)$_n$Gd@C$_y$, or (pyrrolidino)$_n$Er@C$_y$, wherein n is 1-10, and y is 60, 74, or 82. In specific aspects, Fn is $C_{60}$, $C_{70}$, or $C_{84}$.

In formulas I and II, in certain aspects, M is a Cu, Mn, Fe, Co, Ni, Ru, Rh, Zn, Pd, Pt, Ti, Si, or Zr ion. In specific aspects, M is a Mn, Ru, Rh, Zn, Pd, Pt, or Si ion.

In formulas I and II, in certain aspects, Abx is vancomycin, imipenem, gentamicin, tetracycline, tigecycline, minocycline, meropenem, ceftazidime, ciprofloxacin, norfloxacin, moxifloxacin, amikacin, kanamycin, aminopenicillin, tobramycin, doripenem, amoxicillin, or ampicillin. In specific aspects, In formulas I and II, in certain aspects, $E_1$, $E_2$, $E_3$ are each independently $Y_1$,$Y_2$-amino, $Y_2$-amino, ($Y_1$,$Y_2$-alkyl)-amino, $Y_1$,$Y_2$-ethylenediamino, (dihydroxymethyl)alkylamino, ($X_1$,$X_3$-aryl)amino, ($Y_1$,$Y_2$,$Y_3$-alkyl)amino, ($Y_1$,$Y_2$,$Y_3$-aryl)amino, dihydroxyalkylamino, (trihydroxyalkyl) alkylamino, or (dicarboxyalkyl)amino; and p is 1-4.

In formulas I and II, in certain aspects, each of $X_1$, $X_2$, and $X_3$ is hydrogen.

In formulas I and II, in certain aspects, $V_1$ and $V_2$ are each independently hydrogen, $C_{1-2000}$ alkyl, $C_{6-40}$ aryl, or $C_{7-2000}$ arylalkyl, optionally substituted with —OH, —SH, —$NH_2$, —NHOH, —$SO_3$H, —$OSO_3$H, —$CO_2$H, —$CONH_2$, —$CONHNH_2$, —CH($NH_2$)—$CO_2$H, —NH—$CH_2$—$CO_2$H, —O—($CH_2CH_2O$)$_{1-100}$—H, —$NH_3^+$, —$N^+H_2R^a$, —$N^+HR^aR^b$, —$N^+R^aR^bR^c$, or —NH—($CH_2CH_2N^+R^aR^b$)$_{1-100}$—$R^c$.

In formulas I and II, in certain aspects, $V_1$ and $V_2$ are each independently —$NH_3^+$, —$N^+H_2R^a$, —$N^+HR^aR^b$, —$N^+R^aR^bR^c$, or —NH—($CH_2CH_2N^+R^aR^b$)$_{1-100}$—$R^c$; the counter anion is chloride, bromide, iodide, triiodide, sulfate, pyrosulfate, bisulfate, sulfite, bisulfite, thiosulfate, nitrate, nitrite, phosphate, azide, thiocyanate, selenocyanate, or acetate.

In formulas I and II, in certain aspects, $E_1$-$V_1$ is hydroxy or amino; and p is 0-20.

In another aspect, also included is a nano-$C_{60/70}$PS compound of the following formula (III):

$R^{cf}$, or —O—$C_{2-50}$ alkyl-$N^+R^{ad}R^{be}$—($CH_2CH_2N^+R^{ad}R^{be}$)$_{1-100}$—$R^{ef}$; wherein each of $R^{ad}$, $R^{be}$, and $R^{cf}$ are each independently —H or —$C_{1-20}$ linear or branched alkyl;

$E_1$, is $Y_1$,$Y_2$-amino, ($Y_1$,$Y_2$-alkyl)-amino, $Y_1$,$Y_2$-ethylenediamino, (dihydroxymethyl)alkylamino, ($X_1$,$X_3$-aryl)amino, $X_1$,$X_3$-aryloxy, $Y_2$-alkoxy, $Y_1$,$Y_2$-alkoxy, ($Y_1$,$Y_2$-amino)alkoxy, ($Y_1$,$Y_2$,$Y_3$-aryl)oxy, (dihydroxyalkyl)-aryloxy, ($Y_1$,$Y_2$,$Y_3$-alkyl)amino, ($Y_1$,$Y_2$,$Y_3$-aryl)amino, dihydroxyalkylamino, $Y_1$,$Y_2$,$Y_3$-alkoxy, (trihydroxyalkyl)alkoxy, (trihydroxyalkyl) alkylamino, (dicarboxyalkyl)amino, $Y_2$-thio, ($Y_1$,$Y_2$,$Y_3$-alkyl)thio, ($X_1$,$X_3$-aryl)thio, ($Y_1$,$Y_2$-alkyl)thio, (dihydroxyalkyl)thio, $Y_1$,$Y_2$-dioxoalkyl, tri-($Y_1$,$Y_2$,$Y_3$-methylaminocarboxyethyl)methylamino, ((glycosidyl) oxoheteroaryl)amino, ((glycosidyl)oxoaryl)amino, ($X_1$,$X_2$,$X_3$-heteroaryl)amino, ($X_1$-diarylketone)amino, (T,$X_1$-oxoaryl)amino, (T,$X_1$-dioxoaryl)amino, ($Y_1$-alkyl,$Y_2$-alkyldioxoheteroaryl)amino, ($Y_1$-alkyl, $Y_2$-alkyldioxoaryl)amino, (di($Y_1$,$Y_2$-methyl)dioxoheteroaryl)amino, (di($Y_1$,$Y_2$-methyl)dioxoaryl)amino, ((glycosidyl)heteroaryl)amino, ((glycosidyl)aryl) amino, ((carboxylacetylalkyl)oxo-heteroaryl)amino, ((carboxylacetylalkyl)oxoaryl)amino, ((isopropylaminohydroxy-alkoxy)aryl)amino, ($X_1$,$X_2$,$X_3$-alkylaryl) amino, ($X_1$,$X_2$,$X_3$-heteroaryl)oxy, (isopropylaminohydroxyalkyl)aryloxy, ($X_1$,$X_2$,$X_3$-oxoheteroaryl)oxy, ($X_1$,$X_2$,$X_3$-oxoaryl)oxy, ($X_1$,$Y_1$-oxoheteroaryl)oxy, ($X_1$-diarylketone)oxy, (T,$X_1$-oxoaryl)oxy, ($X_1$,$X_2$-dioxoaryl)oxy, ($Y_1$,$Y_2$,di-aminodihydroxy)alkyl, ($X_1$,$X_2$-heteroaryl)thio, ((tricarboxylalkyl)ethylene-diamino) alkoxy, ($X_1$,$X_2$-oxoaryl)thio, ($X_1$,$X_2$-dioxoaryl)thio, (glycosidylheteroaryl)thio, (glycosidylaryl)thio, $Y_1$-alkyl(thiocarbonyl)thio, $Y_1$,$Y_2$,-alkyl(thiocarbonyl)thio, $Y_1$,$Y_2$,$Y_3$-alkyl(thiocarbonyl)thio, ($Y_1$,$Y_2$-aminothiocarbonyl)thio, (pyranosyl)thio, cysteinyl, tyrosinyl, (phenylalaninyl)amino, (dicarboxyalkyl)thio, (aminoaryl)$_{1-100}$amino, (pyranosyl)$_{1-100}$amino, ($Y_1$-aminoaryl)$_{1-100}$amino, (amino(sulfoaryl))$_{1-100}$amino, peptidyl, thymidinyl, uridinyl, guanosinyl, adenosinyl, cholesteryl, or biotinylalkoxy; wherein T is halo;

(III)

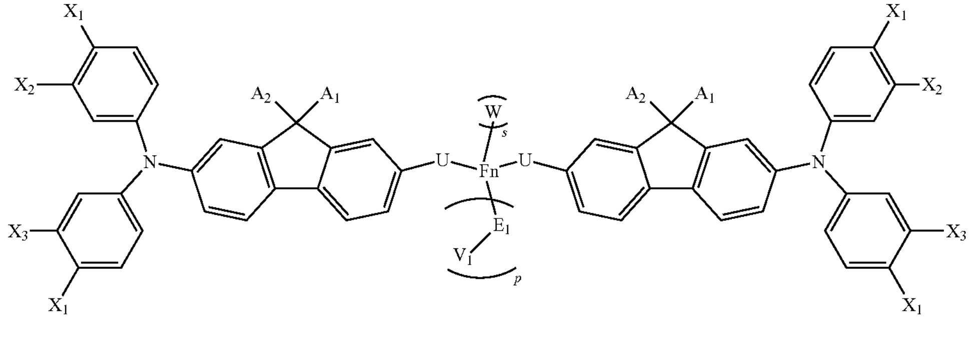

wherein

Fn is a fullerene core;

U is —CO— or [C═C(CN)$_2$]—;

$A_1$ and $A_2$ are each independently —$P_1$—$P_2$;

$P_1$ is —$C_{2-200}$ alkyl-(CO)—, —$C_{2-200}$ alkyl ether-(CO)—, —$C_{2-200}$ alkylaryl-(CO)—, or —$C_{2-200}$ alkylaryl ether-(CO)—; and $P_2$ is —NH—$C_{2-50}$ alkyl-($OCH_2CH_2$)$_{1-100}$—$R^{cf}$, —O—$C_{2-50}$ alkyl-($OCH_2CH_2$)$_{1-100}$—$R^{cf}$, —NH—$C_{2-50}$ alkyl-$N^+R^{ad}R^{be}$—($CH_2CH_2N^+R^{ad}R^{be}$)$_{1-100}$— each of $X_1$, $X_2$, and $X_3$ is each independently —$Y_2$, —O—$Y_2$, —S—$Y_2$, —NH—$Y_2$, —CO—O—$Y_2$, —O—CO—$Y_2$, —CO—NH—$Y_2$, —CO—$NY_1Y_2$, —NH—CO—$Y_2$, —$SO_2$—$Y_2$, —$SO_2$—O—$Y_2$, —$CHY_1Y_2$, or —$NY_1Y_2$;

each of $Y_1$, $Y_2$, and $Y_3$ is each independently —H, -Q-Z—H or —Z—H; in which each Q, independently, is —$R^a$—O—[Si($CH_3$)$_2$—O—]$_{1-100}$-, —$C_{1-2000}$ alkyl-, —$C_{6-40}$ aryl-, —$C_{7-2000}$ alkylaryl-, —$C_{7-2000}$ arylalkyl-, —($C_{1-30}$ alkyl ether)$_{1-100}$-, —($C_{6-40}$ aryl ether)$_{1-100}$-, —($C_{7-2000}$ alkylaryl ether)$_{1-100}$-, —($C_{7-2000}$ arylalkyl ether)$_{1-100}$-, —($C_{1-30}$ alkyl thioether)$_{1-100}$-, —($C_{6-40}$ aryl thioether)$_{1-100}$-, —($C_{7-2000}$ alkylaryl thioether)$_{1-100}$-, —($C_{7-2000}$ arylalkyl thioether)$_{1-100}$-, —($C_{2-50}$ alkyl ester)$_{1-100}$-, —($C_{7-2000}$ aryl ester)$_{1-100}$-, —($C_{8-2000}$ alkylaryl ester)$_{1-100}$-, —($C_{8-2000}$ arylalkyl ester)$_{1-100}$-, —$R^a$—CO—O—($C_{1-30}$ alkyl ether)$_{1-100}$-, —$R^a$—CO—O—($C_{6-40}$ aryl ether)$_{1-100}$-, —$R^a$—CO—O—($C_{7-2000}$ alkylaryl ether)$_{1-100}$-, —$R^a$—CO—O—($C_{7-2000}$ arylalkyl ether)$_{1-100}$-, —($C_{4-50}$ alkyl urethane)$_{1-100}$-, —($C_{14-60}$ aryl urethane)$_{1-100}$-, —($C_{10-2000}$ alkylaryl urethane)$_{1-100}$-, —($C_{10-2000}$ arylalkyl urethane)$_{1-100}$-, —($C_{5-50}$ alkyl urea)$_{1-100}$-, —($C_{14-60}$ aryl urea)$_{1-100}$-, —($C_{10-2000}$ alkylaryl urea)$_{1-100}$-, —($C_{10-2000}$ arylalkyl urea)$_{1-100}$-, —($C_{2-50}$ alkyl amide)$_{1-100}$-, —($C_{7-60}$ aryl amide)$_{1-100}$-, —($C_{8-2000}$ alkylaryl amide)$_{1-100}$-, —($C_{8-2000}$ arylalkyl amide)$_{1-100}$-, —($C_{3-30}$ alkyl anhydride)$_{1-100}$-, —($C_{8-50}$ aryl anhydride)$_{1-100}$-, —($C_{9-2000}$ alkylaryl anhydride)$_{1-100}$-, —($C_{9-2000}$ arylalkyl anhydride)$_{1-100}$-, —($C_{2-30}$ alkylcarbonate)$_{1-100}$-, —($C_{7-50}$ aryl carbonate)$_{1-100}$-, —($C_{8-2000}$ alkylaryl carbonate)$_{1-100}$-, —($C_{8-2000}$ arylalkyl carbonate)$_{1-100}$-, —$R^a$—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$-, —$R^a$—O—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$-, —$R^a$—O—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$-CO—NH—($R^b$ or Ar—$R^b$—Ar)—NH—CO—O—, —$R^a$—O—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$-$R^c$—O—CO—NH—($R^b$ or Ar—$R^b$—Ar)—NH—CO—O—, —$R^a$—NH—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$-, —$R^a$—NH—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$-, —$R^a$—NH—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$-CO—NH—($R^b$ or Ar—$R^b$—Ar)—NH—CO—O—, —$R^a$—NH—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$-, —$R^c$—O—CO—NH—($R^b$ or Ar—$R^b$—Ar)—NH—CO—O—, —$R^a$—O—CO—NH—($R^b$ or Ar—$R^b$—Ar)—NH—CO—NH—($C_{2-50}$ alkyl amide, $C_{7-60}$ aryl amide, $C_{8-2000}$ alkylaryl amide, or $C_{8-2000}$ arylalkyl amide)$_{1-100}$-, —$R^a$—NH—CO—NH—($R^b$ or Ar—$R^b$—Ar)—NH—CO—NH—($C_{2-50}$ alkyl amide, $C_{7-60}$ aryl amide, $C_{8-2000}$ alkylaryl amide, or $C_{8-2000}$ arylalkyl amide)$_{1-100}$-, —$CH_2$—CH(OH)—$CH_2$—($OCH_2CH_2$)$_{1-100}$—$OCH_2CH(OH)$—$CH_2$, —$CH_2$—CH(OH)—$CH_2$—$N^+HR^a$—($CH_2CH_2N^+R^aR^b$)$_{1-100}$—$CH_2CH_2N^+HR^a$—$CH_2CH(OH)CH_2$—, or —$CH_2CH_2$—$N^+R^aR^b$—($CH_2CH_2N^+R^aR^b$)$_{1-100}$—$R^c$—; and each Z, independently, is —$R^a$—, —$R^a$—Ar—, —Ar—$R^a$—, or —Ar—; and $V_1$ is —OH, —SH, —$NH_2$, —NHOH, —$SO_3H$, —$OSO_3H$, —$CO_2H$, —$CONH_2$, —$CONHNH_2$, —CH($NH_2$)—$CO_2H$, —NH—$CH_2$—$CO_2H$, —$P(OH)_3$, —$PO(OH)_2$, —O—$PO(OH)_2$, —O—PO(OH)—O—$PO(OH)_2$, —O—$PO(O^-)$—O—$CH_2CH_2NH_3^+$, —O—$PO(O^-)$—O—$CH_2CH_2$—$N^+(CH_3)_3$, -glycoside, -oligosaccharide, —CO-glycoside, —CO-oligosaccharide, —$OCH_3$, —$OCH_2(CHOH)_4$—$CH_2OH$, —$OCH_2(CHOH)_2$—$CH_2OH$, —CO—$OCH_2(CHOH)_4$—$CH_2OH$, —$C_6H_3(OH)_2$, —$N(CH_2CO_2H)_2$, —CO—$N(CH_2CO_2H)_2$, —CO—NH—$C(CH_2CH_2CO_2H)_3$, —CO—NH—$C(CH_2CH_2OH)_3$, —[$CH_2$—CH($CO_2R^a$)]$_{1-100}$—H, —O—($CH_2CH_2O$)$_{1-100}$—H, —$NH_3^+$, —$N^+H_2R^a$, —$N^+HR^aR^b$, or —$N^+R^aR^bR^c$;

wherein each of $R^a$, $R^b$, and $R^c$ are each independently $C_{1-20}$ linear or branched alkyl;

Ar is aryl;

W is hydroxyl or amino;

p and s each independently is 0-20; and when $P_2$ is —NH—$C_{2-50}$ alkyl-$N^+R^{ad}R^{be}$—($CH_2CH_2N^+R^{ad}R^{be}$)$_{1-100}$—$R^{ef}$ or —O—$C_{2-50}$ alkyl-$N^+R^{ad}R^{be}$—($CH_2CH_2N^+R^{ad}R^{bc}$)$_{1-100}$—$R^{cf}$, it is understood the $P_2$ moiety comprises at least two charged moieties per arm.

In the compound of Formula (III), Fn may be $C_{70}$, $C_{76}$, $C_{78}$, $C_{82}$, $C_{84}$, $C_{92}$, (methano)$_nC_{70}$, (pyrrolidino)$_nC_{70}$, (methano)$_mC_{84}$, (pyrrolidino)$_mC_{84}$, La@$C_y$, Ho@$C_y$, Gd@$C_y$, Er@$C_y$, (methano)$_m$La@$C_y$, (methano)$_m$Ho@$C_y$, (methano)$_m$Gd@$C_y$, (methano)$_m$Er@$C_y$, (pyrrolidino)$_m$La@$C_y$, (pyrrolidino)$_m$Ho@$C_y$, (pyrrolidino)$_m$Gd@$C_y$, or (pyrrolidino)$_m$Er@$C_y$, wherein n is 2-10, m is 1-10, and y is 60, 74, or 82. Specifically, Fn is (methano)$_nC_{70}$, (pyrrolidino)$_nC_{70}$, (methano)$_mC_{84}$, (pyrrolidino)$_mC_{84}$, (methano)$_m$La@$C_y$, (methano)$_m$Ho@$C_y$, (methano)$_m$Gd@$C_y$, (methano)$_m$Er@$C_y$, (pyrrolidino)$_m$La@$C_y$, (pyrrolidino)$_m$Ho@$C_y$, (pyrrolidino)$_m$Gd@$C_y$, or (pyrrolidino)$_m$Er@$C_y$.

In the compound of Formula (III), $E_1$ may be $Y_1$,$Y_2$-amino, $Y_2$-amino, ($Y_1$,$Y_2$-alkyl)-amino, $Y_1$,$Y_2$-ethylenediamino, (dihydroxymethyl)alkylamino, ($X_1$,$X_3$-aryl)amino, ($Y_1$,$Y_2$,$Y_3$-alkyl)amino, ($Y_1$,$Y_2$,$Y_3$-aryl)amino, dihydroxyalkylamino, (trihydroxyalkyl)alkylamino, or (dicarboxyalkyl)amino; and p is 1-4. Specifically, each of $X_1$ and $X_2$ is hydrogen.

In the compound of Formula (III), $V_1$ may be hydrogen, $C_{1-2000}$ alkyl, $C_{6-40}$ aryl, or $C_{7-2000}$ arylalkyl, optionally substituted with —OH, —SH, —$NH_2$, —NHOH, —$SO_3H$, —$OSO_3H$, —$CO_2H$, —$CONH_2$, —$CONHNH_2$, —CH($NH_2$)—$CO_2H$, —NH—$CH_2$—$CO_2H$, —, —$NH_2CH_2O$)$_{1-100}$—H, —$N^+R^aR^bR^c$, or —NH—($CH_2CH_2N^+R^aR^b$)$_{1-100}$—$R^c$. Specifically, $V_1$ is —$N^+R^aR^bR^c$ or —NH—($CH_2CH_2N^+R^aR^b$)$_{1-100}$—$R^c$; the counter anion is chloride, bromide, iodide, triiodide, sulfate, pyrosulfate, bisulfate, sulfite, bisulfite, thiosulfate, nitrate, nitrite, phosphate, azide, thiocyanate, selenocyanate, or acetate. More specifically, $E_1$-$V_1$ is hydroxy or amino; and p is 0-20.

In the compound Formula (III), U may be —[C═C(CN)$_2$].

In the compound Formula (III), $P_2$ may be —NH—$C_{2-50}$ alkyl-$N^+R^{ad}R^{be}$—($CH_2CH_2N^+R^{ad}R^{be}$)$_{1-100}$-$R^{cf}$, or —O—$C_{2-50}$ alkyl-$N^+R^+R^{ad}R^{be}$—($CH_2CH_2N^+R^{ad}R^{be}$)$_{1-100}$-$R^{ef}$; the counter anion is chloride, bromide, iodide, triiodide, sulfate, pyrosulfate, bisulfate, sulfite, bisulfite, thiosulfate, nitrate, nitrite, phosphate, azide, thiocyanate, selenocyanate, or acetate.

By the term "alkyl" is meant a straight-chain or branched hydrocarbon. An alkyl group may also contain one or more double bond or triple bond and the cyclic alkyl groups may contain one or more heteroatoms, which are, typically, nitrogen, oxygen, or sulfur. Examples of an alkyl group include, but are not limited to, methyl, ethyl, propyl, isopropyl, butyl, isobutyl, tert-butyl, amyl, pentyl, hexyl, heptyl, octyl, nonyl, decyl, pentadecyl, icosyl, allyl, 2-butenyl, 2-pentenyl, 3-hexenyl, 4-decenyl, 5-nonadecenyl, 2-butnyl, 3-octnyl, 5-octadecnyl, cyclopropyl, cyclopentyl, cyclohexyl, cycloheptyl, adamantyl, norbornyl, isobornyl, cyclopentyl-methyl, cyclohexylmethyl, 1- or 2-cyclohexylethyl, cyclo-pentenyl, cyclohexenyl, cycloheptenyl, cyclo-octenyl, tetra-hydrofuranyl, tetrahydropyranyl, piperidinyl, morpholino and pyrrolindinyl groups. Exemplary alkyl groups are $C_1$ to $C_{100}$ alkyl groups, preferably $C_1$ to $C_{30}$ alkyl groups.

As used herein, the term "aryl" refers to aromatic rings. These moieties may be fused rings and may be fused with aryl or heteroaryl as defined below. Fused rings are rings that share a common carbon-carbon bond. Typically, aryl groups include phenyl, naphthyl, biphenyl, indazolyl, phenanthryl, and anthracyl. Exemplary aryl groups are $C_6$ to $C_{100}$ aryl groups, preferably $C_6$ to $C_{100}$ aryl groups.

By the term "heteroaryl" is meant an aromatic ring that contains one or more heteroatoms as defined above. It may be a fused ring. Examples of heteroaryl groups include pyridyl, pyrazinyl, pyrimidyl, furyl, pyrrolyl, thienyl, thiazolyl, oxazolyl, imidazolyl, coumarinyl, indolyl, benzofuranyl, benzthiazolyl, benzothienyl, and benzothiadiazolyl. Heteroaryl groups preferably include nitrogen, sulfur, or oxygen, preferably 1 to 5 heteroatoms.

The term "metal ion" includes a Cu, Mn, Fe, Co, Ni, Ru, Rh, Pd, Pt, Ti, Si, or Zr ion.

The term "an amino or amide group-containing antibiotic molecule" includes vancomycin, imipenem, gentamicin, tetracycline, tigecycline, minocycline, meropenem, ceftazidime, ciprofloxacin, norfloxacin, moxifloxacin, amikacin, kanamycin, aminopenicillin, tobramycin, doripenem, amoxicillin, or ampicillin.

As used herein, the term "halo" includes fluoro, chloro, bromo, and iodo.

The compounds include their pharmaceutically acceptable salts, if applicable. Such a salt can be formed between a positively charged substituent (e.g., amino) in a fused pyrazolyl compound and a negatively charged counterion (e.g., chloride, bromide, iodide, triiodide, sulfate, pyrosulfate bisulfate, sulfite, bisulfite, thiosulfate, nitrate, nitrite, phosphate, azide, thiocyanate, selenocyanate, or acetate). Likewise, a negatively charged substituent (e.g., carboxylate) in a fused pyrazolyl compound can form a salt with a positively charged ion (e.g., sodium ion, potassium ion, magnesium ion, calcium ion, or an ammonium cation such as tetramethylammonium ion).

By the term oligosaccharide is meant a repeating saccharide subunit in a number of 2-20.

Also included are pharmaceutical compositions comprising the compounds of formulas I, II, and III. The use of such a nano-$C_{60/70}$PS or $C_{60/70}$PS-CB-Abx compound for the manufacture of a medicament for treating localized infections, including wound infections, burn infections, acne, soft-tissue infections, oral and dental infections, leishmaniasis, mycobacterial infection, keratitis, otitis media, sinusitis, localized tuberculosis, and fasciitis. Additional localized infections such as gastric *H. pylori* infections, intra-abdominal abscess, cystitis, urinary tract infections, genital tract infections, osteomyelitis, onychomycosis, viral infections can be treated, as well as blood sterilization. Skin cancers and other localized tumors may also be treated.

In an aspect, a method for treating wound infections, burn infections, acne, soft-tissue infections, oral and dental infections, leishmaniasis, mycobacterial infection, keratitis, otitis media, sinusitis, localized tuberculosis, fasciitis, gastric *H. pylori* infections, intra-abdominal abscess, cystitis, urinary tract infections, genital tract infections, osteomyelitis, onychomycosis, virus infections, as well as blood sterilization, skin cancers, or other localized tumors by administering to a patient a pharmaceutical composition containing an effective amount of a nano-$C_{60/70}$PS or $C_{60/70}$PS-CB-Abx compound as described herein. An effective amount is defined as the amount which is required to confer a therapeutic effect on the treated patient, and is typically determined based on age, surface area, weight, and condition of the patient. The interrelationship of dosages for animals and humans (based on milligrams per meter squared of body surface) is described in the art. Body surface area may be approximately determined from height and weight of the patient. An effective amount of a nano-$C_{60/70}$PS or $C_{60/70}$PS-CB-Abx compound can range from about 1.0 mg/kg to about 150 mg/kg. Effective doses will also vary, as recognized by those skilled in the art, dependent on route of administration, excipient usage, and the possibility of co-usage with other therapeutic treatments including use of other antibacterial agents and radiation therapy.

The pharmaceutical composition may be administered via the parenteral route, including orally, topically, subcutaneously, intraperitoneally, intramuscularly, and intravenously. Examples of parenteral dosage forms include aqueous solutions of the active agent, in an isotonic saline, 5% glucose or other well-known pharmaceutically acceptable excipient. Solubilizing agents such as cyclodextrins, or other solubilizing agents well-known to those familiar with the art, can be utilized as pharmaceutical excipients for delivery of the therapeutic compounds.

A nano-$C_{60/70}$PS or $C_{60/70}$PS-CB-Abx compound can be formulated into dosage forms for other routes of administration utilizing conventional methods. For example, it can be formulated in a capsule, a gel seal, or a tablet for oral administration or in a gel, a cream, or in a patch form for topical administration. Capsules may contain any standard pharmaceutically acceptable materials such as gelatin or cellulose. Tablets may be formulated in accordance with conventional procedures by compressing mixtures of a nano-$C_{60/70}$PS or $C_{60/70}$PS-CB-Abx compound with a solid carrier and a lubricant. Examples of solid carriers include starch and sugar bentonite. The nano-$C_{60/70}$PS or $C_{60/70}$PS-CB-Abx compound can also be administered in a form of a hard shell tablet or a capsule containing a binder, e.g., lactose or mannitol, a conventional filler, and a tableting agent.

The invention is further illustrated by the following non-limiting examples.

EXAMPLES

Example 1: General Description of Method of Synthesis and Efficacy

Figure 1B:
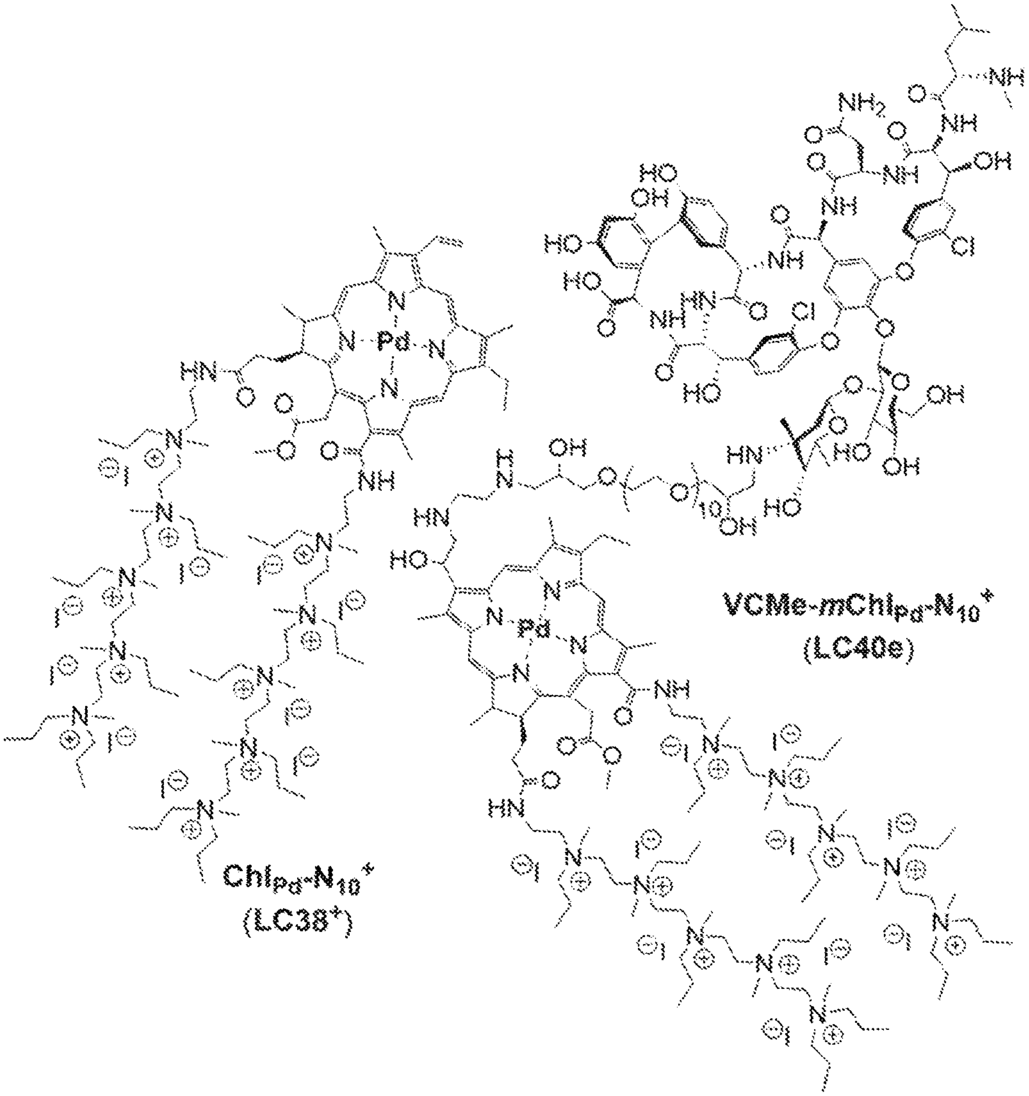

Nano-$C_{60/70}$PS compounds and $C_{60/70}$PS-CB-Abx conjugates can be prepared by a short sequence of synthesis. Specifically, the methods described herein utilize a key starting material, i.e., pheophytin (Phe) and chlorophyll (Chl), as shown in FIGS. 1A and 1B. The resulting new water-soluble $Chl_{pd}$-$N_{10}^+$ (LC38$^+$), $Chl_{pd}$-($C_{70}$>)$N_{10}^+$ (LC41), and covalent vancomycin conjugates VCMe-m$Chl_{pd}$-$N_{10}^{+}$ (LC40e) and VCMe-m$Chl_{pd}$-$(C_{70}{>})N_{10}^{+}$ (LC42) compounds are applied as either aPDT, nano -$C_{60/70}$-aPDT, or combinatorial $C_{60/70}$-aPDT-CB-Abx drugs. The structural moiety combination allows these nanodrugs to be photoactive in the light wavelength ranges of 320-400-nm for a $C_{60}$ cage, 380-500-nm for a $C_{70}$ cage, and 630-700-nm for a light-harvesting chlorophyll antenna moiety for the aPDT practice.

One of the main problems existing in current aPDT practice is the low photostability of common photosensitizers that limits an extended period of treatment. In contrast, nano-$C_{60/70}$PS compounds are highly photostable due to their rapid photoinduced intramolecular energy- and electron ($e^{-}$)-transfers from the light-harvesting $e^{-}$-donating chlorophyll antenna moiety to the $e^{-}$-accepting nano-carbon $C_{60}$ or $C_{70}$ cage moiety giving stabilization and manifest little photobleaching. This effect allows many irradiation cycles and the extended time length in performing aPDT.

In terms of photodynamic photomechanism, nano-$C_{60/70}$PS compounds are able to enhance Type-I ($O_2^{-}$ and HO·) and activate novel Type-III (transferrable e pathway) photochemistry mechanism toward $O_2$-independent aPDT for anaerobic infections, where the efficacy of aPDT can be limited by fast depletion of oxygen in deeply localized infections. Without being held to theory, it is believed that that radically induced cell damage via a Type-I (HO·) mechanism is more powerful in aPDT than Type-II ($^{1}O_2$) mechanism.

By using $Chl_{pd}$-$(C_{70}{>})N_{10}^{+}$ (LC41, $C_{70}$PS, FIG. 1A) as an example, Type-I photochemistry involves the formation of $(Chl_{pd})^{+\cdot}$—$(C_{70}{>})^{-}\cdot N_{10}^{+}$ and $Chl_{pd}$-$(C_{70}{>})^{-}\cdot N_{10}^{+}$ radical anion ($C_{70}PS^{-}\cdot$) [eq. (1)], upon photo-excitation and $e^{-}$-transfer from $I^{-}$ or $e^{-}$-donating salts. $C_{70}PS^{-}\cdot$ can further transfer an $e^{-}$ to $O_2$, via $C_{70}{>}$ cage, forming $O_2^{-}\cdot$ Superoxide dismutase can transform $O_2^{-}\cdot$ to $H_2O_2$ that further reacts with a second $C_{70}PS^{-}\cdot$ to form HO. [eq. (2)]. All equations of Type-I and Type-III photochemistry are summarized as follows.

Type-I Photochemistry:

$$Chl_{pd}\text{-}(C_{70}{>})N_{10}^{+}(C_{70}PS)+h\nu \rightarrow (Chl_{pd})^{+\cdot}\text{—}(C_{70}{>})^{-}\cdot N_{10}^{+}(A);$$

$$A+I^{-} \rightarrow Chl_{pd}\text{-}(C_{70}{>})^{-}\cdot N_{10}^{+}(C_{70}PS^{-}\cdot) \quad (1)$$

$$C_{70}PS^{-}\cdot+O_2 \rightarrow Chl_{pd}\text{-}(C_{70}{>})N_{10}^{+}(C_{70}PS)+O_2^{-}\cdot;$$

$$O_2^{-}\cdot+e^{-}+2H^{+} \rightarrow H_2O_2;$$

$$H_2O_2+C_{70}PS^{-}\cdot \rightarrow Chl_{pd}\text{-}(C_{70}{>})N_{10}^{+}(C_{70}PS)+HO\cdot+HO^{-} \quad (2)$$

New Type-III Photochemistry:

$$(Chl_{pd})^{+\cdot}\text{—}(C_{70}{>})^{-}\cdot N_{10}^{+}(A)+I^{-} \rightarrow Chl_{pd}\text{-}(C_{70}{>})^{-}\cdot N_{10}^{+}(C_{70}PS^{-}\cdot)+\tfrac{1}{2}I_2;$$

$$Chl_{pd}\text{-}(C_{70}{>})^{-}\cdot N_{10}^{+}(C_{70}PS^{-})+h\nu \rightarrow (Chl_{pd})^{+\cdot}\text{-}(C_{70}{>})^{-2}N_{10}^{+} \quad (3)$$

$$(Chl_{pd})^{+\cdot}\text{-}(C_{70}{>})^{-2}N_{10}^{+}+I^{-}+h\nu \rightarrow \tfrac{1}{2}I_{+}Chl_{pd}\text{-}(C_{70}{>})^{-2}N_{10}^{+};$$

$$Chl_{pd}\text{-}(C_{70}{>})^{-2}N_{10}^{+} \rightarrow Chl_{pd}\text{-}(C_{70}{>})N_{10}^{+}(C_{70}PS)+2e^{-};$$

$$2e^{-}+2Fe^{+3} \leftrightarrow 2Fe^{+2} \quad (4)$$

Without being held to theory, it is proposed that $Chl_{pd}$-$(C_{70}{>})^{-}\cdot N_{10}^{+}$ ($C_{70}PS^{-}\cdot$) [eq. (3)] and $Chl_{pd}$-$(C_{70}{>})^{-2}N_{10}^{+}$ [eq. (4)] can directly transfer e into bacterial cells, especially considering the high reductive states of $(C_{70}{>})^{-2}$. This influx of e may over-stimulate the $e^{-}$-transfer chains of the bacterial cells leading to destruction or $e^{-}$-reduction of the iron ($Fe^{+3}$)-sulfur clusters. The resulting $e^{-}$-reduced ferrous iron ($Fe^{+2}$) or $Fe^{+}$ released from the iron-sulfur clusters can catalyze an internal Fenton reaction inside the bacteria that leads to the cell death from internal oxidative stress. This either directly damage DNA or indirectly oxidize the deoxynucleotide pool, which is subsequently incorporated into DNA. The mechanism can be thought of as the photoinduced pumping of e into bacterial cells, causing them to "commit suicide" in a similar manner to the action of bactericidal antibiotics.

Synthesis of new $Chl_{pd}$-$N_{10}^{+}$ ($LC38^{+}$), $Chl_{pd}$-$(C_{70}{>})N_{10}^{+}$ (LC41), and covalent vancomycin conjugates VCMe-m$Chl_{pd}$-$N_{10}^{+}$ (LC40e) and VCMe-m$Chl_{pd}$-$(C_{70}{>})N_{10}^{+}$ (LC42) as new either aPDT, nano-$C_{60/70}$-aPDT, or $C_{60/70}$-aPDT-CB-Abx drugs was carried out using the procedure described in FIG. 1A with the structures including FIG. 1B. In the structural design, decacationic moiety was covalently attached to either chlorophyll (Chl) or mesochlorophyll (mChl) ring. Conjugation of a vancomycin (VCM) moiety to the mesochlorophyll ring was linked by a water-soluble poly(ethylene glycol) chain with a separation distance between these two moieties appropriate to effect the simultaneous colocalized delivery of nano-$C_{60/70}$PS and VCM without interference on each other's intrinsic aPDT and antibiotic activities, respectively.

Preparation of $Pd^{+2}$-chlorin [$Chl_{pd}$-$N_{10}^{+}$ ($LC38^{+}$) and $Chl_{pd}$-$(C_{70}{>})N_{10}^{+}$ (LC41)] and $Pd^{+2}$-mesochlorin [m$Chl_{pd}$-$N_{10}^{+}$ and m$Chl_{pd}$-$(C_{70}{>})N_{10}^{+}$] derivatives that contain two pentacationic chains, providing PSs with a total of ten cationic charges in each molecule. Owing to the negatively charged cell surface of many microorganisms, a relatively large number of 10 cations may allow sufficiently effective cell surface interactions to enhance aPDI drug targeting. Moreover, some analogous derivatives were further covalently conjugated with the antibiotic vancomycin (VCM), leading to such as VCMe-m$Chl_{pd}$-$N_{10}^{+}$ (LC40e) and VCMe-m$Chl_{pd}$-$(C_{70}{>})N_{10}^{+}$ (LC42), with the goal of introducing a moiety that could target D-Ala-D-Ala residues present on the cell walls of Gram-positive bacteria.

Figure 2A:
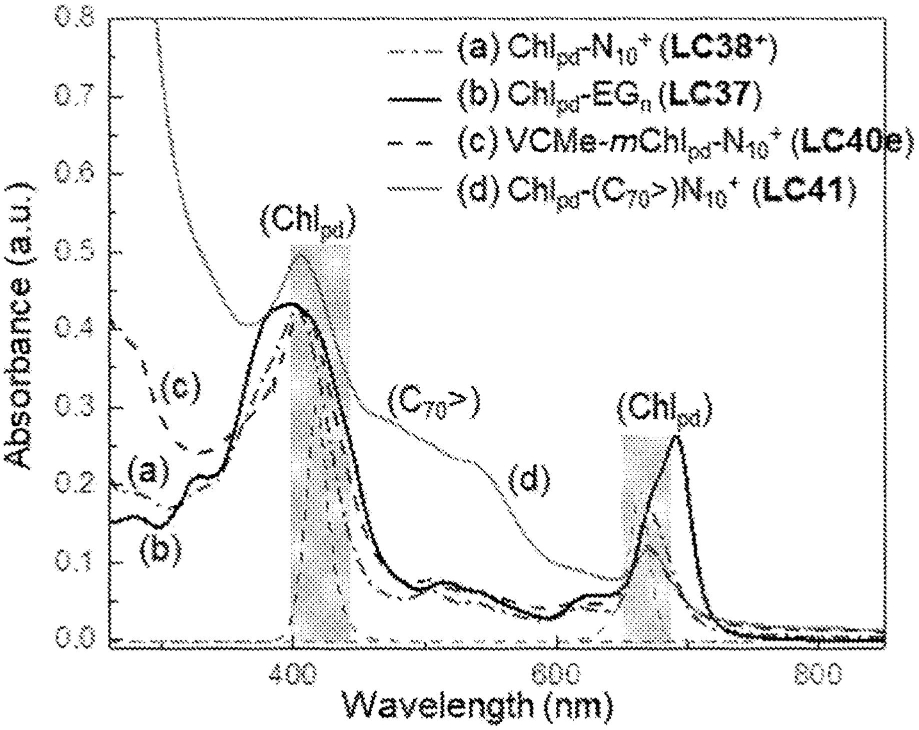
FIG. 2. (A) UV-vis spectra of (a) LC38$^+$, (b) LC37, (c) LC40e and (d) LC41 showing broad absorption in conjugation with $C_{70}$> and the emission spectrum of blue and red lights. (B) Efficient $^1O_2$ (b) and $O_2^{-}\cdot$ (d) production by LC41 detected by fluorescent probes. Time-dependent fluorescent emission intensity of ABMA, as the synthetic $^1O_2$ trapping probe with the photoexcitation at $\lambda_{ex}$ 380 nm and emission at $\lambda_{em}$ 428 nm, using the aPDI agent of (C) LC38$^+$ and (D) LC40e, in a concentration of 20 μm (DMF-$H_2O$/1:9), under irradiation of (a) white LED (2.0 W), (b) 400-nm LED (320 mW), and (c) 650-nm laser (200 mW) light. ABMA was also applied alone under the same irradiation condition using (d)
Figure 2B:
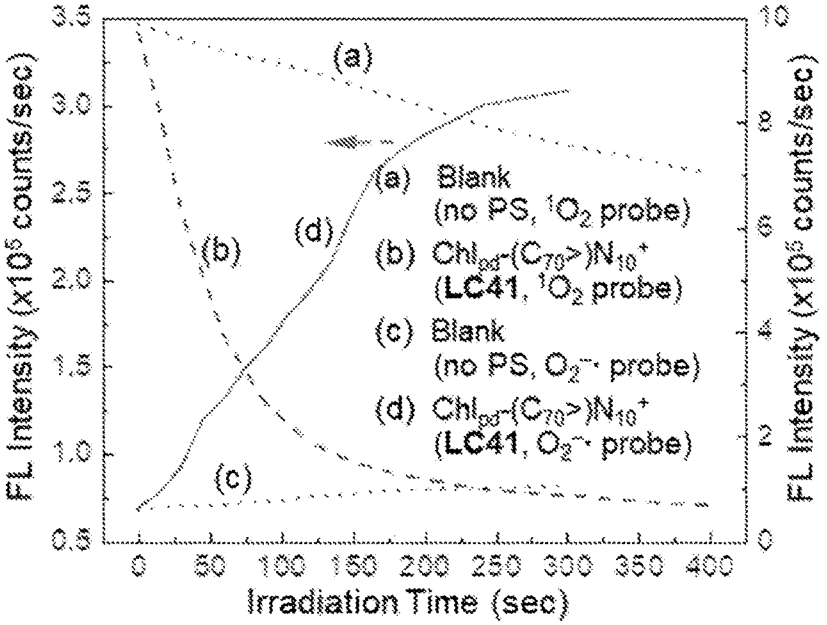
Figure 2C:
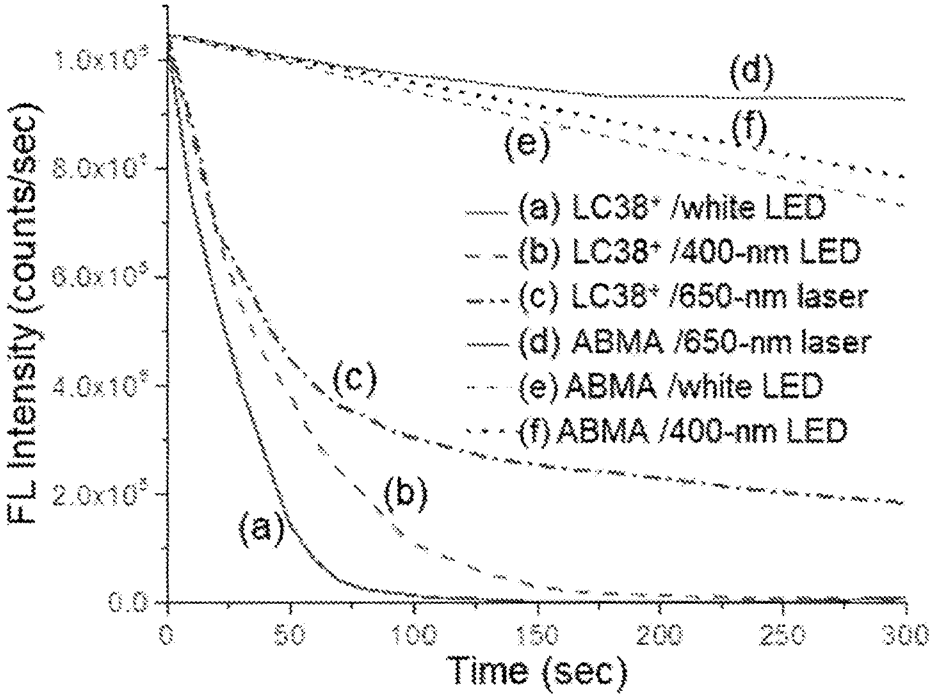
Figure 2D:
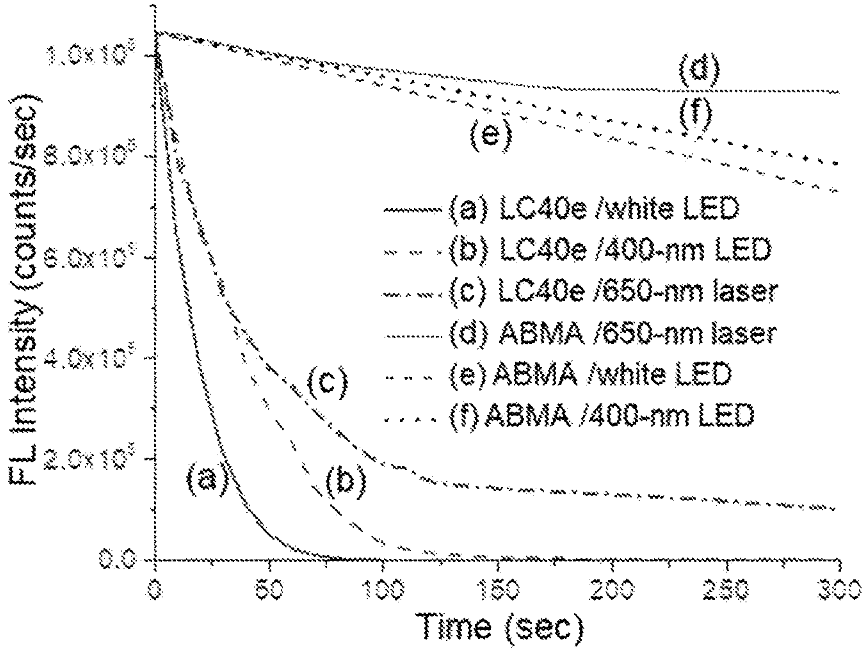

Derivatives of nano-$C_{60/70}$PS LC41 and $C_{60/70}$PS-CB-Abx conjugate LC42, shown in FIG. 1A, are able to co-produce $^{1}O_2$ (Type-II) and highly reactive HO (formed from $O_2^{-}\cdot$ in subsequent conditions) in Type-I photosensitizing reactions, upon irradiation at either UVA, white, or red wavelengths. Incorporation of a m$Chl_{pd}$ antenna in LC40 (FIG. 2Ac) and LC41 (FIG. 2Ad) structures led to increase of red absorption at 660 nm. Accordingly, both $^{1}O_2$ (FIG. 2Bb) and $O_2^{-}\cdot$ (FIG. 2Bd) production efficiency of LC41 were found to be high upon white light irradiation. In cases of $LC38^{+}$ or LC40e, we applied a highly fluorescent tetrasodium α,α'-(anthracene-9,10-diyl)bis(methylenemalonic acid salt) (ABMA) as a reactive probe in the solution detection of singlet oxygen ($^{1}O_2$). Facile chemical trapping of $^{1}O_2$ by ABMA molecules results in formation of the corresponding non-fluorescent 9,10-endoperoxide product ABMA-$O_2$. Accordingly, the effective amount of fluorescence emission loss in intensity at 428 nm, owing to the chemical translation in structure, can be correlated to the same molar quantity of $^{1}O_2$ produced by either $LC38^{+}$ or LC40e. Production of $^{1}O_2$ was originated from the intersystem crossing process from the singlet excited state of $^{1}(Chl_{pd}\text{-}N_{10}^{+})^{*}$ and $^{1}(\text{VCMe-m}Chl_{pd}\text{-}N_{10}^{+})^{*}$ to their corresponding triplet excited state of $^{3}(Chl_{pd}\text{-}N_{10}^{+})^{*}$ and $^{3}(\text{VCMe-m}Chl_{pd}\text{-}N_{10}^{+})^{*}$, respectively, followed by the Type-II triplet energy transfer to $O_2$. Consequently, under all three light sources of white LED, 400-nm LED, and 650-nm laser used for the irradiation of $LC38^+$ and LC40e, rapid loss of the fluorescent emission intensity of ABMA was observed in FIGS. 2Ca,b,c and 2Da,b,c, respectively. The data are indicative of an efficiently rapid and higher production quantity of $^1O_2$ for LC40e than $LC38^+$ under the same light and fluence exposure. These photophysical characteristics should lead to slightly better performance of LC40e in aPDI efficacy than $LC38^+$.

Figure 3A:
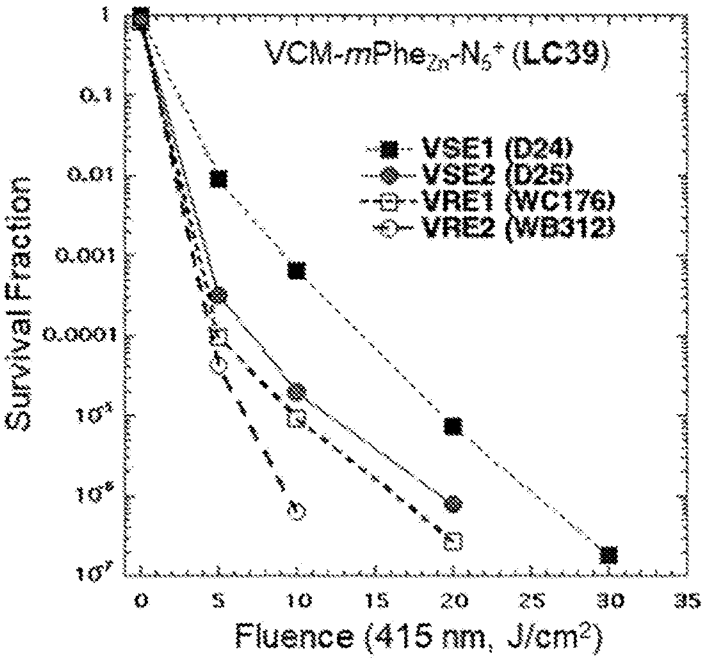
Figure 3B:
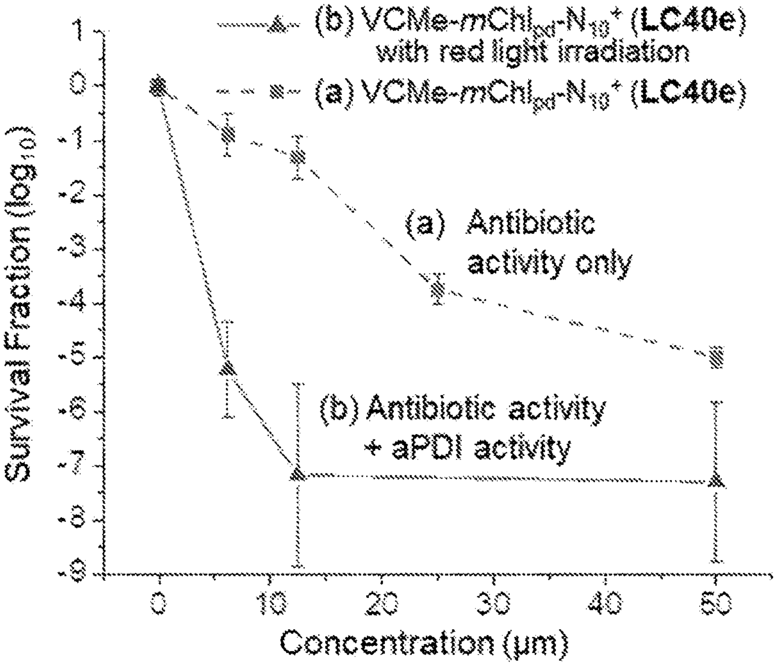

By using VCM-mPhez$_n$-$N_5^+$ (LC39) as an example of demonstration, we observed excellent aPDT effect (FIG. 3A, 415 nm irradiation) against VCM-resistant and sensitive strains of *E. fecium* (VSE) at a 50-nM concentration. We also demonstrated the efficacy of LC40e mediated aPDI of *A. baumannii* at the concentration of 12.5 μM under red light (660 nm) irradiation (115 J/cm$^2$) (FIG. 3Bb). All *A. baumannii* CFUs were inactivated (>6-$\log_{10}$ CFU reduction). At this concentration of LC40e, it also induced about 1.5-$\log_{10}$ CFU dark toxicity to *A. baumannii* cells. Without red-light irradiation, LC40e exhibited normal antibiotic activity of a 4-$\log_{10}$ CFU killing, consistent with its MIC (μg/mL) efficacy value of 2.0 against MRSA (similar to that of vancomycin itself). Apparently, an additional 3-$\log_{10}$ CFU increase in the inactivation of bacteria was perceived only by the combination of antibiotics and aPDT. This representative data substantiated our approach of combinatorial antimicrobial therapy by controlled colocalized delivery of nano-$C_{60/70}$PS and covalently-bonded antibiotics as $C_{6000}$PS-CB-Abx conjugates for further enhanced antimicrobial efficacy.

Figure 3C:
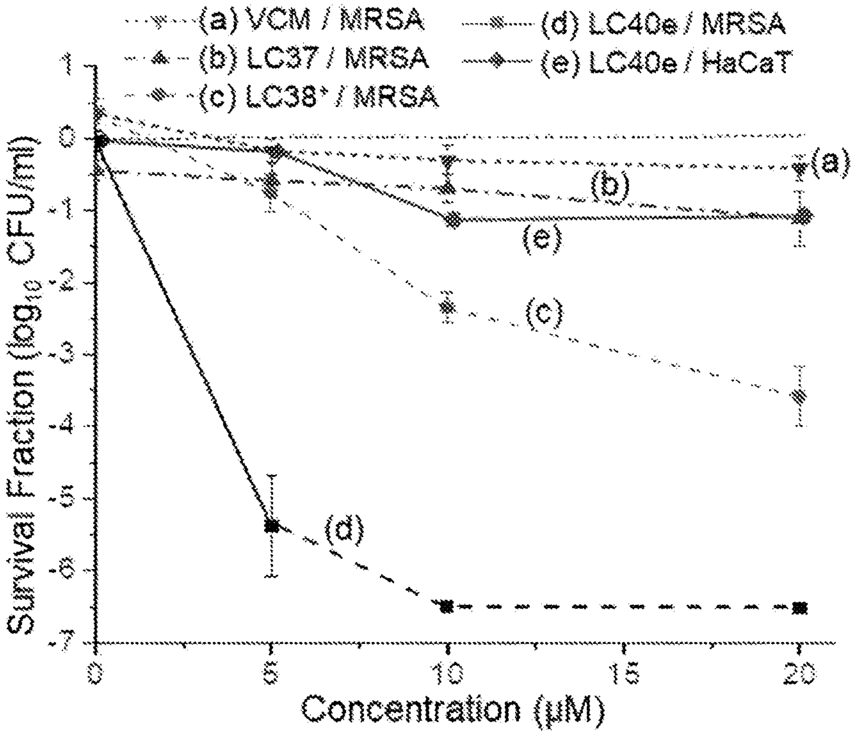
Figure 3D:
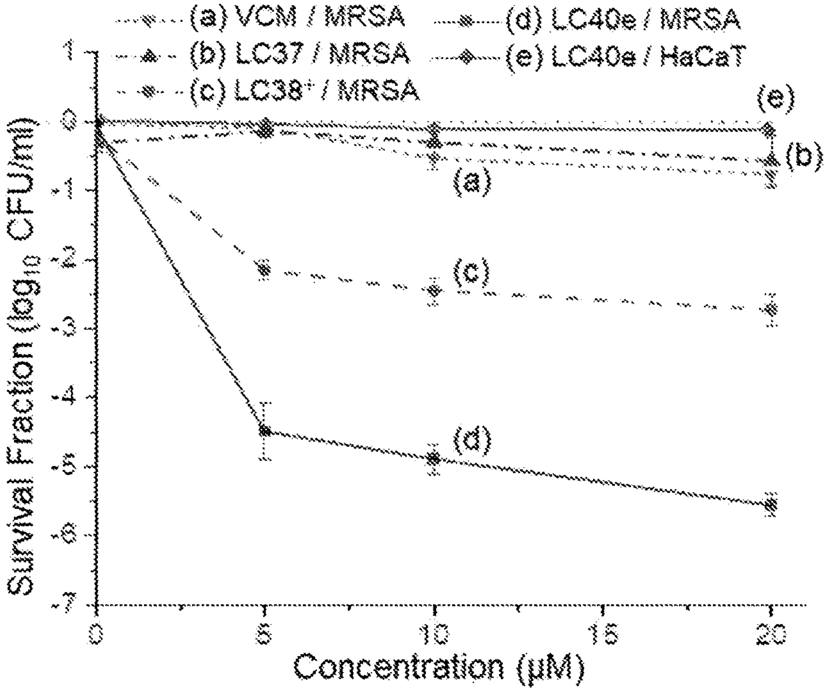
Figure 3E:
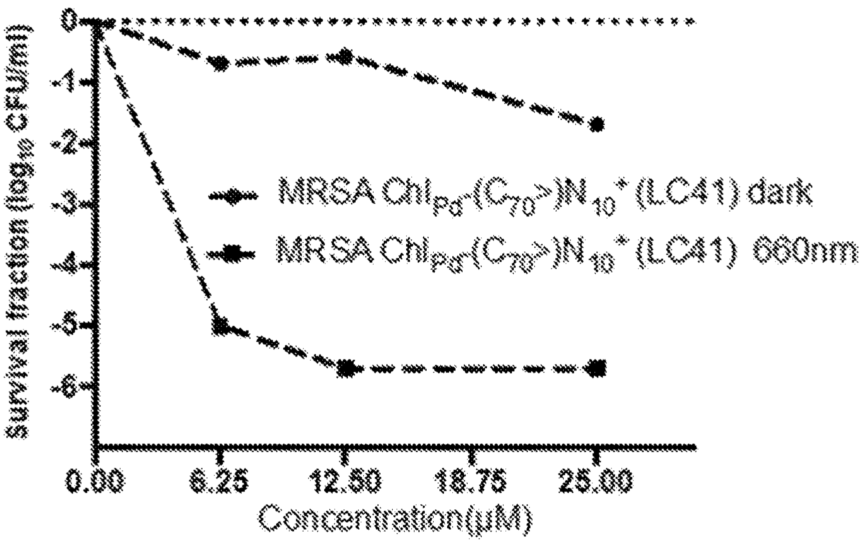

In addition, FIGS. 3C and 3D display photocytotoxicity efficacies of LC37, $LC38^+$, and LC40e against MRSA (multidrug resistant *S. aureus*, strain IQ0064) cells in vitro. As a control, vancomycin alone at the equivalent dose presented negligible effect on viability of MRSA cells, as shown in FIGS. 3Ca and 3Da. This is owing to the fact that all aPDI experiments were carried out within a relatively short period of time (1480 min) well below the kinetic rate required for completing the antibiotic activity. Therefore, a VCM moiety was applied for enhancing its targeting ability to MRSA cells at the initial stage of aPDI. We found that MRSA cells were susceptible to light mediated killing by $LC38^+$, and LC40e having 10 cationic charges. The trend was obvious when the comparison of survival fraction $\log_{10}$ CFU values (P<0.001) obtained for noncationic LC37 (FIGS. 3Cb and 3Db) and decacationic $LC38^+$ (FIGS. 3Cc and 3Dc) were made to show an increased photokilling rate for the latter under the same conditions of light exposure, irradiation fluence, and drug concentration at both 405- and 660-nm photoexcitation. With an additional covalent attachment of a VCM moiety to the molecular structure of $LC38^+$ with a $EG_n$ linker to result in the agent structure of LC40e, large enhancement of photokilling efficacy with higher $\log_{10}$ CFU reduction values (P<0.001) was detected in FIGS. 3Cd ($\lambda_{ex}$ 660 nm) and 3Dd ($\lambda_{ex}$ 405 nm), where complete eradication (>6.5-$\log_{10}$ CFU reduction, FIG. 3Cd) was possible using a concentration of 10-20 μM with a 115-J/cm$^2$ fluence of 660-nm light. In the case of 405-nm irradiation, a 5.0-$\log_{10}$ efficacy was achieved at the same concentration range with a lower fluence exposure of 20 J/cm$^2$. For $Chl_{pd}$-($C_{70}$>)$N_{10}^+$ (LC41), MRSA CFUs were completely eradicated at the concentration of 12.5 μM (FIG. 3E). At the same concentration, $Chl_{pd}$-($C_{70}$>)$N_{10}^+$ exhibited ~1.0-$\log_{10}$ CFU dark toxicity to MRSA cells.

We demonstrated the binding characteristics of LC37, $LC38^+$, and LC40e using the fluorescent image evaluation technique of confocal microscopy (CM). Under CM condition of 405-nm irradiation (LED light, 30 mW), all LC37, $LC38^+$, and LC40e exhibited two similar FL emission bands centered at 490 (minor, blue) and 670 nm (major, red). Since the red emission can only be possible to occur from chlorin- and meso-chlorin-based agents, it should be more accurate to access the relative targeting quantity on MRSA cells. As a result, no red emission was detectable on the sample plate with MRSA cells alone as expected. The red emission became slightly visible on the sample plate with LC37-pretreated MRSA cells and turned clearly detectable with $LC38^+$-pretreated MRSA cell samples. It was significantly enhanced on LC40e-pretreated MRSA cell samples showing the relative cell affinity order of LC40e>$LC38^+$>>LC37. Overlay of bright field, red FL emission (640-780 nm), and blue FL emission (450-550 nm) images provided clear accounts to conclude the successfully enhanced attachment of LC40e on MRSA cells by a combined application of decacationic charges and a MRSA-targeting VCM moiety.

Example 2: Preparation of Pheophytin-α

Chlorella powder (broken cell wall, 120 g) was firstly washed with water and ethanol-water (1:1, v/v) to remove polar materials, and then extracted twice with a mixture of dichloromethane-ethanol (1:2, v/v, 500 mL) to offer raw chlorophyll as green semi-solid after evaporating the solvents, which were then stirred in a mixture of HCl (1.0 N)-ethanol (1:1, v/v) at r.t. to afford pheophytin mixtures. Purification was carried out by column chromatography (neutral alumina) using a gradient eluent in a composition from hexane-dichloromethane (7:3, v/v) to 100% dichloromethane. A major green band was collected to afford green viscous semi-solids (5.8 g) of pheophytin-α. Spectroscopic data: FT-IR (KBr) $\nu_{max}$ 3437 (s), 3397 (s), 2950 (s), 2925 (s), 2867 (m), 1736 (s), 1701 (s), 1618 (m), 1581 (w), 1553 (m), 1535 (w), 1499 (m), 1460 (m), 1451 (m), 1438 (m), 1400 (w), 1378 (m), 1365 (m), 1347 (m), 1296 (w), 1223 (m), 1159 (m), 1123 (w), 1198 (w), 1059 (w), 1033 (m), 986 (m), 963 (m), 910 (w), 896 (w), 842 (w), 814 (w), 785 (w), 770 (w), 751 (w), 730 (m), 719 (w), 672 (m), and 605 (m) cm$^{-1}$; UV-vis (dichloromethane, 1.0×10$^{-5}$ M) $\lambda_{max}$ (ε) 405 nm (2.82×10$^4$), 504 nm (4.51×10$^3$), 539 nm (2.72×10$^3$), 610 nm (2.43×10$^3$), 668 nm (1.31×10$^4$), and 697 nm (3.91×10$^3$ L·mol$^{-1}$·cm$^{-1}$); $^1$H NMR (500 MHz, $CDCl_3$, ppm) δ 9.59 (s, 1H), 9.46 (s, 1H), 8.62 (s, 1H), 8.04 (1H), 6.36 (1H), 6.31 (s, 1H), 6.24 (1H), 5.19 (2H), 4.54 (2H), 4.26 (1H), 3.91 (s, 3H), 3.75 (5H), 3.46 (3H), 3.29 (3H), 2.70 (1H), 2.51 (1H), 2.37 (1H), 2.26 (1H), 1.91 (2H), 1.85 (3H), 1.70 (3H), 1.59 (3H), and 0.81-1.32 (m, 21H).

Example 3: Synthesis of 15b-methyl-13a,17c-di[N,N',N,N,N,N-hexapropyl-panta(aminoethylene)]amide-chlorin $e_6$ (Chl-$N_{10}$, LC38)

Di(N,N',N,N,N,N-hexapropyl-panta(aminoethylene) amide)-derived chlorin intermediate (Chl-$N_{10}$) was obtained by a one-pot reaction including a transamination on the phytyl acetate moiety and a ring-open reaction on the exocyclic ring moiety of pheophytin-a with N,N',N,N,N,N-hexapropyl-penta(aminoethylene)amine. The intermediate Phe-$N_5$ was obtained by transamination of pheophytin-a with N,N',N,N,N,N-hexapropyl-penta(aminoethylene) amine.

General procedure: To the solution of pheophytin-a (0.30 g, 0.35 mM) and N,N',N,N,N,N-hexapropyl-penta(aminoethylene)amine (0.36 g, 0.72 mmol) in dichloromethane (20 mL), was added trifluoroacetic acid (0.23 mL, 3.0 mmol)

slowly under $N_2$. The mixture was stirred at r.t. for 10 h followed by solvent evaporation to give raw products, which were purified by column chromatography (neutral alumina) using the eluent of dichloromethane-acetone (1:1) to afford green solids of the precursor intermediate Chl-$N_{10}$ in a yield of 80% (0.43 g). Spectroscopic data: FT-IR (KBr) $\nu_{max}$ 2989 (w), 2976 (m), 2938 (w), 2880 (w), 1738 (s), 1733 (s), 1663 (s), 1656 (m), 1630 (s), 1624 (m), 1590 (w), 1542 (m), 1510 (m), 1458 (s), 1435 (m), 1389 (m), 1381 (m), 1350 (m), 1235 (m), 1179 (m), 1211 (w), 1041 (m), 985 (m), 960 (m), 893 (w), 845 (w), 815 (w), 784 (w), 766 (w), 740 (m), 674 (m), and 605 (m) $cm^{-1}$; UV-vis (DMF, $1.0\times10^{-5}$ M) $\lambda_{max}$ (ε) 414 nm ($4.01\times10^4$), 510 nm ($5.26\times10^3$), 538 nm ($4.42\times10^3$), 566 ($2.71\times10^3$), 610 nm ($3.39\times10^3$), and 670 nm ($1.50\times10^4$ $L\cdot mol^{-1}\cdot cm^{-1}$).

Example 4: Synthesis of 15b-methyl-13a,17c-di[N,N',N,N,N,N-hexapropyl-panta(aminoethylene)]amide-[$Pd^{+2}$]chlorin $e_6$ ($Chl_{pd}$-$N_{10}^+$, LC38$^+$)

The intermediate Chl-$N_{10}$ (LC38, 0.20 g, 0.13 mmol) was dissolved in DMF and treated with $Pd(OAc)_2$ (0.032 g, 0.14 mmol) for 8.0 h, followed by reacting with $CH_3I$ (excess) at 45° C. for 24 h. During the solvent removal process by rotary-evaporation, an excessive amount of $CH_3I$, was also eliminated. The crude products were washed by chloroform and ether to afford $Chl_{pd}$-$N_{10}^+$ (LC38$^+$) as green solids. Spectroscopic data: FT-IR (KBr) $\nu_{max}$ 2997 (w), 2966 (m), 2928 (w), 2874 (w), 2846 (w), 1732 (s), 1663 (s), 1630 (m), 1624 (m), 1586 (w), 1549 (m), 1501 (m), 1469 (s), 1431 (m), 1386 (m), 1376 (m), 1355 (m), 1231 (m), 1179 (m), 1211 (w), 1062 (w), 1039 (m), 989 (m), 969 (m), 892 (w), 845 (w), 815 (w), 785 (w), 760 (w), 740 (m), 671 (m), and 602 (m) $cm^{-1}$; UV-vis (DMF, $1.0\times10^{-5}$ M) $\lambda_{max}$ (ε) 412 nm ($4.22\times10^4$), 506 nm ($5.20\times10^3$), 534 nm ($4.53\times10^3$), 560 ($2.71\times10^3$), 607 nm ($3.44\times10^3$), and 666 nm ($1.42\times10^4$ $L\cdot mol^{-1}\cdot cm^{-1}$); $^1H$ NMR (500 MHz, DMSO-$d_6$, ppm) δ 9.55 (s, 1H), 9.30 (s, 1H), 8.33 (s, 1H), 7.99 (1H), 6.21 (1H), 6.02 (1H), 3.12-4.48 (m, br, 110H), 2.54 (2H), 2.47 (2H), 2.35 (2H), 1.60-1.91 (m, br, 30H), and 0.96 (m, 36H).

Example 5: Synthesis of 3a-hydroxy-3b-aminoethylene-aminoPEGlycolated vancomycin-15b-methyl-13a,17c-di[N,N',N,N,N,N-hexapropyl-panta(aminoethylene)]amide-mesochlorin (VCMe-m$Chl_{pd}$-$N_{10}^+$, LC40e)

Step A: To the solution Chl-$N_{10}$ (LC38, 0.32 g, 0.21 mmol) in THF-$H_2O$ (3.0:1.0, v/v) was added m-chloroperoxybenzoic acid (mCPBA, 0.039 g, 0.22 mmol) to epoxidate the olefin bond ($C_{3a}$=$C_{3b}$) of the pheophytin-a core moiety. It was followed by the addition of ethylenediamine (0.015 g, 0.25 mmol) to effect the oxirane ring-opening of the resulting epoxide in the presence of a di(n-butyl)tin(IV) dilaurate (T12, 150 μL) catalyst and triethylamine (150 μL, 1.1 mmol) at 60° C. for 3.0 h. The reaction progress was monitored by thin-layer chromatography (neutral alumina) using the eluent of dichloromethane-acetone (1:1). A small amount of excessive ethylenediamine and triethylamine were removed along with the solvent removal using rotary evaporator to afford a precursor intermediate of 3a-hydroxy-3b-aminoethylene-amino-Chl-$N_{10}$.

Step B: To the solution of poly(ethylene glycol) diglycidyl ether (Mn~500, 0.10 g, 0.2 mmol) in THF-$H_2O$ (3.0:0.7, v/v) was added di(n-butyl)tin(IV) dilaurate (T12, 100 μL) catalyst and triethylamine (150 μL, 1.1 mmol). The mixture was stirred at 60° C. for 20 min. Vancomycin hydrochloride (1.0 equiv., 0.30 g, 0.21 mmol) in $H_2O$ solution was then added slowly in a period of 2.0 h to ensure the monoaddition reaction. The mixture was stirred for another 1.0 h, followed by the addition of 3a-hydroxy-3b-aminoethylene-amino-Chl-$N_{10}$ (from the step A) solution in THF-$H_2O$ (3.0:0.7, v/v) to effect the reaction with the remaining glycidyl group at 60° C. for 3.0 h. Raw products obtained were dissolved in dil. HCl to remove the insoluble 4-chlorobenzoic acid generated during the reaction. The resulting precursor intermediate VCMe-mChl-$N_{10}$ was obtained as green solids after neutralization by a saturated $K_2CO_3$ in DMF solution. The solids were further extracted by methanol to remove an excessive vancomycin and $K_2CO_3$. The subsequent treatment of resulting products with $Pd(OAc)_2$ (0.050 g, 0.22 mmol), followed by $CH_3I$ at 45° C. in DMF affords VCMe-m$Chl_{Pd}$-$N_{10}^+$ (LC40e). Spectroscopic data: FT-IR (KBr) $\nu_{max}$ 2984 (m), 2980 (w), 2964 (w), 2946 (w), 2874 (w), 2858 (w), 1746 (s), 1679 (s), 1657 (s), 1618 (m), 1599 (m), 1560 (m), 1508 (m), 1465 (m), 1454 (m), 1426 (m), 1400 (m), 1379 (m), 1370 (m), 1360 (m), 1345 (m), 1314 (w), 1297 (m), 1249 (m), 1235 (m), 1179 (w), 1116 (s), 1110 (s), 1061 (m), 1029 (m), 991 (m), 960 (m), 952 (m), 892 (w), 886 (m), 848 (w), 826 (w), 769 (w), 740 (m), 712 (m), and 610 (m) $cm^{-1}$; UV-vis (DMF, $1.0\times10^{-5}$ M) $\lambda_{max}$ (ε) 284 nm ($2.64\times10^4$), 410 nm ($2.22\times10^4$), 512 nm ($3.54\times10^3$), 556 nm ($2.64\times10^3$), 580 nm ($2.33\times10^3$), and 677 nm ($2.38\times10^3$ $L\cdot mol^{-1}\cdot cm^{-1}$).

Example 6: Synthesis of 3a-hydroxy-3b-vancomycin-15b-methyl-17c-[N,N',N,N,N,N-hexapropyl-penta(aminoethylene)]amide-[$Zn^{+2}$]mesopheophorbide (VCM-m$Phe_{Zn}$-$N_5^+$, LC39)

The starting pheophytin-a (Phe) was first reacted with N,N',N,N,N,N-hexapropyl-penta(aminoethylene)amine via the transamination reaction to give an intermediate Phe-$N_5$. In the synthetic procedure, the solution of pheophytin-a (0.60 g, 0.69 mM) and N,N',N,N,N,N-hexapropyl-penta(aminoethylene)amine (0.36 g, 0.72 mmol) in dichloromethane (20 mL) was added trifluoroacetic acid (0.45 mL, 5.9 mmol) slowly under $N_2$. The mixture was stirred at r.t. for 10 h, followed by the solvent evaporation to give the crude product. It was neutralized by saturated $K_2CO_3$ in DMF and purified by column chromatography (neutral alumina) using the eluent of dichloromethane-acetone (1:2) to afford green solids of the precursor intermediate Phe-$N_5$ in a yield of 85% (0.63 g).

To the solution Phe-$N_5$ (0.22 g, 0.21 mmol) in THF-$H_2O$ (3.0:0.7, v/v) was added m-chloroperoxybenzoic acid (MCPBA, 0.040 g, 0.23 mmol) to epoxidate the olefin bond ($C_{3a}$=$C_{3b}$) of the pheophytin-a core structure. It was followed by the addition of vancomycin hydrochloride (0.32 g, 0.22 mmol) to effect the oxirane ring-opening of the resulting epoxide in the presence of a di(n-butyl)tin(IV) dilaurate (T12, 150 μL) catalyst and triethylamine (150 μL, 1.1 mmol) at 60° C. for 3.0 h. The raw products were dissolved in dil. HCl to remove the insoluble 4-chlorobenzoic acid generated during the reaction. The precursor intermediate VCM-mPhe-$N_5$ was obtained as green solids after neutralization by a saturated $K_2CO_3$ in DMF solution and extraction by methanol to remove an excessive vancomycin and $K_2CO_3$. It was subsequently treated by $Zn(OAc)_2$ (dihydrate, 0.050 g, 0.22 mmol) and $CH_3I$ at 45° C. in DMF to afford VCM-m$Phe_{Zn}$-$N_5^+$. Spectroscopic data: FT-IR (KBr) $\nu_{max}$ 2974 (m), 2960 (w), 2944 (w), 2926 (w), 2884 (w), 2848 (w), 1736 (m), 1677 (s), 1655 (s), 1614 (m), 1589 (m), 1555 (m), 1502 (m), 1465 (m), 1422 (m), 1400 (w), 1398 (m), 1376 (m), 1370 (m), 1340 (m), 1314 (w), 1232 (m), 1179 (w), 1152 (w), 1127 (w), 1061 (m), 1025 (m), 991 (m), 966 (m), 892 (w), 848 (w), 819 (w), 780 (w), 763 (w), 738 (m), 711 (m), and 612 (m) cm-1; UV-vis (DMF, $1.0\times10^{-5}$ M). $\lambda_{max}$ (8) 282 nm ($2.52\times10^{4}$), 406 nm ($2.11\times10^{4}$), 512 nm ($3.04\times10^{3}$), 554 nm ($2.44\times10^{3}$), 580 nm ($2.06\times10^{3}$), and 672 nm ($2.41\times10^{3}$ $L\cdot mol^{-1}\cdot cm^{-1}$).

Example 7: Synthesis of 15b-methyl-13a,17c-di[N, N',N,N,N,N-hexapropyl-panta(aminoethylene)-malonyloxypropylene]amide-chlorin (Chl-$mN_{10}$, LC38m)

The solution of pheophytin-a (0.50 g, 0.58 mM) and 3-aminopropanol (0.13 g, 1.26 mmol) in dichloromethane (20 mL) was added by trifluoroacetic acid (0.45 mL, 5.9 mmol) slowly under $N_2$. The mixture was stirred at r.t. for 10 h, followed by the solvent evaporation to give a raw product. It was further purified by column chromatography (neutral alumina) using the eluent of dichloromethane-acetone (1:2) to afford green solids of the precursor intermediate Chl-di (2-aminopropanol) in a yield of 82% (0.36 g). Separately, a second precursor intermediate, malonic acid mono-N,N',N, N,N,N-hexapropyl-penta(aminoethyl)amide ($N_6C_3$-$MCO_2H$), was pre-prepared by the ring-opening reaction of meldrum's acid (2,2-dimethyl-1,3-dioxane-4,6-dione) (0.10 g, 0.70 mmol) using N,N',N,N,N,N-hexapropyl-penta(aminoethylene)amine (0.35 g, 0.70 mmol) under $N_2$.

A Steglich esterification was applied to form the malonate-containing di[hexapropylpenta(aminoethylene)]-modified chlorin (Chl-$mN_{10}$). General procedure: The solution of $N_6C_3$-$MCO_2H$ (0.11 g, 0.20 mmol) in anhydrous THF was added by N,N'-dicyclohexylcarbodiimide (DCC, 0.05 g, 0.24 mmol) and 4-dimethylaminopyridine (DMAP, 2.0 mg) as the catalyst. The mixture was stirred at r.i. for 30 min. It was then added by Chl-di(2-aminopropanol) (0.077 g, 0.10 mmol) and the reaction mixture was kept stirring at r.t. for another 8.0 hr. After filtering off white precipitates of dicyclohexylurea (DCU), the solution was washed with ethyl acetate and dried to afford the chlorin derivative product Chl-$mN_{10}$(LC38m) as green solids in a yield of 82% (0.14 g). Spectroscopic data: FT-IR (KBr) $\nu_{max}$ 2985 (w), 2980 (m), 2931 (w), 2870 (w), 1747 (s), 1745 (s), 1741 (s), 1660 (s), 1655 (s), 1635 (m), 1621 (m), 1588 (w), 1549 (m), 1513 (m), 1462 (s), 1439 (s), 1413 (m), 1389 (m), 1350 (m), 1277 (m), 1235 (m), 1209 (m), 1169 (m), 1208 (w), 1021 (s), 988 (m), 962 (m), 849 (w), 818 (w), 788 (w), 760 (w), 744 (m), 678 (m), and 606 (m) $cm^{-1}$; UV-vis (DMF, $1.0\times10^{-5}$ M) $\lambda_{max}$ (ε) 414 nm ($4.21\times10^{4}$), 512 nm ($5.31\times10^{3}$), 542 nm ($4.50\times10^{3}$), 570 ($2.78\times10^{3}$), 612 nm ($3.42\times10^{3}$), and 668 nm ($1.58\times10^{4}$ $L\cdot mol^{-1}\cdot cm^{-1}$).

Example 8: Synthesis of One Nano-$C_{60/70}$PS Analogous Example as $Chl_{pd}$-($C_{70}$>)$N_{10}^{+}$ (LC41)

A dilute solution of Chl-$mN_{10}^{+}$ (LC38m, 0.32 g, 0.10 mmol) in DMF-toluene (7:3, v/v) was added by $CBr_4$ (0.08 g, 0.24 mmol) and 1,8-diazabieyclo[5.4.0]undec-7-ene (DBU, 0.08 g, 0.52 mmol) and stirred under $N_2$ at r.t. for 1.0 h. It was then added slowly by the solution of $C_{70}$ (0.084 g, 0.10 mmol) in DMF-toluene (3:7, v/v) in 1.0 hr under $N_2$ at r.t. to form the Bingel hisadduct of $C_{70}$ as Chl-$mN_{10}^{+}$. The reaction mixture was further stirred under $N_2$ at r.t. for another 2.011, followed by the addition of $Pd(OAc)_2$ (0.022 g, 0.10 mmol) to insert $Pd^{+2}$ ion onto the chlorin ring moiety. After precipitation by the addition of ethyl acetate, it was washed by ethyl acetate, toluene, and diethyl ether in sequence, and dried to afford the final product of $Chl_{pd}$-($C_{70}$>)$N_{10}^{+}$ (LC41) as greenish brown solid. Spectroscopic data: 3000 (w), 2986 (m), 2958 (w), 2903 (w), 2886 (w), 1740 (s), 1732 (s), 1697(s), 1668 (s), 1630 (m), 1618 (m), 1586 (w), 1555 (m), 1523(m), 1501 (m), 1469 (s), 1433 (m), 1380 (m), 1376 (m), 1352 (m), 1268 (m), 1231 (m), 1211 (w), 1179 (m), 1062 (w), 1045 (m), 1001 (m), 974 (m), 895 (w), 848 (w), 815 (w), 760 (w), 740 (m), 671 (m), 602 (m), 578 (w) and 536 (w) $cm^{-1}$; UV-vis (DMF, $1.0\times10^{-5}$ M) $\lambda_{max}$ (ε) 330 ($3.25\times10^{3}$), 378 ($2.8\times10^{3}$), 412 nm ($4.22\times10^{4}$), 468 ($1.62\times10^{3}$), 506 nm ($5.20\times10^{3}$), 534 nm ($4.53\times10^{3}$), 560 ($2.71\times10^{3}$), 607 nm ($3.44\times10^{3}$), and 666 nm ($1.42\times10^{4}$ $L\cdot mol^{-1}\cdot cm^{-1}$); $^{1}H$ NMR (500 MHz, DMSO-$d_6$, ppm) δ 9.58 (s, 1H), 9.40 (s, 1H), 8.43 (s, 1H), 8.04 (1H), 6.25 (1H), 6.09 (1H), 2.78-4.58 (m, br, 118H), 2.55 (2H), 2.49 (2H), 2.42 (2H), 1.61-1.93 (m, br, 34H), and 0.96 (m, 36H).

Example 9: Synthesis of One $C_{60}$/PS-CB-Abx Analogous Example as VCMe-m$Chl_{Pd}$-($C_{70}$>)$N_{10}^{+}$ (LC42)

To the solution of $Chl_{pd}$-($C_{70}$>)$N_{10}^{+}$ (LC41, 0.32 g, 0.21 mmol) in THF-$H_2O$ (1.0:1.0, v/v) was added m-chloroperoxybenzoic acid (MCPBA, 0.04 g, 0.23 mmol) to epoxidate the olefin bond ($C_{3a}$=$C_{3b}$) of the chlorin core moiety. The reaction was followed by the addition of ethylenediamine (0.015 g, 0.25 mmol) to react with the oxirane ring of resulting epoxide moiety using a catalyst of di(n-butyl)tin (IV) dilaurate (T12, 150 μL) and triethylamine (150 μL, 1.1 mmol) at 60° C. for 3.0 h. The small amount of excessive ethylenediamine and triethylamine were removed together by the solvent evaporation technique using rotary evaporator to afford the precursor intermediate 3a-hydroxy-3b-aminoethylene-amino-$Chl_{Pd}$-($C_{70}$>)$N_{10}^{+}$.

In a separate reaction, a solution of poly(ethylene glycol) diglycidyl ether (Mn~500, 0.10 g, 0.2 mmol) in THF-$H_2O$ (3.0:0.7, v/v) was added di(n-butyl)tin(IV) dilaurate (T12, 100 μL) catalyst and triethylamine (150 μL, 1.1 mmol). The mixture was stirred at 60° C. for 20 min. Vancomycin hydrochloride (1.0 equiv., 0.30 g, 0.21 mmol) in $H_2O$ solution was then added slowly in a period of 2.0 h to ensure the monoaddition reaction. The mixture was stirred for another 1.0 h, followed by the addition of 3a-hydroxy-3b-aminoethylene-amino-$Chl_{Pd}$-($C_{70}$>)$N_{10}^{+}$ (from the step above) solution in $H_2O$ to effect the reaction with the remaining glycidyl group at 60° C. for 3.0 h. Raw products obtained were dissolved in dil. HCl to remove the insoluble 4-chlorobenzoic acid generated during the reaction. The resulting precursor product VCMe-mChl-($C_{70}$>)$N_{10}^{+}$ was obtained as green solids. The solids were further extracted by methanol to remove an excessive vancomycin and $K_2CO_3$. The subsequent treatment of VCMe-mChl-($C_{70}$>) $N_{10}^{+}$ with $Pd(OAc)_2$ (0.050 g, 0.22 mmol) in DMF affords VCMe-m$Chl_{Pd}$-($C_{70}$>)$N_{10}^{+}$ (LC42). Spectroscopic data: 2990 (m), 2985 (w), 2974 (w), 2878 (w), 2865 (m), 1740 (s), 1669 (s), 1660 (s), 1634 (m), 1600 (m), 1572 (m), 1528 (m), 1470 (m), 1460 (m), 1429 (m), 1404 (m), 1382 (m), 1366 (m), 1344 (m), 1314 (w), 1302 (m), 1252 (m), 1245 (m), 1122 (s), 1116 (s), 1065 (m), 1023 (m), 993 (m), 958 (m), 892 (w), 889 (m), 846 (w), 826 (w), 775 (w), 742 (m), 715 (m), 615 (m), 578 (w), and 535 (w) $cm^{-1}$; UV-vis (DMF, $1.0\times10^{-5}$ M) $\lambda_{max}$ (ε) 284, 330, 378, 410, 468, 512, 556, 580, and 677 nm.

Example 10: Reactive Oxygen Species (ROS) Measurements of Superoxide Radicals ($O_2^{-}\cdot$)

In the reactive oxygen species (ROS) measurements, fluorometric traces were collected using a PTI QuantaMaster™ 40 Fluorescence Spectrofluorometer. The light sources used was an ultrahigh power white-light LED lamp (Prizmatix, operated at the emission peak maxima centered at 451 and 530 nm with the collimated optical power output of >2000 mW in a diameter of 5.2 cm) for the generation of emission spectra at visible light range.

A superoxide radical reactive fluorescent probe bis(2,4-dinitrobenzenesulfonyl) tetrafluorofluorescein carboxylate (DNBs-TFFC) was used to detect $O_2^{-}\cdot$ generated in solution. A typical probe solution was prepared by diluting a stock probe solution of DNBs-TFFC in DMSO (5.0 mM) by 300 times with D.I. water. A dialysis film with a molecular weight cut-off (MWCO) of 100-500 Daltons was used to separate the solution of photosensitizers in $H_2O$-DMSO (19:1, 5.0 μM) from the probe solution kept in a cuvette with stirring during the fluorescent measurement. To minimize photodegradation side-reaction of DNBs-TFFC and TFFC, only the photosensitizer solution in the membrane sack was allowed to white LED light exposure (excitation wavelength of 420-650 nm with) $\lambda_{em,max}$ at 451 and 530 nm). The quantity of $O_2^{-}$ generated was correlated and counted proportionately by the measured fluorescence emission intensity of TFFC at 520-530 nm upon excitation at 480 nm. TFFC is a reaction product of DNBs-TFFC probe with $O_2^{-}\cdot$ in solution.

Example 11: Reactive Oxygen Species (ROS) Measurements of Singlet Oxygen ($^1O_2$)

The data of fluorometric traces were collected using a PTI QuantaMaster™ 40 Fluorescence Spectrofluorometer. The light sources used was an ultrahigh power white-light LED lamp (Prizmatix, operated at the emission peak maxima centered at 451 and 530 nm with the collimated optical power output of >2000 mW in a diameter of 5.2 cm) for the generation of emission spectra at visible light range.

A singlet oxygen ($^1O_2$) reactive fluorescent probe α,α'-(anthracene-9,10-diyl)bis(methylmalonic acid) (ABMA) was used to detect $^1O_2$ generated in solution. A typical probe solution was prepared by diluting a stock probe solution of ABMA in DMSO (5.0 mM) by 300 times with D.I. water. A dialysis film with a molecular weight cut-off (MWCO) of 100-500 Daltons was used to separate the solution of photosensitizers in $H_2O$-DMSO (19:1, 5.0 μM) from the probe solution kept in a cuvette with stirring during the fluorescent measurement. To minimize photodegradation side-reaction of ABMA, only the photosensitizer solution in the membrane sack was allowed to white LED light exposure (excitation wavelength of 420-650 nm with $\lambda_{em,max}$ at 451 and 530 nm). $O_2^{-}\cdot$ generated was monitored by the loss of ABMA emission maximum at 429 nm under excitation at 350 nm. The quantity of $^1O_2$ generated was correlated and counted by the relative fluorescence intensity decrease of ABMA at 429 nm.

Example 12: Antimicrobial Photodynamic Inactivation (aPDI) of Multidrug-Resistant (MDR) Bacteria Mediated by Fullerenyl Mesochlorin Derived Nano-Photosensitizers, Nano-$C_{60/70}$PS Bacterial strains: Two Gram-positive MRSA strains (IQ0064 and IB0004) and one Gram-negative *Acinetobacter baumannii* strain (AF0004) were studied. All of them are clinical isolates. MRSA IQ0064 was a multidrug-resistant strain isolated from wounded military personnel deployed to Iraq. According to a microbiology test, IQ0064 strain was resistant to ampicillin, cefazolin, cefoxitin, oxacillin, and penicillin. MRSA IB0004 was an isolate from a keratitis patient. *A. baumannii* AF0004 was a multidrug-resistant strain isolated from wounded military personnel deployed to Afghanistan. AF0004 was resistant to a panel of important antibiotics including amikacin, ampicillin, aztreonam, cefazolin, cefepime, cefoxitin, ceftazidime, ceftriaxone, cefuroxime, ciprofloxacin, gentamicin, imipenem, levofloxacin, meropenem, nitrofurantoin, tetracycline and trimethoprim-sulfamethoxazole.

Nano-photosensitizers: Four fullerenyl mesochlorin nano-$C_{60/70}$PSs: (a) $Chl_{Pd}$-$EG_n$ (LC37), (b) $Chl_{Pd}$-$N_{10}^+$ ($LC38^+$), (c) VCMe-m$Chl_{Pd}$-$N_{10}^+$ (LC40e), and (d) $Chl_{Pd}$-($C_{70}$>)$N_{10}^+$ (LC41) were evaluated and studied.

Light source: Light was delivered topically using a non-coherent light source (LumaCare, Newport Beach, CA) that provided the full spectrum of visible light (400 to 800 nm). The system employed interchangeable filter probes and produced a uniform spot for illumination. We used a 660±15-nm filter probe. The irradiance of 40 mW/$cm^2$ was used throughout the study. The light power was routinely measured using a laser power meter (Fieldmate; Coherent, Portland, OR).

Antimicrobial photodynamic inactivation (aPDI) of bacteria: Bacterial suspensions were adjusted to $10^8$ CFU/mL, inoculated to 96-well plates (200 μL/well), incubated with fullerenes at 6.25, 12.50, 18.75, and 25.00 μM concentrations for 1.0 h and then either left in dark or irradiated with 660 nm light at 115 J/$cm^2$. At the completion of each stage of illumination, the contents of the wells were well mixed before sampling. Aliquots (30 μL) were taken from each well to determine CFU. The aliquots were serially diluted 10-fold in phosphate-buffered saline (PBS) to give dilutions of $10^1$ to $10^5$ times in addition to the original concentration; then, 10 μL aliquots of each of the dilutions were streaked horizontally on square BHI plates. Plates were streaked in triplicate and incubated for 24 h at 37° C. in the dark to allow colony formation. Control groups included bacterial cells that were treated with light alone (no fullerene monoadducts added), and cells treated with fullerene monoadducts (no light) as the dark control. Survival fractions were routinely expressed as ratios of CFU of bacterial cells treated with light and fullerene monoadducts, or treated with fullerenes in the absence of light, to CFU of bacteria treated with neither.

Example 13: Method of Topical Treatments

The compositions described herein may be used for the treatment of skin infections. The present method comprises applying a composition of the present invention to a suitable target and activating the nano-$C_{60/70}$PS or $C_{60/70}$PS-CB-Abx compound. Typically, from about 0.1 to 5 mg/kg, preferably from about 2.5 to 3.5 mg/kg, of the composition is applied to the target. The activation energy can be from a suitable energy source, such as portable LED lights having a wavelength range of either UVA, blue, white, or red band.

The compositions may be used for the treatment of sinusitis. The present method comprises applying a composition to a suitable target and activating the nano-$C_{60/70}$PS or $C_{60/70}$PS-CB-Abx compound. Typically, from about 0.1 to 5 mg/kg, preferably from about 2.5 to 3.5 mg/kg, of the composition is applied to the target. The activation energy can be from a suitable energy source.

The compositions may be used for the treatment of wound infections. The present method comprises applying a composition to a suitable target and activating the nano-$C_{60/70}$PS or $C_{60/70}$PS-CB-Abx compound. Typically, from about 0.1 to 5 mg/kg, preferably from about 2.5 to 3.5 mg/kg, of the composition is applied to the target. The activation energy can be from a suitable energy source.

The compositions may be used for the treatment of burn infections. The present method comprises applying a composition to a suitable target and activating the nano-$C_{60/70}$PS or $C_{60/70}$PS-CB-Abx compound. Typically, from about 0.1 to 5 mg/kg, preferably from about 2.5 to 3.5 mg/kg, of the composition is applied to the target. The activation energy can be from a suitable energy source.

The compositions can be used for the treatment of soft tissue infections. The present method comprises applying a composition to a suitable target and activating the nano-$C_{60/70}$PS or $C_{60/70}$PS-CB-Abx compound. Typically, from about 0.1 to 5 mg/kg, preferably from about 2.5 to 3.5 mg/kg, of the composition is applied to the target. The activation energy can be from a suitable energy source.

The compositions can be used for the treatment of periodontitis. The present method comprises applying a composition to a suitable target and activating the nano-$C_{60/70}$PS or $C_{60/70}$PS-CB-Abx compound. Typically, from about 0.1 to 50 mg/kg, preferably from about 2.5 to 3.5 mg/kg, of the composition is applied to the target. The activation energy can be from a suitable energy source.

The compositions of used for the treatment of acne. The present method comprises applying a composition to a suitable target and activating the nano-$C_{60/70}$PS or $C_{60/70}$PS-CB-Abx compound. Typically, from about 0.1 to 50 mg/kg, preferably from about 2.5 to 3.5 mg/kg, of the composition is applied to the target. The activation energy can be from a suitable energy source.

The compositions o can be used for the treatment of keratitis. The present method comprises applying a composition to a suitable target and activating the nano-$C_{60/70}$PS or $C_{60/70}$PS-CB-Abx compound. Typically, from about 0.1 to 50 mg/kg, preferably from about 2.5 to 3.5 mg/kg, of the composition is applied to the target. The activation energy can be from a suitable energy source.

The compositions can be used for the treatment of otitis media. The present method comprises applying a composition to a suitable target and activating the nano-$C_{60/70}$PS or $C_{60/70}$PS-CB-Abx compound. Typically, from about 0.1 to 50 mg/kg, preferably from about 2.5 to 3.5 mg/kg, of the composition is applied to the target. The activation energy can be from a suitable energy source.

The compositions can be used for the treatment of urinary tract infections. The present method comprises applying a composition to a suitable target and activating the nano-$C_{60/70}$PS or $C_{60/70}$PS-CB-Abx compound. Typically, from about 0.1 to 50 mg/kg, preferably from about 2.5 to 3.5 mg/kg, of the composition is applied to the target. The activation energy can be from a suitable energy source.

The compositions may be used for the treatment of gastric *H. pylori* infections. The present method comprises applying a composition to a suitable target and activating the nano-$C_{60/70}$PS or $C_{60/70}$PS-CB-Abx compound. Typically, from about 0.1 to 50 mg/kg, preferably from about 2.5 to 3.5 mg/kg, of the composition is applied to the target. The activation energy can be from a suitable energy source.

The compositions can be used for the treatment of genital tract infections. The present method comprises applying a composition to a suitable target and activating the nano-$C_{60/70}$PS or $C_{60/70}$PS-CB-Abx compound. Typically, from about 0.1 to 50 mg/kg, preferably from about 2.5 to 3.5 mg/kg, of the composition is applied to the target. The activation energy can be from a suitable energy source.

The compositions of can be used for the treatment of intra-abdominal abscess. The present method comprises applying a composition to a suitable target and activating the nano-$C_{60/70}$PS or $C_{60/70}$PS-CB-Abx compound. Typically, from about 0.1 to 50 mg/kg, preferably from about 2.5 to 3.5 mg/kg, of the composition is applied to the target. The activation energy can be from a suitable energy source.

The compositions can be used for the treatment of onychomycosis. The present method comprises applying a composition to a suitable target and activating the nano-$C_{60/70}$PS or $C_{60/70}$PS-CB-Abx compound. Typically, from about 0.1 to 50 mg/kg, preferably from about 2.5 to 3.5 mg/kg, of the composition is applied to the target. The activation energy can be from a suitable energy source.

The compositions can be used for the treatment of leishmaniasis. The present method comprises applying a composition to a suitable target and activating the nano-$C_{60/70}$PS or $C_{60/70}$PS-CB-Abx compound. Typically, from about 0.1 to 50 mg/kg, preferably from about 2.5 to 3.5 mg/kg of the composition is applied to the target. The activation energy can be from a suitable energy source.

The compositions can be used for the treatment of localized tuberculosis. The present method comprises applying a composition to a suitable target and activating the nano-$C_{60/70}$PS or $C_{60/70}$PS-CB-Abx compound. Typically, from about 0.1 to 50 mg/kg, preferably from about 2.5 to 3.5 mg/kg, of the composition is applied to the target. The activation energy can be from a suitable energy source.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A fullerene/photosensitizer covalently-bonded antibiotic compound of the following formula (I):

(I)

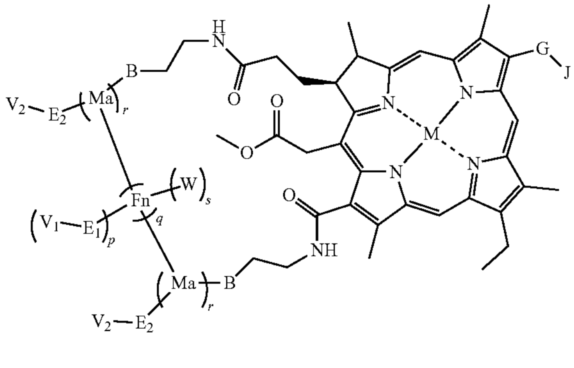

wherein

Fn is a fullerene core, wherein Fn is $C_{70}$;

M is a metal ion selected from Mn, Ru, Rh, Pd, Pt, or Si;

B is amino-$C_{1-200}$ alkyl ether, amino-$C_{1-200}$ alkyl, hydroxy-$C_{1-200}$ alkyl ether, hydroxy-$C_{1-200}$ alkyl, wherein the amino or hydroxyl is linked to a Ma carbonyl group as an amide or ester;

Ma is —NH—CO-cyclopropanyl-CO— or —O—CO-cyclopropanyl-CO—;

G is —CH(O—$V_2$)—$CH_2$— or —CH(O—CO—Z—$V_2$)—$CH_2$—;

J is -$E_3$-Abx; wherein Abx is an amino or amide group-containing antibiotic molecule;

$E_1$, $E_2$, and $E_3$ are each independently $Y_1$,$Y_2$-amino, ($Y_1$,$Y_2$-alkyl)-amino, $Y_1Y_2$-ethylenediamino, (dihydroxymethyl) alkylamino, ($X_1$,$X_3$-aryl)amino, $X_1$,$X_3$-aryloxy, $Y_2$-alkoxy, $Y_1$,$Y_2$-alkoxy, ($Y_1$,$Y_2$-amino) alkoxy, ($Y_1$,$Y_2$,$Y_3$-aryl)oxy, (dihydroxyalkyl)-aryloxy, ($Y_1$,$Y_2$,$Y_3$-alkyl)amino, ($Y_1$,$Y_2$,$Y_3$-aryl)amino, dihydroxyalkylamino, $Y_1$,$Y_2$,$Y_3$-alkoxy, (trihydroxyalkyl) alkoxy, (trihydroxyalkyl)alkylamino, (dicarboxyalkyl) amino, $Y_2$-thio, ($Y_1$,$Y_2$,$Y_3$-alkyl)thio, ($X_1$,$X_3$-aryl) thio, ($Y_1$,$Y_2$-alkyl)thio, (dihydroxyalkyl)thio, $Y_1$,$Y_2$-dioxoalkyl, tri-($Y_1$,$Y_2$,$Y_3$-methylaminocarboxyethyl) methylamino, ((glycosidyl)oxoheteroaryl)amino, ((glycosidyl)oxoaryl)amino, ($X_1$,$X_2$,$X_3$-heteroaryl) amino, ($X_1$-diarylketone)amino, (T,$X_1$-oxoaryl)amino, (T,$X_1$-dioxoaryl)amino, ($Y_1$-alkyl,$Y_2$-alkyldioxoheteroaryl) amino, ($Y_1$-alkyl,$Y_2$-alkyldioxoaryl)amino, (di($Y_1$,$Y_2$-methyl)dioxoheteroaryl)amino, (di($Y_1$,$Y_2$-methyl)dioxoaryl)amino, ((glycosidyl)heteroaryl) amino, ((glycosidyl)aryl)amino, ((carboxylacetylalkyl) oxo-heteroaryl)amino, ((carboxylacetylalkyl)oxoaryl) amino, ((isopropylaminohydroxy-alkoxy)aryl)amino, ($X_1$,$X_2$,$X_3$-alkylaryl)amino, ($X_1$,$X_2$,$X_3$-heteroaryl)oxy, (isopropylaminohydroxyalkyl)aryloxy, ($X_1$,$X_2$,$X_3$-oxoheteroaryl)oxy, ($X_1$,$X_2$,$X_3$-oxoaryl)oxy, ($X_1$,$Y_1$-oxoheteroaryl)oxy, ($X_1$-diarylketone)oxy, (T,$X_1$-oxoaryl)oxy, ($X_1$,$X_2$-dioxoaryl)oxy, ($Y_1$,$Y_2$,di-aminodihydroxy)alkyl, ($X_1$,$X_2$-heteroaryl)thio, ((tricarboxylalkyl)ethylene-diamino)alkoxy, ($X_1$,$X_2$-oxoaryl)thio, ($X_1$,$X_2$-dioxoaryl)thio, (glycosidylheteroaryl)thio, (glycosidylaryl)thio, $Y_1$-alkyl(thiocarbonyl)thio, $Y_1$,$Y_2$,-alkyl(thiocarbonyl)thio, $Y_1$,$Y_2$,$Y_3$-alkyl(thiocarbonyl)thio, ($Y_1$,$Y_2$-aminothiocarbonyl) thio, (pyranosyl)thio, cysteinyl, tyrosinyl, (phenylalaninyl)amino, (dicarboxyalkyl)thio, (amino-aryl)$_{1-100}$amino, (pyranosyl)$_{1-100}$amino, ($Y_1$-amino-aryl)$_{1-100}$amino, (amino(sulfoaryl))$_{1-100}$amino, peptidyl, thymidinyl, uridinyl, guanosinyl, adenosinyl, cholesteryl, or biotinylalkoxy; wherein T is halo;

each of $X_1$, $X_2$, and $X_3$ is each independently —$Y_2$, —O—$Y_2$, —S—$Y_2$, —NH—$Y_2$, —CO—O—$Y_2$, —O—CO—$Y_2$, —CO—NH—$Y_2$, —CO—$NY_1Y_2$, —NH—CO—$Y_2$, —$SO_2$—$Y_2$, —$SO_2$—O—$Y_2$, —$CHY_1Y_2$, or —$NY_1Y_2$;

each of $Y_1$, $Y_2$, and $Y_3$ is each independently —H, -Q-Z—H or —Z—H; in which each Q, independently, is —$R^a$—O—[Si($CH_3$)$_2$—O—]$_{1-100}$-, —$C_{1-2000}$ alkyl-, —$C_{6-40}$ aryl-, —$C_{7-2000}$ alkylaryl-, —$C_{7-2000}$ arylalkyl-, —($C_{1-30}$ alkyl ether)$_{1-100}$-, —($C_{6-40}$ aryl ether)$_{1-100}$-, —($C_{7-2000}$ alkylaryl ether)$_{1-100}$-, —($C_{7-2000}$ arylalkyl ether)$_{1-100}$-, —($C_{1-30}$ alkyl thioether)$_{1-100}$-, —($C_{6-40}$ aryl thioether)$_{1-100}$-, —($C_{7-2000}$ alkylaryl thioether)$_{1-100}$-, —($C_{7-2000}$ arylalkyl thioether)$_{1-100}$-, —($C_{2-50}$ alkyl ester)$_{1-100}$-, —($C_{7-2000}$ aryl ester)$_{1-100}$-, —($C_{8-2000}$ alkylaryl ester)$_{1-100}$-, —($C_{8-2000}$ arylalkyl ester)$_{1-100}$-, —$R^a$—CO—O—($C_{1-30}$ alkyl ether)$_{1-100}$-, —$R^a$—CO—O—($C_{6-40}$ aryl ether)$_{1-100}$-, —$R^a$—CO—O—($C_{7-2000}$ alkylaryl ether)$_{1-100}$-, —$R^a$—CO—O—($C_{7-2000}$ arylalkyl ether)$_{1-100}$-, —($C_{4-50}$ alkyl urethane)$_{1-100}$-, —($C_{14-60}$ aryl urethane)$_{1-100}$-, —($C_{10-2000}$ alkylaryl urethane)$_{1-100}$-, —($C_{10-2000}$ arylalkyl urethane)$_{1-100}$-, —($C_{5-50}$ alkyl urea)$_{1-100}$-, —($C_{14-60}$ aryl urea)$_{1-100}$-, —($C_{10-2000}$ alkylaryl urea)$_{1-100}$-, —($C_{10-2000}$ arylalkyl urea)$_{1-100}$-, —($C_{2-50}$ alkyl amide)$_{1-100}$-, —($C_{7-60}$ aryl amide)$_{1-100}$-, —($C_{8-2000}$ alkylaryl amide)$_{1-100}$-, —($C_{8-2000}$ arylalkyl amide)$_{1-100}$-, —($C_{3-30}$ alkyl anhydride)$_{1-100}$-, —($C_{2-50}$ aryl anhydride)$_{1-100}$-, —($C_{9-2000}$ alkylaryl anhydride)$_{1-100}$-, —($C_{9-2000}$ arylalkyl anhydride)$_{1-100}$-, —($C_{2-30}$ alkyl carbonate)$_{1-100}$-, —($C_{7-50}$ aryl carbonate)$_{1-100}$-, —($C_{8-2000}$ alkylaryl carbonate)$_{1-100}$-, —($C_{8-2000}$ arylalkyl carbonate)$_{1-100}$-, —$R^a$—O—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$-, —$R^a$—O—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$-, —$R^a$—O—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$-CO—NH—($R^b$ or Ar—$R^b$—Ar)—NH—CO—O—, —$R^a$—O—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$-$R^c$—O—CO—NH—($R^b$ or Ar—$R^b$—Ar)—NH—CO—O—, —$R^a$—NH—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$-, —$R^a$—NH—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester)$_{1-100}$-, —$R^a$—NH—CO—NH—($R^b$ or Ar—$R^b$—Ar)—NH—CO—O—($C_{1-30}$ alkyl ether, $C_{6-40}$ aryl ether, $C_{7-2000}$ alkylaryl ether, or $C_{7-2000}$ arylalkyl ether)$_{1-100}$-CO—NH—($R^b$ or Ar—$R^b$—Ar)—NH—CO—O—, —$R^a$—NH—CO—NH—($R^b$ or Ar—$R^b$—Ar)—NH—CO—O—($C_{2-50}$ alkyl ester, $C_{7-60}$ aryl ester, $C_{8-2000}$ alkylaryl ester, or $C_{8-2000}$ arylalkyl ester$)_{1-100}$-$R^c$—O—CO—NH—($R^b$ or Ar—$R^b$—Ar)—NH—CO—O—, —$R^a$—O—CO—NH—($R^b$ or Ar—$R^b$—Ar)—NH—CO—NH—($C_{2-50}$ alkyl amide, $C_{7-60}$ aryl amide, $C_{8-2000}$ alkylaryl amide, or $C_{8-2000}$ arylalkyl amide$)_{1-100}$-, —$R^a$—NH—CO—NH—($R^b$ or Ar—$R^b$—Ar)—NH—CO—NH—($C_{2-50}$ alkyl amide, $C_{7-60}$ aryl amide, $C_{8-2000}$ alkylaryl amide, or $C_{8-2000}$ arylalkyl amide$)_{1-100}$-, —$CH_2$—CH(OH)—$CH_2$—$(OCH_2CH_2)_{1-100}$—, $OCH_2CH(OH)$—$CH_2$—, —$CH_2$—CH(OH)—$CH_2$—$N^+HR^a$—$(CH_2CH_2N^+R^aR^b)_{1-100}$—$CH_2CH_2N^+HR^a$—$CH_2CH(OH)CH_2$—, or —$CH_2CH_2$—$N^+R^aR^b$—$(CH_2CH_2N^+R^aR^b)_{1-100}$—$R^c$—; and each Z, independently, is —$R^a$—, —$R^a$—Ar—, —Ar—$R^a$—, or —Ar—; and $V_1$ and $V_2$ independently are hydrogen, $C_{1-2000}$ alkyl, $C_{6-40}$ aryl, or $C_{7-2000}$ alkyl aryl, optionally substituted with —OH, —SH, —$NH_2$, —NHOH, —$SO_3H$, —$OSO_3H$, —$CO_2H$, —$CONH_2$, —$CONHNH_2$, —CH$(NH_2)$—$CO_2H$, —NH—$CH_2$—$CO_2H$, —$P(OH)_3$, —$PO(OH)_2$, —O—$PO(OH)_2$, —O—PO(OH)—O—$PO(OH)_2$, —O—PO(O—)—O—$CH_2CH_2NH_3^+$, —O—PO(O)—O—$CH_2CH_2$—$N^+(CH_3)_3$, -glycoside, -oligosaccharide, —CO-glycoside, —CO-oligosaccharide, —$OCH_3$, —$OCH_2(CHOH)_4$—$CH_2OH$, —$OCH_2(CHOH)_2$—$CH_2OH$, —CO—$OCH_2(CHOH)_4$—$CH_2OH$, —$C_6H_3(OH)_2$, —$N(CH_2CO_2H)_2$, —CO—$N(CH_2CO_2H)_2$, —CO—NH—$C(CH_2CH_2CO_2H)_3$, —CO—NH—$C(CH_2CH_2OH)_3$, —$[CH_2$—$CH(CO_2R^a)]_{1-100}$—H, —O—$(CH_2CH_2O)_{1-100}$—H, —$NH_3^+$, —$N^+H_2R^a$, —$N^+HR^aR^b$, or —$N^+R^aR^bR^c$;

wherein each of $R^a$, $R^b$, and $R^0$ are each independently $C_{1-20}$ linear or branched alkyl;

Ar is aryl;

W is hydroxyl or amino;

p and s each independently is 0-20;

q is 1; and r is 0 or 1 provided that at least one occurrence of r is 1.

2. The compound of claim 1, wherein M is a Pd ion;

wherein Abx is vancomycin;

wherein $E_2$ and $E_3$ are each independently $Y_1$,$Y_2$-amino, $Y_2$-amino, ($Y_1$,$Y_2$-alkyl)-amino, $Y_1$,$Y_2$-ethylenediamino, (dihydroxymethyl)alkylamino, ($X_1$,$X_3$-aryl)amino, ($Y_1$,$Y_2$,$Y_3$-alkyl)amino, ($Y_1$,$Y_2$,$Y_3$-aryl)amino, dihydroxyalkylamino, (trihydroxyalkyl)alkylamino, or (dicarboxyalkyl)amino; and wherein $Y_1$ and $Y_2$ are each independently —H;

B is hydroxy-$C_{1-200}$ alkyl, wherein the hydroxyl is linked to a Ma carbonyl group as an ester;

Ma is —NH—CO-cyclopropanyl-CO—;

p is 0;

each occurrence of r is 1;

wherein each of $X_1$, $X_2$, and $X_3$ is hydrogen;

wherein $V_2$ is H, —NH3$^+$, —$N^+H_2R^a$, —$N^+HR^aR^b$, —$N^+R^aR^bR^c$, or —NH—$(CH_2CH_2N^+R^aR^b)_{1-100}$—$R^c$; the counter anion is chloride, bromide, iodide, triiodide, sulfate, pyrosulfate, bisulfate, sulfite, bisulfite, thiosulfate, nitrate, nitrite, phosphate, azide, thiocyanate, selenocyanate, or acetate.

3. A pharmaceutical composition, comprising a pharmaceutically acceptable carrier and a compound of claim 1.

4. A method of photodynamic therapy, comprising applying the composition of claim 3 to a site on the skin of a subject and exposing the site of application on the skin to visible light for excitation of the compound.

5. The method of claim 4, wherein the fullerene/photosensitizer covalently-bonded antibiotic compound has antibiotic effects in addition to photodynamic effects wherein the site on the skin is a site of wound infection, burn infection, acne, soft-tissue infection, oral infection, dental infection, leishmaniasis, mycobacterial infection, keratitis, otitis media, sinusitis, localized tuberculosis, or fasciitis.

6. A method of photodynamic therapy, comprising administering the composition of claim 3 to a site of disease in a subject and exposing the site of administration to visible light for excitation of the fullerene/photosensitizer covalently-bonded antibiotic compound, wherein the site of administration is a site of gastric *H. pylori* infection, intra-abdominal abscess, cystitis, urinary tract infections, genital tract infections, osteomyelitis, onychomycosis, viral infections.

* * * * *